US012589188B2

(12) United States Patent
Myung et al.

(10) Patent No.: US 12,589,188 B2
(45) Date of Patent: Mar. 31, 2026

(54) HYDROGELS FOR IN SITU-FORMING TISSUE CONSTRUCTS

(71) Applicants: The Board of Trustees of the Leland Stanford Junior University, Stanford, CA (US); The United States Government as represented by the Department of Veterans Affairs, NW Washington, DC (US)

(72) Inventors: David Myung, Saratoga, CA (US); Fang Chen, Stanford, CA (US); Gabriella Fernandes-Cunha, Palo Alto, CA (US); Sarah Hull, Stanford, CA (US); Sarah Heilshorn, Mountain View, CA (US); Christopher Lindsay, San Mateo, CA (US); Christopher Madl, Los Altos, CA (US); Hyun Jong Lee, Gyeonggi-do (KR)

(73) Assignees: The Board of Trustees of the Leland Stanford Junior University, Stanford, CA (US); The United States Government as represented by the Departement of Veterans Affairs, Washington, DC (US)

( * ) Notice: Subject to any disclaimer, the term of this patent is extended or adjusted under 35 U.S.C. 154(b) by 782 days.

(21) Appl. No.: 17/997,097

(22) PCT Filed: Apr. 29, 2021

(86) PCT No.: PCT/US2021/029955
§ 371 (c)(1),
(2) Date: Oct. 25, 2022

(87) PCT Pub. No.: WO2021/222612
PCT Pub. Date: Nov. 4, 2021

(65) Prior Publication Data
US 2023/0263943 A1     Aug. 24, 2023

Related U.S. Application Data

(60) Provisional application No. 63/017,621, filed on Apr. 29, 2020.

(51) Int. Cl.
*A61F 13/00*     (2024.01)
*A61F 2/14*     (2006.01)
(Continued)

(52) U.S. Cl.
CPC .............. *A61L 27/52* (2013.01); *A61F 2/142* (2013.01); *A61L 27/26* (2013.01);
(Continued)

(58) Field of Classification Search
CPC .............. A61F 13/01029; A61F 2/0036; A61F 2002/30004; A61F 2002/30069;
(Continued)

(56) References Cited

U.S. PATENT DOCUMENTS

2006/0083773 A1 *   4/2006   Myung .................. A61K 35/44
                                                                    623/5.16
2007/0212385 A1     9/2007   Myung et al.
(Continued)

FOREIGN PATENT DOCUMENTS

WO     WO-2018144966 A1 *   8/2018   ............. A61K 47/60

OTHER PUBLICATIONS

WO 2018/144966 A1 (Year: 2018).*

*Primary Examiner* — Kim M Lewis
(74) *Attorney, Agent, or Firm* — Pamela J. Sherwood; Bozicevic, Field & Francis LLP

(57) ABSTRACT

Compositions and methods are provided for lamellar and defect reconstruction of corneal stromal tissue using bioma-
(Continued)

terials that form a defined hydrogel structure in situ, including interpenetrating (IPN) and semi-IPN hydrogels.

19 Claims, 28 Drawing Sheets

(51) Int. Cl.
  *A61L 27/26*  (2006.01)
  *A61L 27/52*  (2006.01)
(52) U.S. Cl.
  CPC ... *A61F 2210/0085* (2013.01); *A61L 2400/06*
    (2013.01); *A61L 2430/16* (2013.01)
(58) Field of Classification Search
  CPC .. A61F 2002/30133; A61F 2002/30383; A61F
    2002/30387; A61F 2002/30507; A61F
    2002/30581; A61F 2002/30754; A61F
    2002/3082; A61F 2002/4628; A61F
    2230/0015; A61F 2250/0014; A61F
    13/01025; A61F 13/01038; A61F
    13/0209; A61F 13/2025; A61F 13/2042;
    A61F 13/2051; A61F 13/2068; A61F
    13/2071; A61F 13/266; A61F 13/34;
    A61F 2/4425; A61F 2002/30131; A61F
    2002/30586; A61F 2002/30593; A61F
    2013/00161; A61F 2013/00182; A61F
    2013/00272; A61F 2013/00306; A61F
    2013/00387; A61F 2013/00846; A61F
    2013/15073; A61F 2013/4593; A61F
    2230/0013; A61F 2230/0017; A61F
    2230/0023; A61F 2230/0069; A61F 2/00;
    A61F 2/1648; A61F 2/90; A61F 2/92;
    A61F 2002/072; A61F 2002/30405; A61F
    2002/30451; A61F 2002/30471; A61F
    2002/30604; A61F 2002/30677; A61F
    2002/4629; A61F 2220/0058; A61F
    2220/0091; A61F 2230/0071; A61F
    2250/0003; A61F 5/4404; A61F 5/443;
    A61F 5/445; A61F 13/2022; A61F
    2/0077; A61F 2/141; A61F 2/1601; A61F
    2/1627; A61F 2/24; A61F 2/3099; A61F
    2/3877; A61F 2/484; A61F 2/7812; A61F
    2/80; A61F 2/885; A61F 2/91; A61F
    2/954; A61F 2002/0068; A61F 2002/065;
    A61F 2002/1683; A61F 2002/169; A61F
    2002/30148; A61F 2002/30153; A61F
    2002/30156; A61F 2002/30242; A61F
    2002/30398; A61F 2002/30476; A61F
    2002/4445; A61F 2002/4622; A61F
    2002/4627; A61F 2002/807; A61F
    2013/0068; A61F 2230/0019; A61F
    2310/00011; A61F 2310/00173; A61F
    2310/00407; A61F 2310/00976; A61F
    13/0206; A61F 13/0246; A61F 13/42;
    A61F 2002/16905; A61F 2002/2817;
    A61F 2002/30171; A61F 2002/30179;
    A61F 2002/30224; A61F 2002/30365;
    A61F 2002/30367; A61F 2002/30571;
    A61F 2002/30578; A61F 2002/30841;
    A61F 2002/445; A61F 2009/00872; A61F
    2013/00119; A61F 2210/00; A61F
    2230/005; A61F 2230/0058; A61F
    2230/0067; A61F 2250/0058; A61F
    9/008; A61F 9/04; A61F 13/02; A61F
    13/022; A61F 2/022; A61F 2/08; A61F
    2/0811; A61F 2/1616; A61F 2/20; A61F
    2/2418; A61F 2/30744; A61F 2/30771;
    A61F 2/44; A61F 2002/075; A61F
    2002/0852; A61F 2002/0888; A61F
    2002/30225; A61F 2002/30354; A61F
    2002/30495; A61F 2002/30594; A61F
    2002/30766; A61F 2002/30914; A61F
    2002/4685; A61F 2009/00865; A61F
    2250/0023; A61F 2250/0024; A61F
    2250/0069; A61F 2310/00389; A61F
    13/01012; A61F 13/84; A61F 15/001;
    A61F 2/0009; A61F 2/062; A61F
    2/30988; A61F 2/86; A61F 2/88; A61F
    2/915; A61F 2002/009; A61F 2002/0894;
    A61F 2002/1689; A61F 2002/30011;
    A61F 2002/30031
  See application file for complete search history.

(56)    References Cited

U.S. PATENT DOCUMENTS

| | | |
|---|---|---|
| 2010/0010114 A1 | 1/2010 | Myung et al. |
| 2014/0120177 A1 | 5/2014 | Ward et al. |
| 2021/0187160 A1 | 6/2021 | Bright et al. |

\* cited by examiner

| Samples | Refractive index (n) | Surface focal power (Ds, m⁻¹)* | Surface focal Length (Fs, mm)* |
|---|---|---|---|
| HA50-Col1 | 1.3431 | 42.9 | 23.3 |
| HA50-Col2 | 1.3428 | 42.8 | 23.3 |
| HA50-Col3 | 1.3423 | 42.8 | 23.4 |
| HA30-Col3 | 1.3402 | 42.5 | 23.5 |
| HA10-Col3 | 1.3403 | 42.5 | 23.5 |
| Human cornea | 1.3760* | 47.0 | 21.3 |

* $Ds=(n-1)/r$, r: radius of curvature (8 mm for human).
* Adapted from literature.

Control 1: Collagen gel; Control 2: Collagen gel with chemically conjugated HA.

B

C

D

E

A

B.

HYDROGELS FOR IN SITU-FORMING TISSUE CONSTRUCTS

CROSS-REFERENCE TO RELATED APPLICATIONS

The present application claims the benefit of and priority to U.S. Provisional Patent Application No. 63/017,621 filed Apr. 29, 2020 the entire disclosure of which is hereby incorporated by reference herein in its entireties for all purposes.

STATEMENT REGARDING FEDERALLY SPONSORED RESEARCH

This invention was made with Government support under contracts EY028176, and EY026877 awarded by the National Institutes of Health; and RX003179 awarded by the Veteran's Administration. The Government has certain rights in the invention.

BACKGROUND

The cornea is the dome-shaped and transparent outermost part of eye. It serves a critical dual role in both focusing light onto and protecting intraocular neurosensory structures. Corneal injury or diseases can quickly lead to scarring, thinning, and eventually blindness, which has been estimated to affect 23 million people worldwide. Although corneal transplantation can treat corneal blindness effectively, it can benefit less than 1.5% patients with corneal blindness due to the shortage of donor corneas and a global imbalance in donor cornea supply and demand. Moreover, although corneas are immune privileged compared to most tissues in the body, a transplanted donor cornea is still at risk of serious complications such as infections and rejection. Traditional cornea transplantation-penetrating keratoplasties (PKPs) also have inherent risk of graft dehiscence with even minor trauma. Although some of these risks can be addressed by novel cornea transplantation technique-anterior lamellar graft (epithelial keratoplasty), these advanced procedures are not available for most cases worldwide. Endothelial keratoplasty has emerged as a sutureless way to replace just the endothelium of corneas in cases of Fuch's dystrophy or other causes of bullous keratopathy. However, surgical treatment of any damage or scarring anterior to the endothelium requires meticulous dissection, precise sizing, and numerous sutures for proper placement as full thickness or lamellar graft.

A promising strategy to overcome these limitations of corneal transplantation is using biomaterials to replace the damaged cornea tissues. Currently, cyanoacrylate glue is used off-label clinically as a temporizing agent to stabilize corneal defects prior to a corneal transplantation, but it forms an opaque plaque that offers to no improvement in vision. Typical biomaterials being developed for corneal tissue engineering are hydrogels, which are networks of hydrophilic polymer chains that can hold a large amount of water. An ideal hydrogel for cornea replacement should have similar physical, chemical, and physiobiological properties with native corneal stromal tissue. The fundamental features of an ideal hydrogel to mimic a cornea include: 1) high transparency for visible light transmittance, 2) high water content, 3) mechanical stability on the cornea after application, 4) no toxicity nor toxic decomposition products, 5) good biointegration but no interferences with adjacent tissues, and 6) support physiobiological functions of adjacent tissues, 7) ease of application. These features are heavily dependent on both the nature of the polymer and the crosslinking method involved.

An in situ-forming hydrogel that can be applied to a corneal defect to form a stromal tissue substitute could attend to these requirements without the need for sutures or even incisions. A crosslinked recombinant human collagen type Ill-based implants (RHCIII-MPC) has been reported to improve visions of patients with scarred or ulcerated corneas from severe infection. In prior work, we reported on the development of a biocompatible hyaluronate hydrogel crosslinked via visible light-induced thiol-ene reaction. Although photo-initiation crosslinking is efficient and highly controllable, its application for in situ gel forming on cornea poses certain limitations such as the need for an external light energy source, a photo-initiator, and reactive side products. Improved compositions and methods for this purpose are therefore desirable.

SUMMARY

Hydrogel compositions are provided that flow into tissue, e.g. corneal defects, and crosslink after a short period of time to form a solid hydrogel. The hydrogels may comprise a chemically cross-linked or physically associated RGD (or YIGSR) containing first polymer; which may be combined in the hydrogel with a second cross-linked polymer. In some embodiments the first polymer is a collagen polypeptide, which comprises RGD motifs. In other embodiments the first polymer is an RGD oligopeptide, e.g. KKKRGDKKK, KKKRGD or a YIGSR oligopeptide, e.g. KKKYIGSRKKK, KKKYIGSR; etc.

In some embodiments the hydrogel comprises a interpenetrating polymer network (IPN) of at least two independently chemically crosslinked polymers, including biopolymers which include, without limitation, hyaluronic acid (HA) and collagen, without chemical bonding between the two networks. The IPN can be formed simultaneously or sequentially.

In some embodiments the hydrogel comprises a semi-interpenetrating polymer network. The IPN can be a semi-IPN if one of the two polymers is not chemically cross-linked. In some such embodiments a first polymer may be comprised of collagen or HA in the absence of chemical cross-linking, e.g. where the association between polymers forms through non-covalent interactions. The second polymer may be, for example, crosslinked HA; cross-linked collagen, etc.

IPNs and semi-IPNs are able to take on the characteristics of each of their component polymer networks. For example, the HA-collagen IPN/semi-IPN hydrogels can provide advantages over HA and collagen alone by combining the cell adhesion properties of the collagen network while being mechanically strengthened by the presence of the cross-linked HA network. With chemical cross-linking, each of the polymer components may be cross-linked with a different modality so that independent networks are formed. Suitable cross-linking modalities include, without limitation, SPAAC click reactions; thiol-ene click reactions, for example using a mildly basic conditions to drive the thiol-ene click reaction without using light or any exogenous chemical catalyst; etc. In some embodiments, both networks of the IPN are formed simultaneously within the mixture, rather than sequentially. N-hydroxysuccinimide-based crosslinking can also be employed if one of the networks is comprised of a protein and the other network is not a protein and is devoid of amines which would react with the NHS, e.g. a combination of collagen and HA. Preferably the IPN is formed in situ without the need for an external energy source such as light, heat, or a chemical catalyst such as copper or initiator.

In some embodiments, the hydrogel is a composite of two or more polymers, such as collagen and PEG or collagen and HA, where the two polymers are covalently linked to each other. For instance, collagen may be crosslinked by multi-arm PEG-NHS, or crosslinked by an NHS-functionalized HA. Collagen and PEG or collagen and HA can be covalently crosslinked to each other by means of click chemistry (e.g. SPAAC or Diels-Alder), where an azide moiety on one of the molecules reacts with an alkyne moiety on the other molecule (e.g. Collagen-alkyne and HA-azide, or Collagen-alkyne and bifunctional or multifunctional PEG-azide). In addition, Collagen can be functionalized in one aliquot with an alkyne and in another aliquot with an azide, so when the two aliquots are mixed, they are reacted via click chemistry (e.g. SPAAC) to form a crosslinked hydrogel matrix. In all cases, a PEG spacer arm can be optionally placed in between the azide or alkyne and the polymers.

In some embodiments the water content of the hydrogel is up to 90% weight/volume, up to 91%, up to 92%, up to 93%, up to 94%, up to 95%, up to 96%, up to 97%, up to 98%, up to 99%. The ratio of first polymer to second polymer, e.g. collagen to HA, weight/weight may be about 1:25; 1:20; 1:15; 1:10; 1:5; 1:1, etc. The amount of time for cross-linking may be up to 30 seconds, up to 1 minute, up to 90 seconds, up to 2 minutes, up to 3 minutes, up to 4 minutes, up to 5 minutes, and usually less than about 60 minutes.

In some embodiments the first polymer in the hydrogel is an RGD oligopeptide, e.g. KKKRGDKKK, KKKRGD or a YIGSR oligopeptide, e.g. KKKYIGSRKKK, KKKYIGSR; etc., e.g. oligomeric peptide sequences, comprising an RGD and/or YIGSR motif and amino acid residues that provide primary amine groups. The primary amine groups, e.g. lysine, provide crosslinkability, while the RGD and/or YIGSR sequences provide cell adhesiveness to the peptide sequence. The oligopeptides may be cross-linked with PEG molecules with two or more arms, including, for example, PEG with 3, 4, 5, 6, 7, 8 or more arms that is functionalized with reactive groups, e.g. an N-hydroxysuccinimide-based functional group. PEG comprising 4 arms or 8 arms are exemplary, e.g. with the oligopeptide KKKRGDKKK. In certain embodiments an RGD oligopeptide is combined with a 4-arm PEG-succinimidyl carboxyl methel ester at a ratio of from about 5:1 molar ratio of PEG to oligopeptide to about 10:1 ration, and may be, for example 7:1, 21:4, etc. Upon mixing the polymers cross-link to form a hydrogel without the need for an external energy source. Alternatively the first polymer can also be used in the formation of an IPN or semi-IPN with a second polymer.

RGD polymers, e.g. collagen polypeptides, RGD oligopeptides, etc. crosslinked via multifunctional PEG succinimidyl esters can be formed rapidly in situ and used to support epithelial overgrowth and stromal tissue ingrowth when applied to corneal stromal defects. The gels form rapidly under ambient conditions without the need for a chemical or photochemical trigger. A greater number of cross-links, e.g. using an 8 arm PEG vs. a 4 arm PEG, can provide for slower in vivo degradation. Using PEG of from about 4 to about 8 arms, an epithelial layer can migrate over the hydrogel and form a multilayer. The hydrogels are cytocompatible; morphological and proliferation of corneal cells are superior to that seen on non-crosslinked collagen hydrogels.

In another embodiment, a composite polymer between two naturally derived polymers can be constructed, such as covalently bonded collagen and HA, e.g. a hyaluronate-collagen copolymeric hydrogel formed with hyaluronate-DBCO and collagen-azide via SPAAC click gelation. It was found that the transmittance was particularly beneficial with this combination of agents. Hyaluronate became opaque after modification with DBCO and the opaqueness increased as the amine-to-DBCO molar ratio decreased. The transmittance of hyaluronate-collagen copolymeric hydrogel decreased significantly when using hyaluronate-DBCO and collagen-azide to form the gel than using hyaluronate-azide and collagen-DBCO.

For corneal implants, optical transparency is desirable. At wavelengths between 300 and 800 nm, transmittance of greater than about 70%, about 80%, about 90%, about 95% is desirable. Cross-linked hydrogels have generally improved transparency relative to non-cross-linked gels. Collagen-PEG hydrogel degradation is dependent on the PEG functionality and concentration. Increasing crosslinks, i.e. higher number of collagen arms, improves susceptibility to degradation.

In some embodiments the hydrogel composition is applied to a corneal defect in a flowable liquid state and allowed to form a smooth contour on its surface as it gels. The IPN-treatment can promote epithelial overgrowth, promote tight junction formation in the epithelium, and decrease myofibroblast activity in the wounded stroma. The lower refractive index of the gel may lead to under-power of corneal surface if the gel assumes the same contour as the host's normal cornea. The focal power or focal length can be matched to naïve cornea by changing the radius curvature. In some embodiments the curvature of central cornea is adjusted by changing the volume of applied hydrogel, to compensate the slightly lower refractive index of the hydrogel to get the same focal length. Alternatively the gel can be used in conjunction with a contact lens. In some embodiments additives are included in the gel to increase its refractive index, for example by the inclusion of stromal cells (e.g. keratocytes).

Compositions, kits and methods are provided for use as in-situ forming tissue constructs, also referred to as a defined hydrogel structure, that can be cellularized to aid in wound healing and tissue regeneration, particularly in repair, regeneration, and/or reconstruction of lamellar or partial defects of wounded corneal tissue. The compositions, kits and methods also find use in the repair, regeneration, and/or reconstruction of skin, subcutaneous tissue, nerve, muscle, bone, cartilage, vitreous, tendon, ligament, fat, retinal, conjunctival, scleral, cardiac, adrenal, and other types of tissue.

In an embodiment, a flowable biomaterial composition for use as an in-situ-forming corneal construct, i.e. a defined hydrogel structure, is provided, which finds use in treating or reconstructing a surgically incised or wounded corneal area in a mammalian subject in need thereof. The flowable biomaterial may comprise cells or therapeutic agents, or both, that aid in treating or reconstructing a surgically incised or wounded area, where the cells or agent are entrapped or encapsulated in the defined hydrogel structure. Cells of interest include regenerative cells, such as a stem cell, including without limitation corneal stem cells. Cells suitable for treating corneal tissue may include, for example, one or more of corneal stromal stem cells, mesenchymal cells, keratocytes, keratinocytes, endothelial cells, and epithelial cells, and limbal epithelial cells, and transient amplifying cells.

In another aspect, a method of treating or reconstructing a surgically incised or wounded corneal site in a mammalian subject is provided, by administering a flowable biomaterial that forms a defined hydrogel structure at the site under ambient conditions without the need for an external stimulus such as light. The defined hydrogel structure is effective in treating or reconstructing the wounded corneal area. In some embodiments the flowable biomaterial is applied to an existing cavity, which can be highly irregular in shape, e.g. a pathologic cavity such as an ulcer. In some embodiments a cavity is debrided to eliminate necrotic material and create fresh wound edges. In some embodiments a cavity of specific shape and dimensions created, e.g. with surgical instruments, or a laser, for example to remove tissue that is scarred, fibrotic, opacified, etc.

In another aspect, the flowable biomaterial, or a defined hydrogel structure derived therefrom as described above, is provided, which optionally comprises cells, therapeutic agents, etc. The cytocompatible hydrogel structure is suitable for use in tissue repair or regeneration.

In yet another aspect, the instant disclosure includes a kit for making a corneal construct for use in treating or reconstructing a surgically incised or wounded corneal area in a mammalian subject. A kit will comprise a flowable biomaterial that forms a defined hydrogel structure at the site under ambient conditions without the need for an external stimulus such as light. The defined hydrogel is effective in treating or reconstructing a wounded corneal area. The flowable biomaterial may be provided as a single composition, or may be provided as two compositions in separate containers.

The gels in the present invention can serve as, but not be limited to, tissue scaffolds, tissue substitutes, optical elements (e.g. corneal or lens tissue), tissue fillers, tissue spacers, or as delivery vehicles for cells, tissues, and/or pharmaceutical agents.

These and other embodiments of the subject invention will readily occur to those of skill in the art in view of the disclosure herein.

BRIEF DESCRIPTION OF THE FIGURES

FIG. 22. RGD gel 1 (left) and trilysine gel (right), at Day 5 of cell adhesion assay.

In situ rheology test indicated that the semi-IPN and its two controls started to gel as soon as all the gel components were mixed and the half of the gelation completed within 10 minutes. Collagen gels had the same composition as the semi-IPN except there was no HA. HA-Col gel had the same composition as the semi-IPN except that the HA was chemically conjugated onto collagen rather than physically entangling. (C) Transmittance spectra showed that the semi-IPN were highly transparent in the visible light range even with after cell encapsulation. (D) Rheology study showed that the HA decreased the stiffness while chemically conjugated HA increased the stiffness of the collagen gel. (E) The fraction of HA in the semi-IPN had an impact on the stiffness of the gel. When collagen-to-HA ratio was 2:1 (red), the semi IPN was the stiffest compared to the ratios of 4:1 (green) and 1:1 (black).

Figure 24:
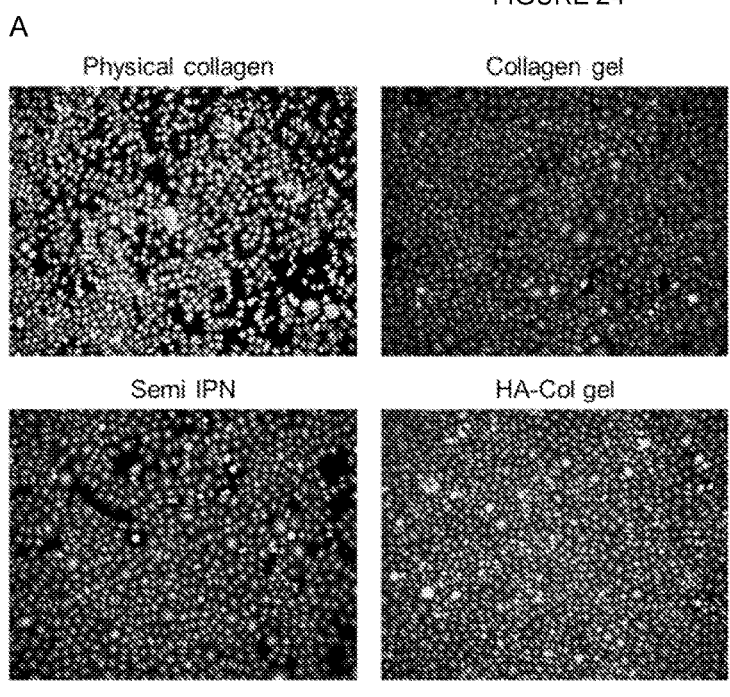
Figure 24:
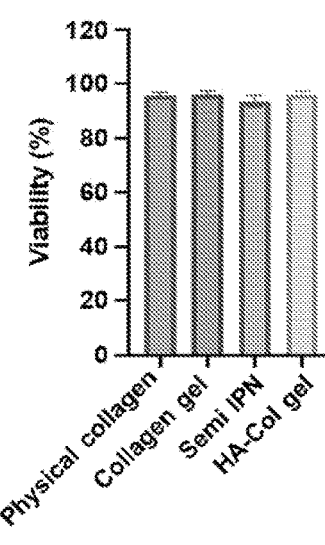
Figure 24:
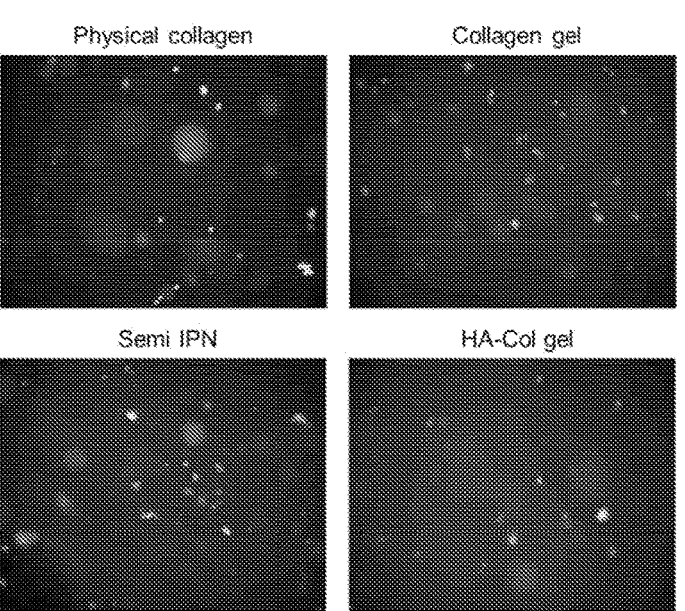
Figure 24:
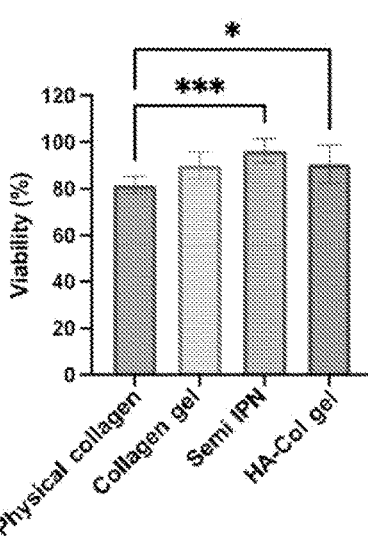
Figure 25:
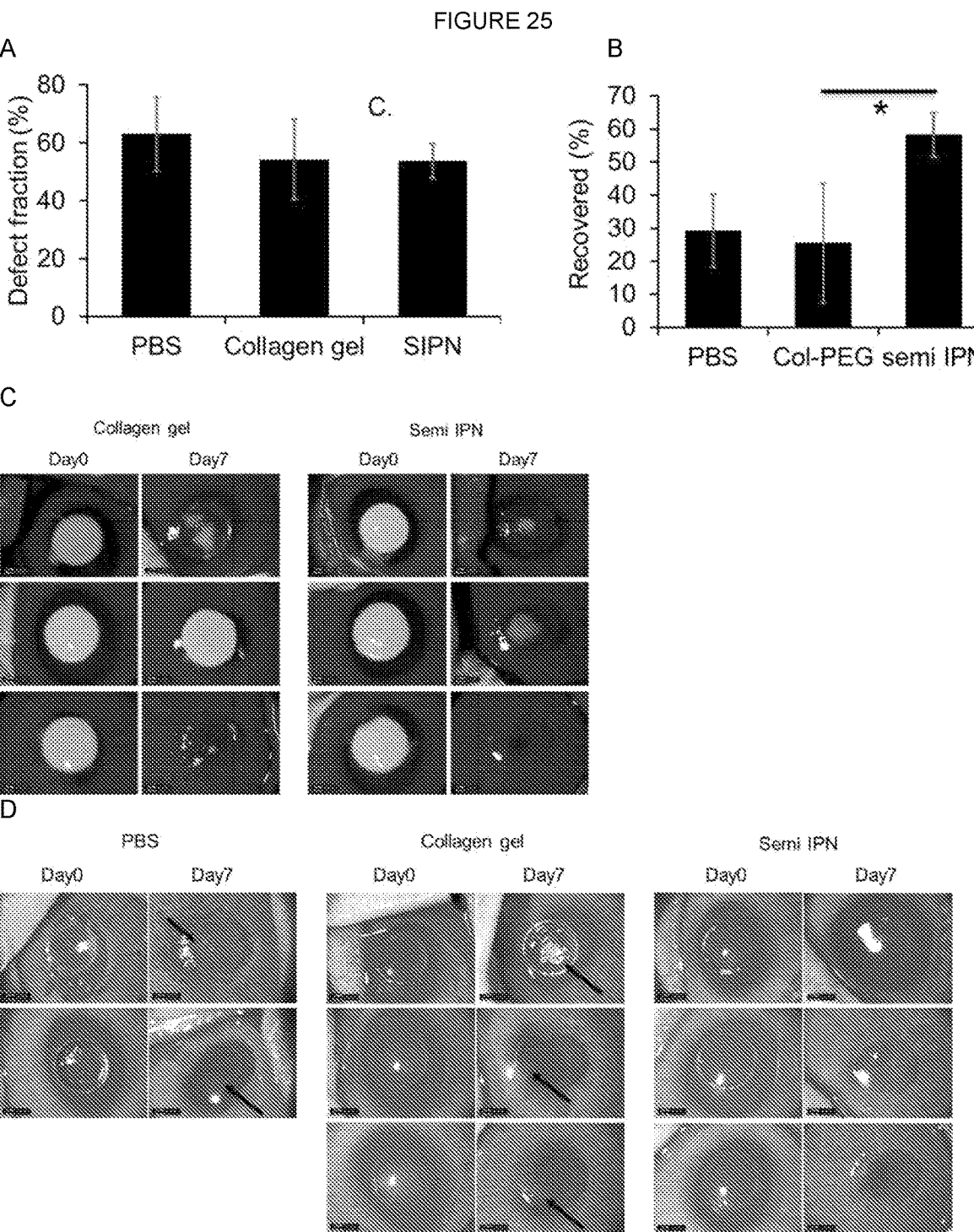

FIGS. 24A-B. Cytocompatibility of gels with corneal cells. (A) Representative images (left) and quantification (right) of a live/dead assay of corneal epithelial cells on top of the gels. All tested gels showed excellent biocompatibility to the corneal epithelial cells. (B) Representative images (left) and quantification (right) of a live/dead assay of corneal mesenchymal stromal cells inside the gels. The corneal mesenchymal stromal cells showed the highest viability when encapsulated in the semi-IPN gel.

FIGS. 25A-D. In vivo corneal wound healing upon treatment with the gels. (A) Corneal defect fraction created for corneal wound disease model. There were no significant differences among the groups, indicating the defect were created equally. (B) Recovered corneal stroma on the seventh day after the creation of disease and treatment. The semi-IPN treated group showed a significantly higher recovery of corneal stroma compared to the collagen gel (Col-PEG). (C) Fluorescein staining images of the corneas treated with semi IPN showed a faster corneal re-epithelialization than those treated with the collagen gel. (D) Slit light exam photos of the experimental eyes showed that the corneas treated with semi IPN were the clearest compared to those treated with PBS or collagen gel on day 7.

FIGS. 26A-D. Functional wound healing with collagen-HA cross-linked with SPAAC. (A) Collagen Type IV (yellow stain, white arrow) and (B) Laminin (green, white arrow) are observed at the interface between the multi-layered epithelium and Col-HA gel (pink). (C) Beta tubulin-III (green) staining of corneal nerves (white arrow) in the vicinity of the gel and regenerated epithelium. (D) Actin staining (green) of the endothelium (white arrow) in the treated cornea (gel not stained).

FIGS. 27A-E. Images taken 8 weeks after treating deep keratectomy wounds, showing expression of (a) CK3 after Collagen gel, (b) CK3 after Col-HA gel, (c) CK3 of native cornea, (d) alpha-SMA after Collagen gel, (e) alpha-SMA after Col-HA gel, and (f) residual collagen gel (pink) at wound site. Collagen gels were crosslinked by succinimide chemistry while Col-HA gels were crosslinked via SPAAC. (CK3 in green, alpha-SMA in red with minimal staining). Scale Bar=20 microns FIGS. 28A-B. (A) Intraocular pressure and (B) pachymetry (corneal thickness) of rabbit corneas treated with collagen-HA (Col-HA) crosslinked by SPAAC, and collagen alone crosslinked by 4-arm PEG NHS, at 2 months.

FIGS. 29A-E. Schematic of a prepared surgical wound filled being with gel. (A) Corneal scar. (B) c-MSCs are delivered within a viscous gel precursor solution into a pre-existing or surgically-created wound after scar removal followed by (C) in situ gelation. (D-E) Epithelialization over the gel ensues followed by (F) re-modeling of the gel and restoration of transparent corneal stroma.

FIGS. 30A-D. Schematic of a pathological wound filled with gel. (A) Corneal stromal ulcer (B) c-MSCs are delivered within a viscous gel precursor solution into a pre-existing pathological stromal wound followed by (C) in situ gelation. (D-E) Epithelialization over the gel ensues followed by (F) re-modeling of the gel and restoration of transparent corneal stroma. In one embodiment of this invention, the gel fills a perforated wound where there is a defect at the base of the lesion that communicates with the anterior chamber of the eye, which is sealed off by the gel.

FIGS. 31A-E. (A) An automated, dual-chamber gel dispenser that enables mixing of two precursor solutions through a microfluidic mixing channel driven by a linear solenoid powered by a battery. (B) A spring-driven, mechanical, dual-chamber gel dispenser, that enables mixing of two precursor solutions through a microfluidic mixing channel. (C). A piston extruder-driven dual-chamber mechanical gel dispenser. (D). A single chamber dispenser with solid phase mixing tip, where a precursor solution mixes with a reagent in the solid (e.g. packed powder state) present at the tip, which upon mixing through channels at the tip, dissolves the solid, leading to chemical reaction between the contents of the solutions and the contents of the solid.

FIGS. 32A-E. Delivery of c-MSCs within collagen matrices in a rabbit cornea in vivo. (A) Fluorescein staining showing de-epithelialized stromal defect prior to treatment. (B) clinical image showing cornea 1 week after treatment with c-MSCs encapsulated within a SPAAC-crosslinked collagen gel as well as (C) fluorescein image showing complete epithelial healing over the gel. (D) OCT showing c-MSCs (speckles) within the gel filling the stromal defect. (E) IHC staining shows CK3-positive (red) multi-layered epithelialization over the gel (stained pink) with encapsulated c-MSCs (arrow). Green stain=F-actin. Scale bar 50 μm.

Figure 33:
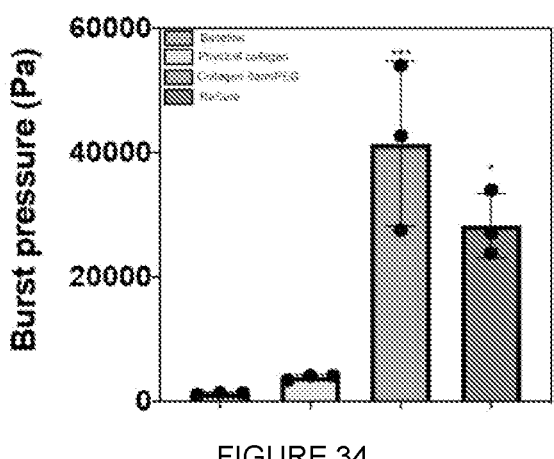

FIG. 33. Burst pressure in (Pa) after application of no hydrogel, a non-crosslinked (physical) collagen gel, a collagen-PEG gel (crosslinked by multi-arm PEG-NHS), and a commercially available sealant (ReSure) to a pig eye after perforation with a 19 gauge needle.

Figure 34:
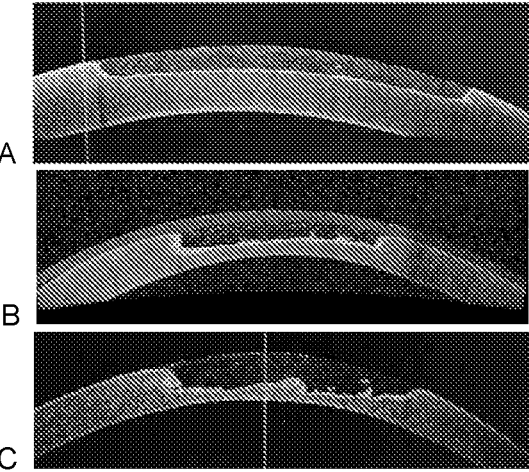

FIGS. 34A-C OCT images showing (A) a smooth lamellar stromal defect (B) with an overlying contact lens, and (C) a highly irregular stromal defect, demonstrating the restoration of normal anterior corneal curvature in all three cases using an in situ-forming gel.

DETAILED DESCRIPTION

The invention described below relates to injectable precursor compositions and methods for in-situ forming tissue constructs that find use in partial or total repair, regeneration, and/or reconstruction of wounded tissue in a mammalian subject or host organism. Other purposes of the instant disclosure include, but are not limited to, the use for effective transplantation of cells into the host organism to encourage recellularization of wounded tissue, the delivery of bioactive agents, biomolecules, and/or pharmaceutical agents (either singular or combinations of agents/molecules), and the use as a tissue model for the in-vitro study of cellular responses and interplay.

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting. Although a number of methods and materials similar or equivalent to those described herein can be used in the practice of the present invention, the preferred materials and methods are described herein.

In describing embodiments of the present invention, the following terms will be employed, and are intended to be defined as indicated below. As used in this specification and the appended claims, the singular forms "a," "an" and "the" include plural referents unless the content clearly dictates otherwise.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The practice of the present invention will employ, unless otherwise indicated, conventional methods of medicine, pharmacology, chemistry, biochemistry, molecular biology and recombinant DNA techniques, within the skill of the art. Such techniques are explained fully in the literature. See, e.g. S. S. Wong and D. M. Jameson Chemistry of Protein and Nucleic Acid Cross-Linking and Conjugation (CRC Press, 2Supnd/Sup edition, 2011): GT. Hermanson Bioconjugate Techniques (Academic Press, 3Suprd/Sup edition, 2013); B. Bowling Kanski's Clinical Ophthalmology: A Systematic Approach, 8e (Saunders Ltd., 8Supth/Sup edition. 2015); A. L. Lehninger, Biochemistry (Worth Publishers, Inc, current addition). All publications, patents and patent applications cited herein, whether supra or infra, are hereby incorporated by reference in their entireties.

As used herein, "about" or "approximately" mean within 50 percent, preferably within 20 percent, more preferably within 5 percent, of a given value or range.

A value which is "substantially different" from another value can mean that there is a statistically significant difference between the two values. Any suitable statistical method known in the art can be used to evaluate whether differences are significant or not.

"Statistically significant" difference means a significance is determined at a confidence interval of at least 90%, more preferably at a 95% confidence interval.

The terms "treatment," "treating," "treat," and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease.

The terms "reconstructing" and "reconstruction," and the like are used herein to generally refer to rebuilding, healing and regenerating an injured matter or tissue.

The term "subject" or "mammalian subject" refers to any mammalian subject for whom treatment or therapy is desired, particularly humans. "Mammal" for purposes of treatment refers to any animal classified as a mammal, including humans, domestic and farm animals, and zoo, sports, or pet animals, such as non-human primates, dogs, horses, cats, cows, sheep, goats, pigs, camels, etc. In some embodiments, the mammal is a human.

The term "therapeutically effective amount" or "effective amount" means the amount of a compound, agent, composition, construct that when administered to a mammalian subject for treatment is sufficient, in combination with another agent, or alone in one or more doses or administrations, to effect such treatment for the disease. The "therapeutically effective amount" will vary depending on the compound, agent, composition, construct, the defect or disease to be treated, and its severity and the age, weight, etc., of the mammalian subject to be treated.

As used herein, the term "cell" in the context of the in-vivo and in-vitro applications of the present invention encompasses mammalian cells of any genus or species. The types of cells that may be incorporated into the polymeric biomaterial include progenitor cells of the same type as those from the tissue site, and progenitor cells that are histologically different from those of the tissue site such as embryogenic or adult stem cells, that can act to accelerate the healing, regenerative or reconstructive process. The compositions comprising cells can be administered in the form of a solution or a suspension of the cells mixed with the polymeric biomaterial solution, such that the cells are substantially immobilized within the application site upon gelation. This serves to concentrate the effect of the cells at the site of application; and may provide for release of the cells over a course of time.

Somatic stem cells are characterized as cells with the ability to self-renew and give rise to differentiated progeny via mitosis. These adult stem cells are often found in specialized locations, or niches, in tissues throughout the body. When tissue is damaged, stem cell populations are often instrumental in replacing the lost cells to restore tissue function and integrity. Stem cells are found in many different tissues, including hematopoietic stem cells in the bone marrow, muscle, adipose tissue, skin, umbilical cord blood, neural tissue, etc. and may be isolated from tissues, or can be differentiated in vitro from pluripotent stem cells. Corneal cells may used, for example limbal epithelial stem cells, corneal stromal stem cells, keratinocytes, keratocytes, endothelial cells, etc. may be isolated, harvested, and/or propagated from cadaveric donor corneal tissue, from small limbal biopsies from patients (either autologous from one's healthy eye, or from another living patient's eye as a donation); generated by in vitro culture, etc.

In the cornea, stem cells include limbal epithelial stem cells (LESCs), which may be found at the limbal region that marks the transition zone between cornea and conjunctiva. Keratin expression is distinct in these limbal basal cells, with a lack of cytokeratins CK3 and CK12, and expression of CK14/CK59-11. The cells are also positive for adult stem cell marker ABCG2. ABCB5, a member of the ATP-binding cassette family of proteins, has also been identified as a definitive LESC marker. Expansion of limbal cells in vitro and transplantation to central cornea can restore epithelial function.

Corneal stem cells also include corneal stromal stem cells, which are quiescent, mesenchymal ceils. It has been suggested that corneal stromal stem cells are a subpopulation of stromal cells that can differentiate into keratocytes. Stromal corneal stem cells are also positive for ABCG2 expression.

For in vivo application, the polymeric compositions and cells can be mixed and then applied to the in vivo site. The cells are preferably added to the polymeric compositions immediately prior to administration to the application site to enhance survival of living cells. The cells of the thus resulting cellularized hydrogel may maintain a cellular phenotype at the site of application, which is usually the affected, i.e. damaged, area for at least one day, one week, or one month following application. Where the polymeric composition is administered in a two solution format, it can be crosslinked in situ for tissue repair or regeneration.

Therapeutically effective amounts of the cells encapsulated within a hydrogel of the instant disclosure will vary depending e.g., on the condition to be treated, typical survival of the particular cell type within the hydrogel construct (e.g., including the average lifespan of cells of the particular cell type), etc.

In some embodiments, a therapeutically effective amount of cells is $1\times10^3$ or more cells, including e.g., $5\times10^3$ or more, $1\times10^4$ or more, $5\times10^4$ or more, $1\times10^5$ or more, $5\times10^5$ or more, $1\times10^6$ or more, $5\times10^6$ or more, $1\times10^7$ or more, $5\times10^7$ or more, $1\times10^8$ or more, $5\times10^8$ or more, $1\times10^9$ or more, $5\times10^9$ or more, $1\times10^{10}$ or more, $5\times10^{10}$ or more. Alternatively, the hydrogel, following administration of the polymeric compositions and crosslinking at the site of application, can also be seeded with cells and used to repair and regenerate damaged corneal or generally ophthalmic tissue.

The defined hydrogel structure provides a three-dimensional construct for new cell growth. The hydrogels of the present invention can be used not only for the encapsulation of cells, but also for the encapsulation of other molecules and agents that may enhance proper remodeling of the crosslinked polymer so that its contents are replaced with the matrix elements native to the surrounding tissue (e.g. in the cornea, the crosslinked matrix is eventually broken down and replaced by normal corneal tissue).

As used herein, the term "under physiological conditions" encompasses those conditions that are compatible with living cells, e.g., predominantly aqueous conditions of a temperature, pH, salinity, osmolarity, osmolality etc.

The term "gel" or "hydrogel," as used herein, refers to a crosslinked network of hydrophilic biopolymers. Hydrogels of the instant disclosure will generally be made by combining a first flowable composition containing reactive groups of one nature and a second flowable composition containing reactive groups of a different nature, and possibly more flowable compositions with reactive groups of further different nature. The flowable compositions may be combined in situ, particularly where the network is covalently linked. The flowable nature of the material allows it to fill defects in tissues such as corneal stroma, and regardless of the irregularity of the underlying stroma, creates a smooth outer contour which depending on the viscosity and volume of the fluid applied, can match the surface contour of the native/normal cornea after crosslinking. This contour can be modulated by the placement of a hard or soft (or hybrid hard/soft) contact lens, where the posterior surface of the contact lens prescribes a curvature to the underlying gel within the corneal defect.

The term "biopolymer" refers to a biocompatible polymers comprising polymers that can be found naturally in organisms, as well as chemical and physical modifications of such polymers, and include, but are not limited to, proteins, fibrins, fibrinogen, collagens, collagen-like peptide, collagen-mimetic peptides, peptide sequences, gelatins, elastins, elastin-like peptides, laminin, fibronectin, extracellular matrix constituents, glycosaminoglycans, chondroitin sulfate, keratan sulfate, dermatan sulfate, heparan sulfate, hyaluronic acid, albumin, alginates, chitosans, cellulose, thrombin, heparin, polysaccharides, synthetic polyamino acids, prolamines, combinations thereof, and other such molecules.

Naturally occurring polymers include, but are not limited to, proteins and carbohydrates. The term "bio-polymer" also includes derivatised forms of the naturally occurring polymers or peptides that have been modified to facilitate cross-linking to a synthetic polymer of the invention. Additionally, the term "bio-polymer," as used herein, includes proteins produced using recombinant methodologies, such as, for example, recombinant collagen.

Combinations of biopolymers can be used, to form compositions such as an interpenetrating polymer network, semi-interpenetrating polymer networks, or copolymer networks. Combinations may be combined in different ratios, e.g. where two biopolymers are used, a ratio may be 1:50; 1:10, 1:5, 1:3, 1:2, 1:1; 2:1; 3:1; 5:1; 10:1; 50:1; etc. For example, collagen can be crosslinked in the presence of uncrosslinked hyaluronic acid and/or chondroitin sulfate to form a semi-interpenetrating polymer network of collagen and hyaluronic acid (and/or chondroitin sulfate). In another example, HA or chondroitin sulfate can be crosslinked in the presence of uncrosslinked collagen to form a semi-interpenetrating polymer network of collagen and hyaluronic acid (and/or chondroitin sulfate). In another embodiment, hyaluronic acid can be crosslinked in the presence of collagen to form a semi-interpenetrating polymer network. In another embodiment, collagen and hyaluronic acid can be crosslinked to each other to form a copolymeric network. In another embodiment, collagen and PEG can be crosslinked to each other to form a copolymeric network. In still another embodiment, collagen can be crosslinked in an independent process from the crosslinking of hyaluronic acid (either simultaneously or in sequence) to yield a fully interpenetrating polymer network.

In preparing hydrogels in accordance with the present invention, the ratio of polymers containing reactive groups of one nature and polymers containing reactive groups of a different nature to each other can range from about 0.1 to about 3.0, from about 0.7 to about 3.0, from about 1.0 to about 2.0, from about 0.1 to about 10, or from about 0.5 to about 5.0.

When used as tissue constructs in tissue engineering for replacing or restoring tissue and organ function, as contemplated herein, hydrogels of the present invention may contain mammalian cells, such as stem cells such as corneal stromal stem cells, or somatic cells such as keratocytes and keratinocytes, in order to repair tissue or to promote tissue repair, reconstruction and regeneration. The hydrogels of the present invention can be prepared with enhanced mechanical as well as structural properties and resistance to degradation, can be made visually transparent and because of their cytocompatibility support cell overgrowth, ingrowth and encapsulation of cells.

A hydrogel in accordance with the present invention comprises an assembly of polymers and is suitable for use in a variety of applications, including, but not limited to, clinical, therapeutic, prophylactic, or cosmetic applications. The hydrogel material can be used to replace, restore, and/or augment tissue and/or organ function in a mammalian subject in need thereof. Various biomedical, biotechnological, and/or pharmaceutical applications include, for example, corneal substitutes, therapeutic lenses, cell and/or drug delivery carriers, and tissue engineering scaffolds. Besides benefitting therapeutically in the treatment of a disease, disorder or traumatic injury of an eye and, and enhancing corneal regeneration and reconstruction, hydrogels in accordance with the present invention can be used in ophthalmic devices to enhance optical power or comfort.

Hydrogels that form in situ are adaptable to complicated defect sites when compared to structurally preformed hydrogels. With structures that form in situ and which are contemplated herein, two or more solutions containing the macromeric, precursor compositions of the hydrogel are injected or otherwise delivered to the site where the hydrogel is to be used and crosslinking is initiated. The precursor compositions can be manipulated and formed when the crosslinked solution is over a strain threshold. In most cases, the hydrogel does not require a catalyst to crosslink, thus avoiding biocompatibility problems. The precursor materials are substantially bioorthogonal and will crosslink in the presence of gelatins, collegens, lipids, carbohydrates or polymer nanofibers. Because of their crosslinking reaction kinetics, the hydrogels of the present invention can encapsulate and transport highly sensitive cells and other biological additives. Moreover, many of the hydrogels of the present invention have no known toxic byproducts.

Polymeric hydrogels can be defined as two- or multicomponent systems consisting of a three-dimensional network of polymer chains, and water that fills the space between macromolecules. A hydrogel is a network of polymer chains that are water-soluble, sometimes found as a colloidal gel where water is the dispersion medium. Hydrogels are superabsorbent (they can contain over 99% water) natural or synthetic polymers. Hydrogels possess also a degree of flexibility that is very similar to natural tissue, due to their considerable water content. Two general classes of hydrogels are known in the art. There are physical hydrogels, where the chains are connected by electrostatic forces, hydrogen bonds, hydrophobic interactions or chain entanglements. Physical crosslinking of polymer chains can be achieved using a variety of environmental triggers (pH, temperature, ionic strength) and a variety of physicochemical interactions (hydrophobic interactions, charge condensation, hydrogen bonding), e.g. those gels are prone to temperature changes and usually transform to polymer solutions at particular temperatures. Chemical hydrogels generally have covalent bonds linking the chains. Chemical methods include various click reactions, thiol-ene additions, metal-catalyzed azide-alkyne cycloadditions, Michael additions and Diels-Alder reactions. Metal-free, strain-promoted azide-alkyne "click" cycloaddition reactions have been applied to cell imaging as well as hydrogels systems due to its highly efficient conversion, orthogonality, and biofriendly characteristics. The gel formation process is atom neutral in that there are not residuals that contaminate the system and could pose toxicity problems to associated biological systems.

As used herein, the term "reactive group" means a molecule or molecular moiety within one composition that specifically reacts with another reactive moiety in another composition under physiological conditions and, when brought into sufficient proximity under appropriate conditions, is able to link the two molecules or moieties by a chemical bond, e.g., a covalent bond. Reactant groups of interest are usually involved in bioorthogonal chemistry, i.e. chemical reactions that can occur inside of living systems without interfering with native biochemical processes. The reaction must be selective between endogenous functional groups to avoid side reactions with biological compounds, and have to be non-toxic and must function in biological conditions taking into account pH, aqueous environments, and temperature.

In general, the methods of the invention utilize compositions of modified biopolymers that react with each other to form stable hydrogel structures. Biopolymers for these purposes have been modified by the addition of reactive groups.

In one embodiment, reactive groups are copper-free click chemistry reactants, which form covalent bonds upon mixing. See Click Chemistry: Diverse Chemical Function from a Few Good Reactions Hartmuth C. Kolb, M. G. Finn, K. Barry Sharpless Angewandte Chemie International Edition Volume 40, 2001, P. 2004, herein specifically incorporated by reference). Copper-free click chemistry is an alternative approach to traditional click chemistry that proceeds at a lower activation barrier and is free of cytotoxic transition metal catalysts. The absence of exogenous metal catalysts makes these reactions suitable for the in vivo applications. Strain-promoted alkyne-azide cycloaddition reaction (SPAAC) is a form of copper-free click chemistry that involves the reaction between an strained alkyne and an azide.

In some embodiments the biopolymers are linked to form the hydrogel structure through covalent bonds (cross-links), including without limitation through bio-orthogonal chemistries, such as chemistries based on strain-promoted azide-alkyne cycloaddition (SPAAC) and chemistries based on inverse electron demand Diels-Alder (IED-DA) reaction, as well as other "click"-type reactions such as thiol-ene reactions and hydrazone ligation. For such covalent chemistries the flowable biomaterial composition may be provided as two solutions that react and cross-link at the site of application under ambient conditions on a tissue surface without the need for an external stimulus such as light, for example see WO 2020/006255, and Madl et al., Adv. Funct. Mater. 2018, 28, 1706046, each herein specifically incorporated by reference.

Other click chemistry reactions of interest include, for example, the use of copper-catalyzed azide-alkyne cycloaddition reaction (CuAAC) in applications where the toxicity of copper is not important. Alternatively the inverse-demand Diels Alder ligation pair trans-cyclooctene-tetrazine (TCO-Tz) may be used. The chemoselective TCO-Tz ligation pairs possess ultrafast kinetics ($>800$ $M^{1}s^{-1}$), selectivity, and long-term aqueous stability are advantages of TCO-Tz.

Other bio-orthogonal chemistries include, but are not limited to 1,3 dipolar cycloadditions, copper-catalyzed azide-alkyne cycloaddition reactions, Diels-Alder, inverse-electron demand Diels-Alder, Staudinger ligation, and nitrile oxide cycloaddition (see Madl/Heilshorn review in Adv Functional Materials page 4). In some cases, such as copper-catalyzed azide-alkyne cycloaddition reactions, a chelating agent may be needed to address and remove free copper ions. Other "click" type chemistries that can also be used in this invention include conjugate addition such as thiol-maleimide, thiol vinyl-sulfone, photomediated thiol-ene, hydrazone bonds, oxime ligation, and maleimide-furan Diels-Alder.

In such an embodiment, biopolymers, which may be the same or different, are modified to comprise reactive groups, where a first reactive group is an azide group and a second reactive group is a cycloalkyne group. The reacting, i.e. contacting, step results in a reaction between the azide group of the azide-modified biopolymer and the cycloalkyne group of the cycloalkyne-modified biopolymer, thereby synthetically and covalently modifying both biomolecules so that a hydrogel forms in-situ, i.e. at the site where the contacting occurs, upon the reacting step. Reactive groups of interest, include, but are not limited to, thiols, alkyne, a cyclooctyne, an azide, a phosphine, a maleimide, an alkoxy amine, an aldehyde, a thiol, a methacrylate or acrylate, and protected versions thereof, and precursors thereof.

When two different biomolecules are used as conjugated pairs, for instance, if collagen is azide-modified, and HA is alkyne-modified (or vice-versa), when they are mixed, a covalently crosslinked co-polymer network of collagen and HA is formed through SPAAC-mediated linkages between the pendant azides and alkynes. Biomolecules may also be crosslinked with non-biological macromolecules such as PEG and multi-arm PEG, with compatible end groups. For instance, an azide-modified collagen can be crosslinked with a multi-arm PEG with alkyne endgroups (e.g. BCN or DBCO). In another example, an alkyne-modified collagen can be crosslinked with a multi-arm PEG with azide endgroups. The multi-arm PEG may have two, three, four, or more arms, including 8 arms, with some or all of the end groups being functionalized with a moiety that promotes chemical crosslinking with SPAAC. The multi-arm PEG may have two, three, four, or more arms, including 8 arms, with some or all of the end groups being functionalized with a moiety that promotes cross-linking. More than 8 arms may be used as well, for instance to dendrimeric-type polymers with multiple arms and branches.

Interpenetrating polymer networks can be formed, where one network is crosslinked via bioorthogonal crosslinking chemistry (e.g. SPAAC, Diels Alder, inverse electron demand Diels Alder, etc.) while the other is formed via another chemistry. The two networks can be formed by two different bio-orthogonal reactions (e.g. SPAAC and inverse electron demand Diels Alder). Semi-interpenetrating polymer networks can also be formed where one species is not crosslinked at all, such in a case where an HA network is formed by chemical crosslinks around a solution of linear/uncrosslinked collagen. Similar, a collagen network can be formed by chemical crosslinks around a solution of linear/uncrosslinked HA.

In one embodiment an in-situ forming tissue construct i.e. a defined hydrogel structure, is formed by combining reactants at the tissue site for covalent cross-linking, for example by copper-free click chemistry. For example, a first composition comprising a biopolymer that is functionalized with azide reactive groups, and a second composition comprising a biopolymer that is functionalized with alkyne reactive groups, such as dibenzocyclooctyne (DBCO) or bicyclooctyne, are combined. Upon consecutive or simultaneous administration to the desired site, e.g. a corneal area, and direct contacting of each other, the reactants undergo cross-linking and gelation via strain-promoted azide-alkyne cycloaddition (SPAAC), to form a defined hydrogel structure, on the site in situ, wherein the defined hydrogel structure is effective in treating or reconstructing the wounded area. Azide groups and/or alkyne groups are optionally attached to biopolymers through a spacer arm, e.g. polyethylene glycol. In other embodiments, these groups comprise the end-functionality of PEG molecules with two or more arms (e.g. 3 or 4 or more arms), e.g. through NHS chemistry. Non-limiting examples include a collagen solution combined with multi-arm PEG-NHS solution, which forms a covalently linked hydrogel.

The term "biocompatible" refers to the absence of stimulation of a severe or escalating biological response towards administration of a composition, and is distinguished from a mild, transient inflammation which typically accompanies surgery or implantation of foreign objects into a living organism.

The term "polymer," as used herein, refers to a molecule consisting of individual monomers joined together. Polymers that are contemplated herein can be naturally occurring, synthetically produced, or produced using recombinant methodologies.

The term "transparent," as used herein, refers to at least 70%, 80, or 90% transmission of white light.

The term "DBCO," as used herein means a strained cyclooctyne molecule dibenzylcyclooctyne.

The term "BCN," as used herein in means a strained cyclooctyne molecule, bicyclo[6.1.0]nonyne.

Polyethylene glycol chains of various lengths can be used as spacers within the functionalization process, wherein the first end of the polyethylene glycol chain is covalently linked on one side to a reactive group (or groups), as defined herein, including a PEG azide or a monofunctional or PEG cyclooctyne.

Precursor Compositions that In Situ Gelate and Form Tissue Constructs Upon Cross-Linking Using bioconjugation methodologies including bioorthogonal copper-free click chemistry methods such as the Strain Promoted Azide Alkyne Cycloaddition (SPAAC), tissue constructs may be formed in-situ, meaning at the site of application which is usually the site of injury, wound or defect, by reactions between at least two (a "first" and a "second") polymeric "precursor" compositions. Those precursor compositions are functionalized with reactive groups as described herein, which include without limitation multiple azide reactive groups in a first composition and with multiple alkyne reactive groups in a second composition. The precursor groups may be separately administered to the site of issue injury, wound or defect. Reaction of the groups results in gelation of the combined precursor compositions to form a defined hydrogel composition at the site of injury, wound or defect. Spacers comprising polyethylene glycol (PEG) in various lengths may be used in the functionalization process. Such polymeric precursor compositions are typically flowable biomaterials.

The precursor compositions of the present invention encompass biocompatible biopolymers such as collagen that can be functionalized with reactive groups and that form hydrogels in situ upon reaction. Such in-situ gelling compositions that are functionalized with different reactive groups are applied to a site of injury, wound or damage, for example to the site of a corneal defect, and undergo a sol-gel (liquid to solid) transformation at the site of the injury, wound or defect, and so form a tissue construct upon the site of injury, wound or defect.

The pharmaceutically acceptable excipients, such as vehicles, adjuvants, carriers or diluents, are readily available. Moreover, pharmaceutically acceptable auxiliary substances, such as pH adjusting and buffering agents, tonicity adjusting agents, stabilizers, wetting agents and the like, are readily available.

Polymers contemplated for use in the instant disclosure as exemplary hydrogel-forming molecules include glycoproteins, carbohydrates, and other macromolecules, including, but not limited to, various types of collagen, proteins, fibrins, fibrinogen, collagens, gelatins, elastins, laminin, fibronectin, extracellular matrix constituents, glycosaminoglycans, hylauronic acid, albumin, alginates, chitosans, cellulose, thrombin, heparin, polysaccharides, synthetic polyamino acids, prolamines, hydroxy methylcellulose, chitosan, combinations thereof, and other such molecules, including recombinant versions of such polymers.

Collagen, a widely used biomaterial for producing tissue scaffolds and constructs, is the major constituent of the extracellular matrix, and has been used as wound dressing, corneal shields, and engineered corneal matrix. It is well known that collagen's molecular structure plays a crucial role in cell adhesion, migration, and differentiation.

In various embodiments of the present invention in order to demonstrate the utility of the described precursor compositions to form in-situ a tissue construct at the site of a corneal defect, bovine type-I collagen was employed as matrix due to its low immunogenicity compared to other collagen types. Collagen type I is commonly used as a cellular scaffold in three-dimensional cell culture because collagen gel matrices are more similar to the native cell environment than general two-dimensional cell culture dishes. When an acidic collagen solution is neutralized and incubated at 20-37° C., the collagen forms a gel through fibril formation. However, collagen extracted from tissue loses its original fibril density and three dimensional architecture, and as a result, neutralized non-covalently cross-linked collagen gels have low mechanical strength.

The physical properties of collagen can be modulated by crosslinking techniques that enhance mechanical strength, enzymatic degradation resistance, and transparency. For example, transparency of crosslinked biomaterials such as SPAAC-crosslinked collagen gels is an important aspect for their usefulness in corneal applications. Whereas physically collagen gels exhibit optical turbidity in proportion to the degree of randomly organized fibrillar structures in the collagen, crosslinked gels are optically clear because of the presumably reduced random organization of fibrillar structures through crosslinking.

Hyaluronic acid is another polymer of interest, which may be used alone or in combination with collagen. It is a polymer of disaccharides, themselves composed of D-glu-curonic acid and N-acetyl-D-glucosamine, linked via alternating $\beta$-(1→4) and $\beta$-(1→3) glycosidic bonds. Polymers of hyaluronic acid can range in size from 5,000 to 20,000,000 Da in vivo. The average molecular weight in human synovial fluid is 3-4 million Da, and hyaluronic acid purified from human umbilical cord is 3,140,000 Da. Hyaluronic acid is energetically stable, in part because of the stereochemistry of its component disaccharides. Bulky groups on each sugar molecule are in sterically favored positions, whereas the smaller hydrogens assume the less-favorable axial positions.

Cellularized or Acellular Compositions

Figure 32:
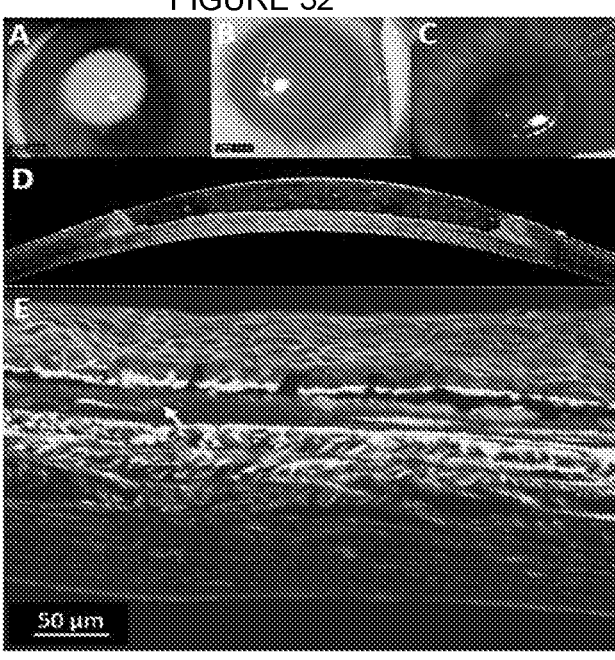

In some applications, the gel (with or without cells) are applied to tissues such as the eye using a handheld dispenser that administers a controlled volume of reacted and admixed precursor solutions to form the gel on the site of interest (e.g. a corneal wound). Examples of such handheld dispensers are shown in FIG. 32.

For each type of tissue being replaced, the flowable biomaterial compositions can be injected with cells, i.e. cellularized, or without cells, i.e. acellular. Such cells can be somatic/differentiated cells, induced pluripotent stem cells, or progenitor/stem cells.

The in-situ encapsulation of corneal keratocytes within gels to support corneal re-epithelialization was investigated in SPAAC-crosslinked versus non-covalently crosslinked gels. To mimic the structure of the cornea which is composed of a multi-layered epithelium of keratinocytes overlying a stromal layer of collagen type I and keratocytes, keratinocytes were cultured on collagen gels with encapsulated keratocytes, whereby the collagen was either crosslinked by SPAAC or without additional covalent crosslinking. Cell behavior, phenotype, and cytocompatibility of encapsulated keratocytes were evaluated as a function of crosslinking and mechanical properties. Corneal keratinocytes were cultured on the SPAAC-crosslinked gel and were able to adhere and migrate over the surface (shown in FIG. 1)

All collagen gels were cytocompatible with both cell types, but the cells showed different phenotypic behavior depending on the type of gel. SPAAC-crosslinked gels supported a more favorable and stable keratinocyte morphology on their surface than non-crosslinked gels likely as a result of more optimal substrate stiffness, gel integrity, and resistance to degradation.

As described herein, such in-situ formed constructs or scaffolds are able to support a co-culture of keratocytes within their matrix and keratinocytes on their surface, and can be provided as cellular or acellular lamellar substitutes to facilitate multilayered re-epithelialization of wounded corneal stromal tissue. In addition, such scaffolds provide a three-dimensional in-vitro model system for studying keratocyte-keratinocytes interactions within corneal tissue.

Crosslinking Via Strain-Promoted Azide-Alkyne Cycloaddition (SPAAC)

In one embodiment of the invention, a bio-orthogonal approach based on bioorthogonal chemistry, that can make highly specific covalent bonds without interfering with cells and biomolecules in a living system, is used to crosslink biopolymer matrices with strain-promoted azide-alkyne cycloaddition for encapsulating cells or for carrying out reactions on ocular wound sites including corneal defects. Strain-promoted azide-alkyne cycloaddition (SPAAC) is a bio-orthogonal, copper-free form of click chemistry and suitable to chemically crosslink polymer or biopolymers such as collagen around cultured cells, including corneal stromal stem cells or keratocytes (in-situ encapsulation). SPAAC can be used to form covalent bonds between biomolecules in the presence of living cells.

To facilitate strain-promoted azide-alkyne cycloaddition (SPAAC) mediated crosslinking in embodiments of the present invention, collagen was functionalized with either azide or dibenzocyclooctyne (DBCO) reactive groups using N-hydroxysuccinimide (NHS) coupling chemistry. A poly (ethylene glycol) (PEG) spacer was introduced in the azide group conjugation to allow for enhanced conjugation efficiency.

In contrast to commonly used chemical crosslinking agents such as glutaraldehyde, carbodiimide, and N-hydroxysuccinimide (NHS) which may be cytotoxic due to unselective reactions with cells, azides and alkynes do not react with functional groups present on cells and tissues, and only proceed with the cycloaddition reaction when they encounter each other. SPAAC reaction produces no free radicals and side products, can proceed in water under ambient conditions without the need for external catalysts such as an initiator or copper, and do not need for a trigger such as light or heat.

SPAAC can be performed under ambient conditions in aqueous solution without the need for solvents or catalysts, produces no side reactions or free radicals or side products, and does not react with surrounding cells, proteins, or tissue. Because of these numerous advantages, SPAAC was used in the various embodiments of the present invention to crosslink collagen and encapsulate cells.

Methods

In some aspects of the invention, methods are provided for treating an injury, wound or defect that requires tissue regeneration, tissue replacement or repair, regeneration, and/or reconstruction of ocular, skin, subcutaneous tissue, nerve, muscle, bone, cartilage, vitreous, tendon, ligament, fat, retinal, conjunctival, scleral, cardiac, adrenal, and other types of tissue. In these methods, flowable biomaterials are applied to a site of injury, wound or defect where, upon crosslinking of reactive groups, a defined hydrogel structure tissue construct is formed in-situ on top of the injury, wound or defect, which serves to regenerate, reconstruct and repair the tissue injury, wound, or defect. For instance, in one embodiment of the invention, the gel is applied to the peripheral part of the ocular surface in an area devoid of conjunctival tissue, and acts as a scaffold for overgrowth by surrounding conjunctiva. In other embodiments, the gel is applied in conjunction with admixed conjunctival cells to repopulate an area that is devoid of conjunctival cells.

Utility

The injectable flowable biomaterial compositions and methods of the present invention can be applied to any clinical situation where tissue engineering, regeneration or reconstruction in a mammalian host or subject is necessary. Tissue engineering is a rapidly growing field encompassing a number of technologies aimed at replacing or restoring tissue and organ function. The key objective in tissue engineering is the regeneration of a defective tissue through the use of materials that can integrate into the existing tissue so as to restore normal tissue function. Such injectable compositions can comprise cells that settle in the host and encourage recellularization of the wounded tissue. Furthermore, such injectable compositions can also serve as a three-dimensional tissue model for the in-vitro study of cellular responses and interplay.

Application as In-Situ Forming Hydrogel Upon Ocular Defects

To address an unfilled need for effective compositions and methodologies to treat and regenerate ocular defects, including corneal defects, precursor compositions are described in various examples herein that upon crosslinking form in-situ corneal constructs on top of corneal defects. Such ocular and corneal defects may be caused by, e.g., neurotrophic keratopathy, recurrent corneal erosion, corneal ulcer, corneal burns, exposure keratopathy, physical trauma, retinal disease, retinal degeneration, optic nerve damage, optic nerve degeneration, and other disorders.

The cornea is a highly specialized transparent tissue and, as the most anterior ocular tissue, protects the eye by acting as a physical barrier. It is comprised of three cellular layers: the outer layer being the stratified squamous corneal epithelium, the center layer being the corneal stroma, and the inner layer being the corneal endothelium. The corneal stroma makes up the majority of the corneal tissue. The extracellular matrix (ECM) of the corneal stroma has a lamellar, highly organized structure that facilitates the transparency of the cornea, whereby each lamella is composed of tightly organized collagen fibrils. Keratocytes are mesenchymal-derived cells that are quiescent in the mature cornea and that are arranged within the corneal stroma. Upon injury to the cornea, the keratocytes become activated, and several changes in the corneal stroma occur. Upon an initial apoptotic phase, keratocytes lose their quiescence, start to divide and develop either into phenotypes that start to secrete extracellular matrix for corneal regeneration or into phenotypes that induce fibrotic scar formation at the site of injury. Unlike in uninjured stromal tissue, the extracellular matrix in scar tissue is disorganized and opaque, and may seriously impair visual acuity and lead to blindness.

Delivering (cultured) cells such as corneal stromal stem cells (CSSCs) or keratocytes to the site of corneal injury may minimize the fibrotic response and enhance the regeneration of the corneal tissue. Delivery of corneal cells, such as keratocytes and keratinocytes, and other cells, within injectable polymeric precursor compositions that gel in-situ upon cross-linking, as described herein, may be instrumental in repairing and regenerating corneal tissue. The cells can then be encapsulated into the corneal construct to provide a scaffold for proliferation and reepithelialization of the corneal defect.

Such compositions may comprise functionalized biopolymers such as collagen (type I) that are crosslinked in situ, and where the crosslinking transforms the injectable precursor compositions into a substantially transparent hydrogel that serves as a corneal stromal scaffold, substitute or construct on top of a corneal or stromal defect, wound or wounded area to enhance the regenerative capacity of the cornea to restore viable corneal tissue.

Such polymer-based precursor compositions, when functionalized with azide-alkyne crosslinking agents and which can additionally contain a suspension of corneal keratocytes to aid in the reepithelization of the wounded corneal area, are consecutively applied as flowable precursor compositions to a wounded corneal area, and then gelated on the spot (in situ) by SPAAC crosslinking to produce an in situ-forming corneal stromal scaffold which is kept in place on top of the wound site. The in situ-formed scaffold mimics the thickness and smooth, continuous surface of the cornea.

In examples described herein, the polymer-based composition was collagen that was modified with azide and dibenzocyclooctyne (DBCO) or bicyclooctyne (BCN) groups to enable the SPAAC reaction between azide-conjugated collagen and alkyne-conjugated (DBCO-conjugated or BCN-conjugated) collagen. An equivalent ratio between azide and cyclooctyne groups led to high efficiency in collagen crosslinking with increasing modulus. The ratios and concentrations of conjugated collagens were adjusted to obtain a range of mechanical properties of the resulting collagen gels.

The in situ forming gels when applied to a wound site can further contain and encapsulate other elements, including but not limited to cells (to act as a vehicle for cell transplantation), the secretions of cells, biomolecules, growth factors, drugs, fibers (such as electrospun fibers) that provide additional mechanical reinforcement. Furthermore, the gels can be formed outside of the body and then processed further (e.g. via vitrification), and then placed on or within a wound and secured either by the application of additional in situ forming gel, another adhesive material (such as tissue glue or sealant), sutures, or some combination of these.

Exemplary therapeutic factors that can be used include growth factors, such as epidermal growth factor (EGF), nerve growth factor (NGF), fibroblast growth factor (FGF), vascular endothelial growth factor (VEGF), and insulin-like growth factor (IGF); hepatocyte growth factor (HGF), keratinocyte growth factor (KGF), insulin-like growth factors (IGF), nerve growth factor (NGF), and their derivatives, as well as other biomolecules with pro-regenerative effects such as thymosin beta 4, neuropeptides, such as substance P (SP) and calcitonin gene-related peptide; extracellular matrix proteins, such as fibronectin, collagen, laminin, and fibrin; axon guidance proteins, such as netrins (e.g., netrin-1), ephrins, and cell adhesion molecules; and other biomolecules that play various roles in tissue regeneration, such as beta-thymosins (e.g., thymosin beta-4). Other types of molecules or biomolecules may also be used, such as anti-vascular endothelial growth factor (anti-VEGF) therapeutic agents to prevent vascularization, leakage, or growth. Anti-VEGF therapeutic agents (e.g., bevacizumab and ranibizumab) may be useful, for example, in the treatment of certain cancers or proliferative conditions, including wet macular degeneration or diabetic retinopathy. Additionally, therapeutic factors may include antibiotic agents, for example, anti-viral, anti-fungal, and anti-protozoal agents, antifibrotic agents, anti-inflammatory agents (steroids and non-steroidal agents), chemotherapeutic (anti-oncologic) agents, anti-angiogenic agents, or anti-thrombotic agents, and pro-thrombotic agents.

In-Situ Molding

In embodiments of the present invention, the crosslinked gel can be applied with or without cells, and with or without an overlying contact lens (hard or soft lens) which can be used as an in situ mold to create the desired contour and curvature of the crosslinked gel on the ocular surface. This in situ molding process may be important for bestowing the desired refractive power to the surface of the cornea, since the air-cornea interface is responsible for most of the refractive power of the eye. By providing a smooth, transparent, and properly curved surface to the central cornea, the gel can restore vision to patients whose vision was severely compromised by a central defect or ulcer. Furthermore, the gel can be applied to any part of the cornea (central, paracentral, or peripheral cornea), and can be used to encapsulate stromal cells, epithelial cells, limbal cells, or combinations thereof. In other embodiments, the eyelids can be sutured shut (i.e. tarsorraphy can be placed) completely or partially to create a protective environment for the eye after the gel is placed. This can be done with or without a contact lens in place over the cornea and applied gel.

Application as In-Situ Forming Hydrogel Upon Other Defects

The compositions and methods of the present invention can be configured to a range of applications to facilitate tissue regeneration (e.g., bone or muscle formation) or to replace tissues such as adipose tissue (e.g., in cosmetic or reconstructive surgeries), blood vessels and valves (e.g., in angioplasty, vessel inflammation, or valve deterioration), or skin (e.g., in cases of skin damage due to heat, mechanical force or by disease). As such, the compositions and methods of the present invention find use for the repair, regeneration, and/or reconstruction of skin, subcutaneous tissue, nerve, muscle, bone, cartilage, vitreous, tendon, ligament, fat, retinal, conjunctival, scleral, cardiac, adrenal, and other types of tissue. Such repair, regeneration, and/or reconstruction may also be necessary following injuries that may be associated with or result from ischemia, infections, inflammations, auto-immune reactions, organ failures, fibrosis, periodontal diseases, and can concern tissues of solid organs, e.g., kidney, liver, large intestine, small intestine, skeletal muscle, heart, pancreas, lung.

Kits

The present invention also provides kits comprising separate containers holding compositions comprising polymers, such as collagen, hyaluronic acid, etc., that are functionalized with azide groups, and polymers that are functionalized with alkyne groups, and optionally with spacer arm(s) bridging the azide or alkyne groups to the polymer, and optionally admixed with living cells or biomolecules (e.g. proteins) or pharmaceutical agents or combinations thereof to be delivered to the wounded tissue site.

Compositions can be in liquid form or can be lyophilized. Suitable containers for the compositions include, for example, bottles, vials, syringes, and test tubes. Containers can be formed from a variety of materials, including glass or plastic.

The kit can further comprise a container comprising pharmaceutically acceptable excipients or formulating solutions such as buffers, diluents, filters, needles, and syringes or other delivery devices. The kit can also comprise a package insert containing written instructions describing methods for care of a corneal wound as described herein.

Administration

The precursor flowable biomaterial compositions of the present invention can be administered in the form of pharmaceutical compositions, comprising an isotonic excipient prepared under sufficiently sterile conditions for administration to a mammalian subject, particularly to a human being. In certain embodiments, multiple cycles of treatment may be administered by repeatedly applying the precursor compositions to the site of injury, wound or defect for a time period sufficient to effect at least a partial healing of the injury, wound or defect, or, preferably, for a time period sufficient to effect a complete healing of the injury, wound or defect.

EXAMPLES

The present invention is based on the discovery that bioorthogonal strain-promoted azide-alkyne cycloaddition (SPAAC) crosslinking is useful in producing in situ-forming (collagen) corneal stromal substitutes and constructs, such as crosslinked collagen gels, that may find application in-vivo in treating and reconstructing a surgically incised or wounded cornea in a mammalian subject, and in-vitro in studying keratocyte-keratinocyte interactions.

The following examples are put forth so as to provide those of ordinary skill in the art with a complete disclosure and description of how to make and use the present invention. The examples are offered for illustrative purposes only, and are not intended to limit the scope of what the inventors regard as their invention.

Reasonable efforts have been made to ensure accuracy with respect to numbers used, e.g. in the context of temperature, amount and such, but some experimental errors and deviations should be accounted for. Unless indicated otherwise, parts are parts by weight, molecular weight is average molecular weight, temperature is in degree Celsius, and pressure is at or near atmospheric. Standard abbreviations may be used throughout the specification, e.g. s or sec for second(s), min for minute(s), h or hr for hour(s), aa for amino acid(s), nt for nucleotide(s), kb for kilobase(s), i.v. for intravenous(ly), and the like.

Example 1

Simultaneous Interpenetrating Polymer Network of Collagen and Hyaluronic Acid as an In Situ-Forming Corneal Defect Filler Timely treatment for partial corneal injury and scarring can avoid corneal blindness and corneal transplantation. This work described a hydrogel that can fill corneal defects and assist the corneal regeneration. This hydrogel is a simultaneous interpenetrating polymer network (IPN) composed of collagen crosslinked via strain-promoted azide-alkyne cycloaddition (SPAAC) reaction and hyaluronic acid crosslinked via thiol-ene Michael click reaction. We compared the gelling time, strength, transmittance, and refractive index of the IPN gel to the collagen gel, hyaluronic acid gel, and semi-IPN gel. The IPN combined the advantages of collagen and hyaluronic acid gels and showed a great capacity for supporting corneal epithelial cell growth on its surface. When applied to corneal stromal defects in vivo, the IPN avoided epithelial hyperplasia, decreased stromal myofibroblasts formation, and increased the tight junction in the regenerated epithelium.

In this paper, we report on the development and characterization of a simultaneous (one-pot) interpenetrating polymer network (IPN) hydrogel of hyaluronic acid (HA) and collagen and evaluate its potential as corneal defect filler. HA and collagen were chosen because they are natural macromolecules and are key components of mammalian connective tissues. HA is a linear polysaccharide that has been widely used in ophthalmic surgery, arthritis treatment, scaffolds for wound healing, dermal filling, and tissue augmentation. Its chemical modifications, processing, polymerization, and bio-applications have been intensively investigated. With its robust track record of clinical use, HA is an excellent candidate for implant materials to fill corneal defects by virtue of its versatility, excellent transparency, and biocompatibility. It has been investigated extensively for its capacity to facilitate corneal re-epithelialization, downregulate inflammatory cytokines, and upregulate repair factors.

Collagen has been broadly used in medicine such as bioprosthetic implants, vascular grafts, wound dressings, nerve regeneration, plastic surgery, and drug delivery. Collagen type I is the primary extracellular matrix component of the corneal stroma. Various forms of collagen have been studied extensively as a scaffold material for tissue regeneration. For example, human collagen type Ill-based implants have been reported to improve visual functions of patients with ulcerated or scarred corneas caused by severe infections. A collagen derivative, gelatin, has also shown great promise as a structural component of photocrosslinkable hydrogels, facilitating stromal regeneration and corneal re-epithelialization. We previously reported on the development collagen type I hydrogels crosslinked via strain-promoted azide-alkyne cycloaddition (SPAAC) reaction and demonstrated their capacity to support multi-layered corneal epithelial cell growth.

Figure 1:
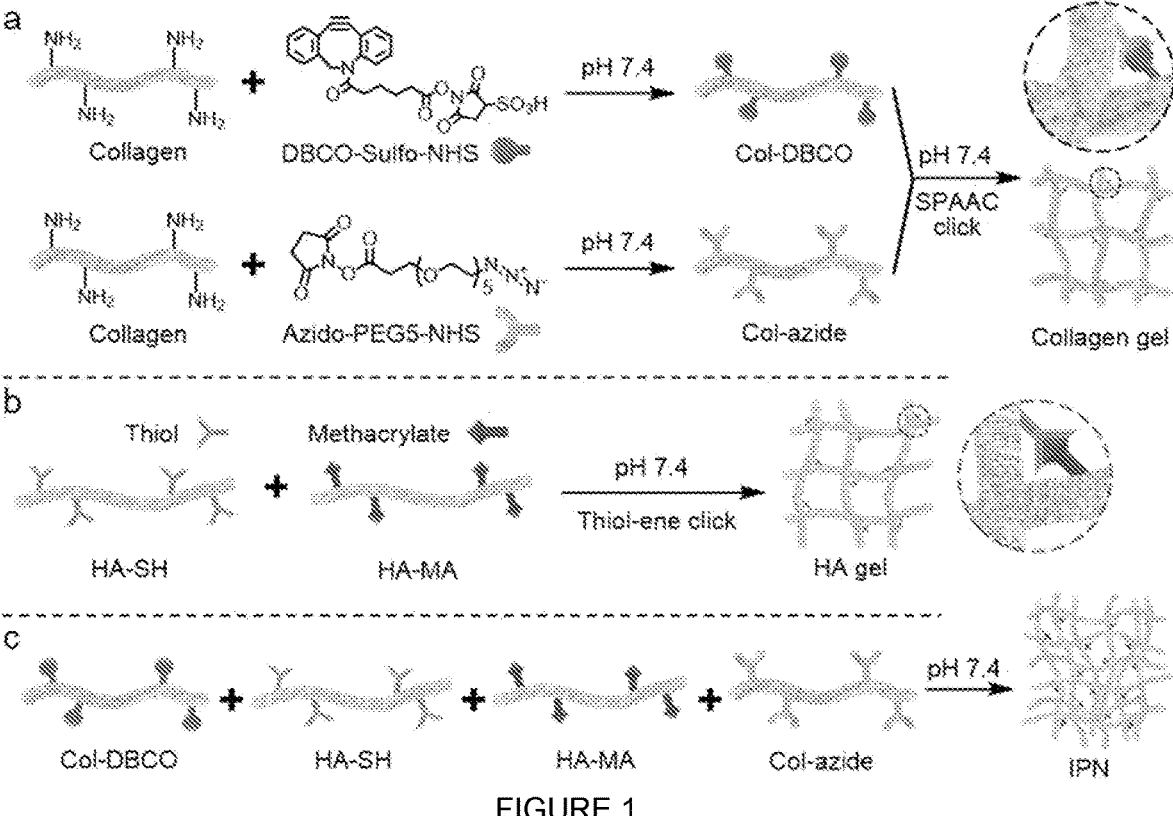
FIG. 1 Formation of hyaluronic acid (HA) and collagen based interpenetrating polymer network (IPN). (a) Collagen was modified with dibenzocyclooctyne-sulfo-N-hydroxysuccinimidyl ester (DBCO-sulfo-NHS) and azido-poly (ethylene glycol)5-N-hydroxysuccinimidyl ester (azido-PEG5-NHS) respectively. Modified collagens were then mixed and crosslinked via the bio-orthogonal strain-promoted azide-alkyne cycloaddition (SPAAC) under physiological conditions. Collagen SPAAC click gel is denoted as xCol. (b) HA thiol-ene gel (xHA) was formed by crosslinking thiolated HA (HA-SH) and methacrylated HA (HA-MA) via thiol-ene click reaction under physiological condition. (c) DBCO-modified collagen, thiolated HA, methacrylated HA, and azido-modified collagen were mixed in order to form IPN under physiological conditions.

Here, to combined the advantageous properties of collagen and HA in a single in situ-forming construct, we have developed an HA-collagen hydrogel by creating a simultaneous interpenetrating polymer network (IPN) of independently crosslinked HA and collagen without chemical bonding between the two networks. IPNs are able to take on the characteristics of each of their component polymer networks. In this work, we show that the HA-collagen IPN hydrogel has certain advantages over HA and collagen alone by combining the cell adhesion properties of the collagen network while being mechanically strengthened by the presence of the crosslinked HA network. The IPN is formed under physiological condition by mixing thiolated HA (HA-SH), methacrylated HA (HA-MA), azido-modified collagen (Col-azide), and DBCO-modified collagen (Col-DBCO) at the same time (FIG. 1). Of note, both networks of the IPN are formed simultaneously within the mixture, rather than sequentially as many IPNs reported in the literature are synthesized. Moreover, this IPN is formed in situ without the need for an external energy source such as light, heat, or a chemical catalyst such as copper or initiator. We studied the morphology, strength, gelation time, transparency, refractive index, and biocompatibility of the IPN. We also studied the potential of the IPN as an in situ-forming corneal stromal defect filler in a rabbit stromal defect model.

Methods

Materials. Dibenzocyclooctyne-sulfo-N-hydroxysuccinimidyl ester (DBCO-sulfo-NHS), dimethyl sulfoxide (DMSO), sodium hydroxide, agarose, insulin, Triton-X, trypan blue solution, and resazurin based in vitro toxicology assay kit were purchased from Sigma-Aldrich (St. Louis, MO, USA). Phosphate-buffered saline (PBS), collagen I bovine protein solution (5 mg mL$^{-1}$), epidermal growth factor (EGF) recombinant human protein, fetal bovine serum (FBS), keratinocyte-serum free media (KSFM), bovine pyruvate extract (BPE), ITS Premix Universal Culture Supplement, trypsin, live/dead viability/cytotoxicity staining kit, paraformaldehyde (PFA), 5% normal goat serum, Alexa Fluor Phalloidin 488, Alexa Fluor 647-N-hydroxysuccinimidyl ester, Slide-A-Lyzer™ Dialysis Cassette and Alexa Fluor 546 secondary antibody were purchased from Thermo Fisher Scientific (Waltham, MA, USA). Azido-poly(ethylene glycol)5-N-hydroxysuccinimidyl ester (azido-PEG5-NHS) was purchased from BroadPharm (San Diego, CA, USA). Thiolated hyaluronic acid (HA-SH) and methacrylated hyaluronic acid (HA-MA) were purchased from Blafar Ltd (Dublin, Ireland).

Hydrogel Synthesis. Collagen SPAAC-crosslinked gels (xCol) were synthesized according to our previous publication. First, type I bovine collagen was conjugated with either DBCO or azido. Briefly, type I bovine collagen was pH neutralized using a solution that consists of 1.0 M sodium hydroxide solution, distilled deionized water, and 10×PBS at a 3:57:20 ratio. The neutralization solution was mixed with 5 mg/ml type I bovine collagen at a 3:2 ratio to yield 0.3% neutralized collagen solution. Then, 8.52 μL of 100 mg/mL DBCO-sulfo-NHS/PBS was added to 1 mL of the neutralized collagen solution. The mixture was rotated at 4° C. for 2 hours. To make collagen-azide, 6.92 μL 100 mg/mL azido-PEG5-NHS in DMSO was quickly mixed with 1 mL of the neutralized collagen. The mixture was rotated for 2 hours at 4° C. and then dialyzed overnight. For fluorescent collagen-azide, the mixture was rotated for another 2 hours at 4° C. after adding 8.33 μg of Alexa Fluor 647-N-hydroxysuccinimidyl ester before dialysis. To form the 0.3% xCol, the as-synthesized Col-DBCO and Col-azide were mixed at 1:1 (v:v) ratio directly under room temperature. To form the 0.15% xCol, Col-DBCO and Col-azide were diluted with PBS to 0.15% first. Noteworthy, both Col-DBCO and Col-azide should be made freshly to form xCol.

HA thiol-ene gel (xHA) were made with commercially available HA-SH and HA-MA. Lyophilized HA-SH and HA-MA powders were rehydrated with 7.13×PBS containing 0.0395M sodium hydroxide to 5%. The rehydrated HA-SH and HA-MA were mixed at 1:1 (v:v) ratio to form 5% xHA. To make 2.5% xHA, the HA-SH and HA-MA were diluted with PBS to 2.5% respectively and then mixed at 1:1 (v:v) ratio.

To make the semi-IPN, we mixed freshly made neutralized collagen (0.3%), HA-SH (5%), and HA-MA (5%) solutions at 2:1:1 ratio. The gelling was happened under room temperature without any other catalyst or initiators.

The IPN was made by mixing freshly made Col-azide (0.3%), HA-MA (5%), HA-SH (5%), and Col-DBCO (0.3%) solutions at 1:1:1:1 ratio in order. The mixture was left at ambient environment to form IPN gel without any other catalysts or initiators.

Hydrogel Characterization. The rheological properties of the gels were measured with an ARES-G2 rheometer (TA Instruments, New Castle, DE, USA). In situ rheology of 0.15% xCol, 5% xHA, semi-IPN, and IPN were measured with a 25 mm parallel plate. Time sweeps were measured under 1% strain and 1 Hz oscillatory frequency at 25° C. until the storage modulus plateaued. Frequency sweeps were performed under 1% strain with an oscillatory frequency from 0.1 to 10 Hz at 25° C. A solvent trap was used during all rheological measurements to prevent samples from dehydrating.

The morphology of the hydrogels was examined with scanning electron microscopy (SEM) (Apreo S LoVac, Thermo Fisher Scientific). The hydrogels were flash-frozen by dipping into a liquid nitrogen tank and then lyophilized immediately. The lyophilized gels were pasted on top of SEM sample holder with silver paste. To increase the conductivity, all samples were sputter-coated with Au/Pd at a 60:40 ratio. The samples were imaged with SEM at 5 kV and 13 pA.

The transmittance of the hydrogels was determined by measuring the absorbance and then calculating with the equation: Transmittance (%)=$1/10^4 \times 100$, where A represents the measured absorbance. To measure the absorbance, 100 μL of the gels were fabricated in a standard 96-well plate and then scanned with a Tecan Microplate Reader between the wavelengths of 200 nm to 1000 nm. The same volume of double-distilled water was used as a blank. The absorbance was measured on days 0, 1, 3, and 10. The gels were sealed with a parafilm and stored in the cold room to prevent from dehydration during this period.

The refractive index of the hydrogels was recorded using a digital refractometer (HI96800, Hanna Instruments). Double distilled water was used to calibrate the device, and all measurements were normalized to 20° C. The surface focal power (Ds) of the hydrogels was determined using the equation $Ds=(n-1)/r$, where n represents the measured refractive index and r represents the radius of curvature. For humans, the radius of curvature is approximately 8 mm.

Cell Culture and Biocompatibility. Corneal epithelial cells (ATCC® CRL-11135™) were used in this study to test the hydrogels' biocompatibility. Cells were cultured in Keratinocyte-Serum Free Medium supplemented with 0.05 mg/mL bovine pituitary extract, 5 ng/mL epidermal growth factor, 500 ng/mL hydrocortisone, and 5 μg/mL insulin. Cells were incubated under the standard conditions and medium was refreshed every other day. Cells were passaged at 80% confluency with Trypsin-EDTA solution.

Biocompatibility of the hydrogels was assessed using both Resazurin assay and Calcein AM/Ethidium homodimer-I live/dead assay. For the Resazurin based cytotoxicity assay, 10,000 cells were seeded in 96-well plates and allowed to incubate overnight. The cell media was then replaced with fresh media containing the various hydrogel components. After 4 hours incubation, the cell media was removed and a 1:10 solution of resazurin to cell media was added to the wells and incubated for another 4 hours. The fluorescence was read at 545 nm for the excitation wavelength and 590 nm for the emission wavelength.

For the Calcein AM/Ethidium homodimer-I live/dead assay, the hydrogels were fabricated on 15 mm diameter glass slides and placed into a 12-well plate. Then, 240,000 cells were seeded on top of the gels. When the cells on the gel were approximately 80 percent confluent, the cell media was removed and new cell media containing 1:1000 Calcein AM and 1:500 Ethidium homodimer-I was added. After 45 minutes of incubation, the cells were imaged using an inverted microscope under the conditions of 37° C. and 5% $CO_2$. The cell survivability was quantified with ImageJ software.

In vivo Corneal Defect Model and Treatment. Adult New Zealand white rabbits were used for in vivo studies. Prior to surgery, one drop of proparacaine hydrochloride ophthalmic solution was added to experimental eye. A partial lamellar keratectomy was performed using a 3.5 mm customized vacuum trephine to introduce a circular defect, followed by removing the stromal layer with a blunt spatula. The hydrogel components were mixed in an Eppendorf tube and immediately 5 μL of the mixture was applied to the defect. The gel was allowed to form on the cornea for around 2 minutes and then covered with a protective contact lens. A partial tarsorrhaphy was performed to keep the animal from agitating the wound. Ofloxacin ophthalmic solution was applied daily to reduce the risk of infection and to keep the eye moist. Eye examinations were performed on day 4 and day 7. High-resolution photos of the eye were taken with a Paxos smartphone-based ophthalmic camera adapter. Optical coherence tomography (OCT) of the anterior eye segment were obtained with an HRA+OCT Spectralis© (Heidelberg Engineering Inc., MA, USA). On day 7, the corneas were collected and fixed in 4% PFA. The fixed cornea tissues were embedded in Tissue-Tek® O.C.T. compound and then cryo-sectioned.

Immunofluorescence. The fixed samples were washed with PBS thrice and then incubated overnight with primary antibodies alpha smooth muscle actin or zonula occludens-1 in 0.5% triton-x and 5% normal goat serum. The secondary antibody anti-mouse Alexa 546 was added. After washing, the sections were incubated with F-action and DAPI for 50 and 5 minutes respectively. The sections were then mounted and imaged with a confocal microscopy (Leica TCS SP5).

Data Analysis. All data are expressed as the mean±standard deviation. Each experiment was repeated at least 3 times unless otherwise indicated. A two-tailed Student's t-test was used for significance and p values <0.05 were considered as significant. Data means, standard deviations, and p values were calculated in Microsoft Excel 2016.

Results and Discussion

Synthesis. Four types of hydrogels were synthesized in this study: (1) collagen crosslinked via SPAAC click reaction (xCol); (2) HA crosslinked via thiol-ene click reaction (xHA); (3) semi-interpenetrating polymer (semi-IPN) composed of xHA and physically crosslinked collagen; and (4) IPN composed of xHA and xCol. Tissue-extracted collagen can form physical crosslinks to form gels that are significantly weaker than native tissue collagen, which has a well-organized structure. Physical crosslinked collagen also exhibits relatively poor transparency which is undesirable in the substitution of normally crystal-clear corneal stroma. Chemical crosslinking can improve the mechanical and optical properties of tissue-derived collagen. We used the SPAAC reaction, which is bio-orthogonal: it does not cross-react with functional groups biological systems, and proceeds under physiological conditions without the need for light, heat, initiator, or a catalyst and produces no side products. We modified aliquots of collagen with azido and dibenzocyclooctyne (DBCO) respectively, which formed the xCol via reaction between azido and DBCO groups upon mixing (FIG. 1A). In spite of these crosslinks, however, the xCol is still relatively weak due to a lack of fibrillar structure.

Native HA has also poor mechanical properties and short residence time due to its fast degradation. An effective way to overcome these limitations is to modify HA and enable crosslinking between HA molecules. Herein, we chose thiol-ene click chemistry to crosslink the HA (FIG. 1b) because thiol-ene click reaction is highly efficient, simple to execute, produces no side products, and proceeds relatively quickly under mild aqueous conditions. The precursors of the xHA are thiolated and methacrylated HA which have shown great potential in corneal wound healing and cell encapsulation. Thiolated HA have been shown to formed films that are reported to promote corneal epithelial wound healing and increase the corneal transparency in a corneal alkali burn rabbit model. Methacrylated HA can crosslink with thiolated heparin via visible light mediated thiol-ene reaction and encapsulate stem cells. Previously, we crosslinked methacrylated and thiolated HA using light-induced thiol-ene click reaction and riboflavin phosphate as photoinitiator. In this work, to suit the in-situ application of the final IPN on the cornea and avoid any possible light damage to posterior eye, we used a mildly basic conditions to drive the thiol-ene click reaction without using light or any exogenous chemical catalyst (FIG. 1a).

To ensure a high water content (97.35%) of the IPN and semi-IPN gels for corneal wound healing application, only 2.5% HA and 0.15% collagen were used. However, to compare the properties of four gels and study the effect of polymer content on the gel properties, we used different polymer contents as listed in Table 1.

TABLE 1

Polymer content of the hydrogels in this study.

| Gel | Col content | HA content |
|-----|-------------|------------|
| xCol | 0.15%, 0.3% | 0% |
| xHA | 0% | 2.5%, 5%, 10% |
| semi-IPN | 0.15%* | 2.5% |
| IPN | 0.15% | 2.5% |

*No chemical crosslinking.

Figure 2:
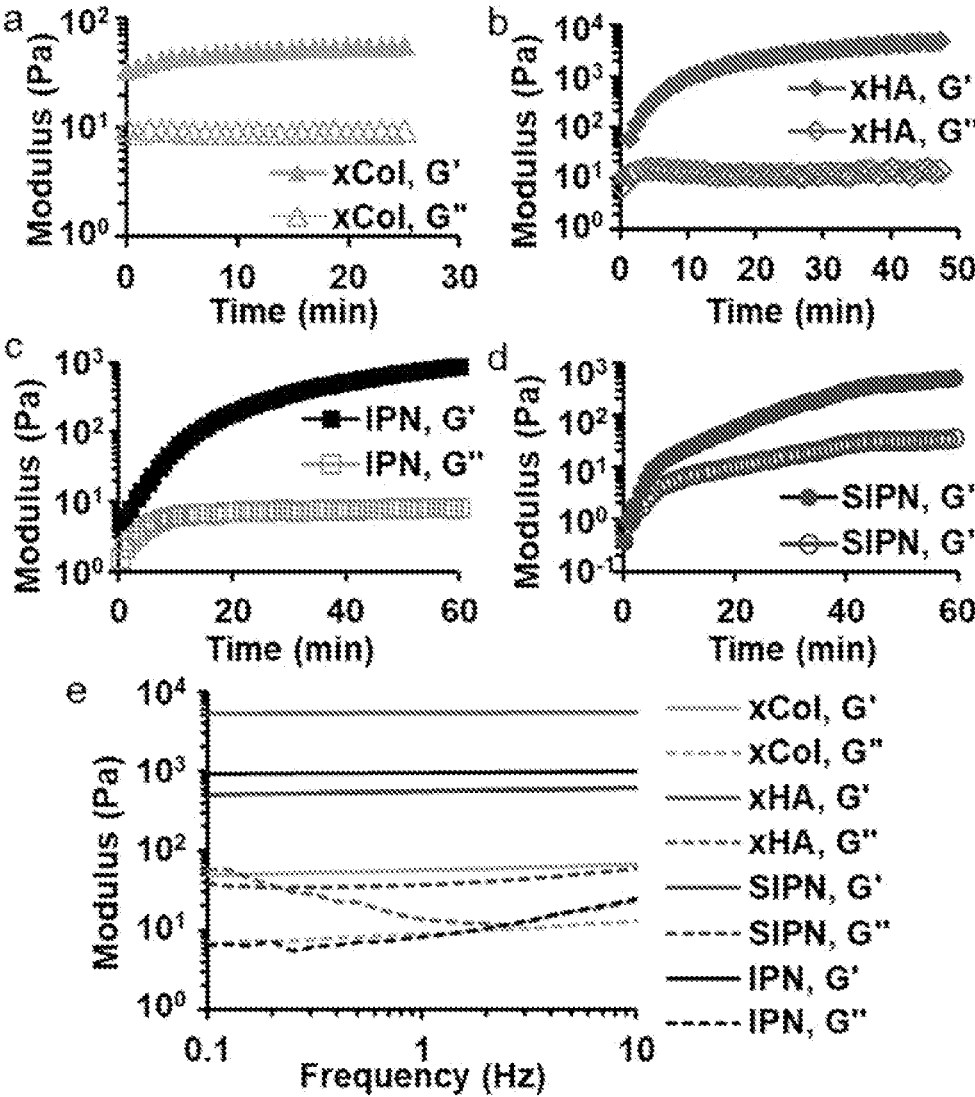
FIG. 2. Rheological characterizations of gels. In situ rheology measurements indicate the gelation time of the four type of gels: (a) collagen SPAAC gel with 0.3% collagen; (b) xHA with 5% HA; (c) IPN with 0.15% xCol and 2.5% xHA; (d) semi-IPN with 0.15% neutralized collagen and 2.5% xHA. G' and G" represent storage and loss modulus, respectively. (e) Dynamic moduli of gels as a function of frequency. All gels showed a viscoelastic solid-like status as the storage moduli were larger than the loss moduli.

Rheologic Characterizations. The xCol was formed via bio-orthogonal SPAAC-based click chemistry reaction as reported previously. To make the azido- and DBCO-conjugated collagen, a 2-fold molar excess of azido and DBCO to amine group of collage were used, which has been approved to be the most effective condition. To visualize the gel under fluorescence imaging, collagen-azide was modified with Alexa Fluor 647 via NHS facilitated amide reaction under physiological condition. There was 340 nmol Alexa Fluor 647 conjugated onto one gram of collagen-azido according to the fluorescence quantification. The Col-azide (0.3%) and Col-DBCO (0.3%) were mixed at 1:1 (v:v) and started to gel upon mixing, which was indicated by the higher storage modulus than loss modulus at the first measured time point of the in situ rheology measurement (FIG. 2a). The storage modulus reached half maximum within seconds and plateaued in approximately 20 minutes (FIG. 2a).

The xHA were synthesized with HA-SH and HA-MA via thiol-Michael type reaction, which is typically a base catalyzed thiol-ene click reaction. The thiol-Michael type reaction is particularly favorable for in situ gel application on cornea due to no need for light or photoinitiators because light possess risk for posterior eye damage and photoinitiators could affect the transmittance of gel. In addition, this reaction produces no byproducts and can be fast with the presence of base catalyst. Although this reaction needs base as catalyst, the amounts of catalyst can be very low. The degree of substitution of HA-SH and HA-MA were 58% and 43% respectively. Both HA-SH and HA-MA show a pH at approximately 6.5 after rehydration in PBS. PBS rehydrated HA-SH (5%) and HA-MA (5%) did not form gel within 24 hours upon mixing. Therefore, we studied the base strength and concentration to increase the final pH to approximately 7.1 so that the thiol-Michael reaction could happen to form gel under physiological conditions. This was achieved by rehydrating every milligram of HA-SH and HA-MA with 20 µL 7.13×PBS containing 0.79 mol sodium hydroxide. The rehydrated HA-SH and HA-MA were mixed at 1:1 (v:v) to form xHA. In situ rheology study showed that the HA-SH and HA-MA started to gel upon mixing and the storage modulus reached half maximum after 22 minutes and plateaued after 50 minutes (FIG. 2b).

FIG. 2c shows the in situ rheology of IPN, which can be considered as half 0.3% xCol and half 5% xHA interpenetrating with each other. The gel started to gel upon mixing and reached half maximum within 35 minutes. The slower gelation might be due to the mutual steric hindrance between the HA and collagen. The storage modulus of IPN did plateaued one hour after mixing. The semi-IPN gelation started slightly slower than the other three gels, which is indicated by that the storage modulus of semi-IPN became higher than the loss modulus 71 seconds after mixing (FIG. 2d). The storage modulus of semi-IPN reached half maximum at around 38 minutes upon mixing and plateaued one hour after mixing. The gelling time of the semi-IPN and IPN were very close.

The storages moduli of all gels were frequency independent (FIG. 2e), which indicates the complete gelation. The storage modulus was larger than the loss modulus over the entire frequency range for all gels, which means the gels were viscoelastic solids. The storage moduli of IPN (2.5% xHA and 0.15% xCol) was approximately 1000 Pa, which was 15-fold larger than that of 0.3% xCol, 1.25-fold larger than 2% xHA 2%, but 5-fold smaller than that of the 5% xHA. Generally, the storage moduli of the same hydrogels increase with its polymer concentration, so the storage modulus of the IPN can be further increased by adding more HA, which is the major component to increase the strength here. However, to maintain a high water content, lower polymer content is desired. Hence, we chose to add 2.5% HA in the IPN gel to balance strength and high water content. Moreover, the IPN showed a larger storage modulus but a smaller loss modulus than semi-IPN with the exact same polymer concentrations but non-chemically cross-linked collagen. Therefore, the IPN was less viscous and could dissipate less energy as heat than semi-IPN. The loss modulus of IPN was more like that of xCol at lower frequencies and become closer to that of xHA at higher frequencies (FIG. 2e).

Figure 3:
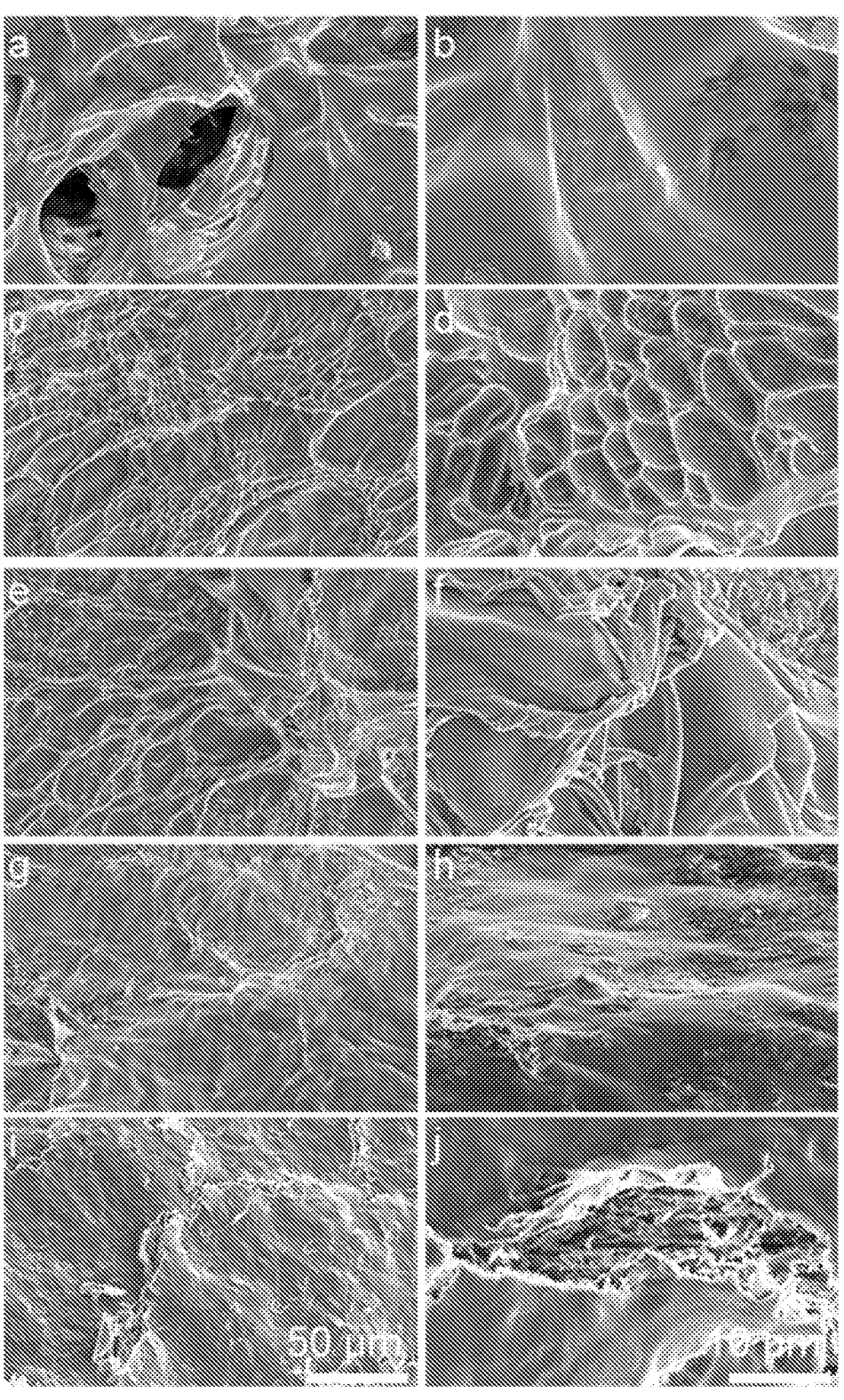
FIG. 3 SEM morphology of gels and de-epithelium cornea. (a, b) xCol 0.3% collagen; (c, d) xHA with 5% HA; (e, f) Semi-IPN with 0.15% neutralized collagen and 2.5% xHA (g, h) IPN with 0.15% xCol and 2.5% xHA; (i, j) de-epithelium cornea of rabbit. All samples were flash-frozen and lyophilized for SEM imaging.

Morphology. The morphology of lyophilized gels was examined with SEM and shown in FIG. 3. The xCol gel had a smooth surface under 1,000× and 5,000× magnifications (FIG. 3 a, b), while the xHA showed a wavy surface (FIG. 3 c, d). The semi-IPN surface maintained the wavy surface feature of the xHA (FIG. 3 e) and ruptured features (FIG. 3 f) which was possibly due to the physically cross-linked collagen. The IPN surface was smoother than xHA and rougher than xCol (FIG. 3 g, h), indicating that the xHA and xCol were mixed well in the IPN. Overall, the surface of the IPN was more homogeneous than that of the semi-IPN. Moreover, the IPN surface showed very similar features to the top view surface of de-epithelialized rabbit cornea (FIG. 3 i, j). This finding is suggestive that it may serve as a suitable substrate for corneal epithelial cells.

Transmittance and Refractive Index. Next, we investigated the transmittance of the gels over time and the results were shown in FIG. 4 a. Promisingly, the freshly made IPN had a high transmittance (over 94%) for the entire visible spectrum from 380 nm to 740 nm. The transmittance decreased slightly on day 1 and day 3. Noticeably, the transmittance of the IPN on day 3 were very close to day 1. The high and stable transmittance of IPN was expected because both xCol and xHA had high and stable transmittance. The semi-IPN, on the other hand, showed a low and unstable transmittance which was also seen in one of its component—the physically crosslinked collagen. Therefore, the IPN was more promising than the semi-IPN as a corneal defect filler, which should be highly transparent to let the light go through and be received by the posterior eye.

Figure 4:
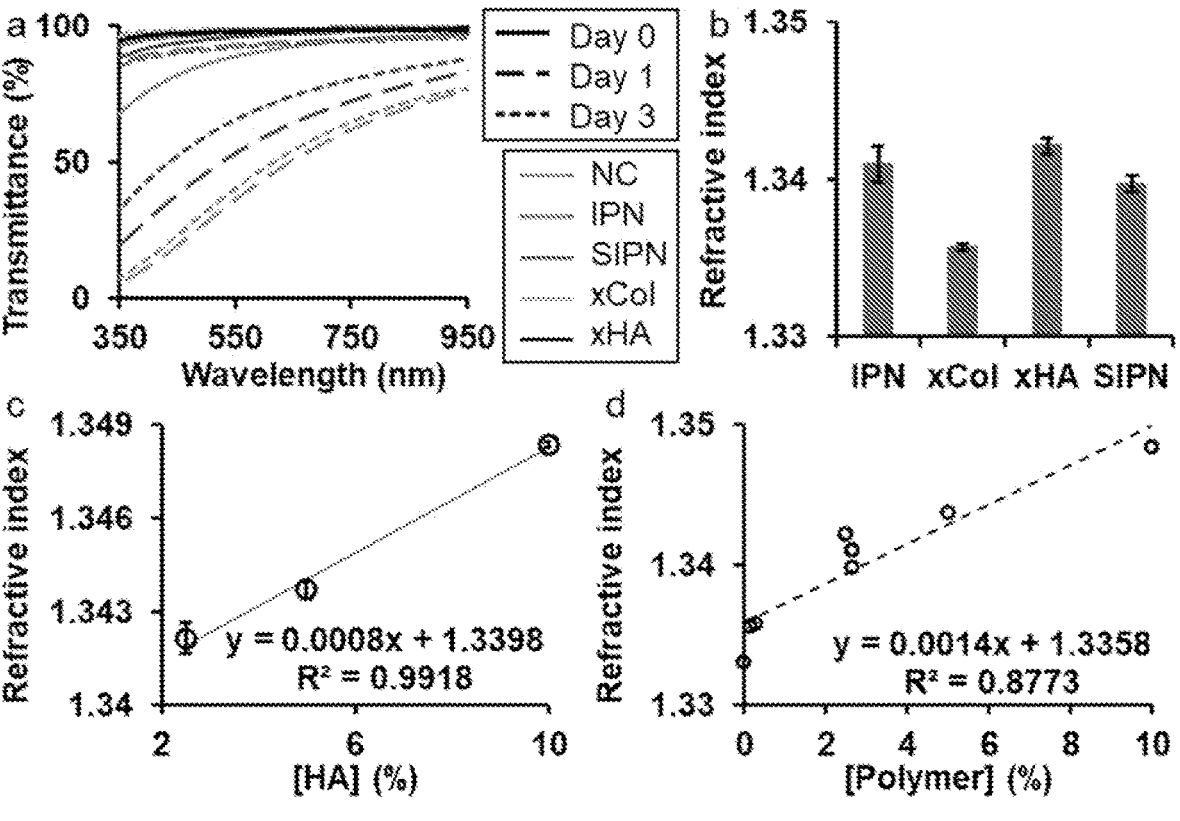
FIG. 4 Transmittance and refractive index of the gels. (a) Transmittance of hydrogels over time. (b) Refractive indexes of the four types of gels. (c) Refractive index of xHA with different HA concentrations. (d) Relationship between refractive index and total polymer concentrations. NC: non-chemically crosslinked collagen. IPN: 0.15% xCol and 2.5% xHA; semi-IPN: 0.15% collagen and 2.5% xHA; xCol: 0.15% collagen; xHA: 2.5% HA.

Another important optical parameter of a corneal defect filler is its refractive index, which together with the surface curvature radius determines the focal power. All gels in this study showed a lower refractive index than human cornea (1.376) which is to be expected given their higher water content. The refractive index of the IPN gel was 1.341, higher than 0.15% xCol (1.335) and semi-IPN (1.339) but lower than that of the 2.5% xHA (1.342) (FIG. 4 *b*). One method to increase the refractive index is to increase the polymer concentration. We first investigated the refractive index dependence on the solo polymer concentration with xHAs. Results showed that the refractive index of the xHA was linearly related to the concentration of HA with a Pearson's correlation coefficient 0.9959 (FIG. 4*c*). Based on the relationship between refractive index and HA concentration shown in FIG. 4*c*, 45.25% HA were required to reach the refractive index of human cornea. On the other hand, when the xCol, xHA, semi-IPN, and IPN were studied together, we found that the refractive index was still linearly dependent on polymer concentration (FIG. 4*d*). The Person's correlation coefficient was 0.9367. Based on this new relationship, 28.71% polymers were needed to reach the refractive index of human cornea at the time of application. However, we expect that the gel will be degraded and remodeled over time, and also be deterged to some degree by the corneal endothelial pump. Thus, we do not believe that matching the corneal refractive index is critical for a transient, regenerative scaffold acting as a stromal defect filler.

Figure 5:
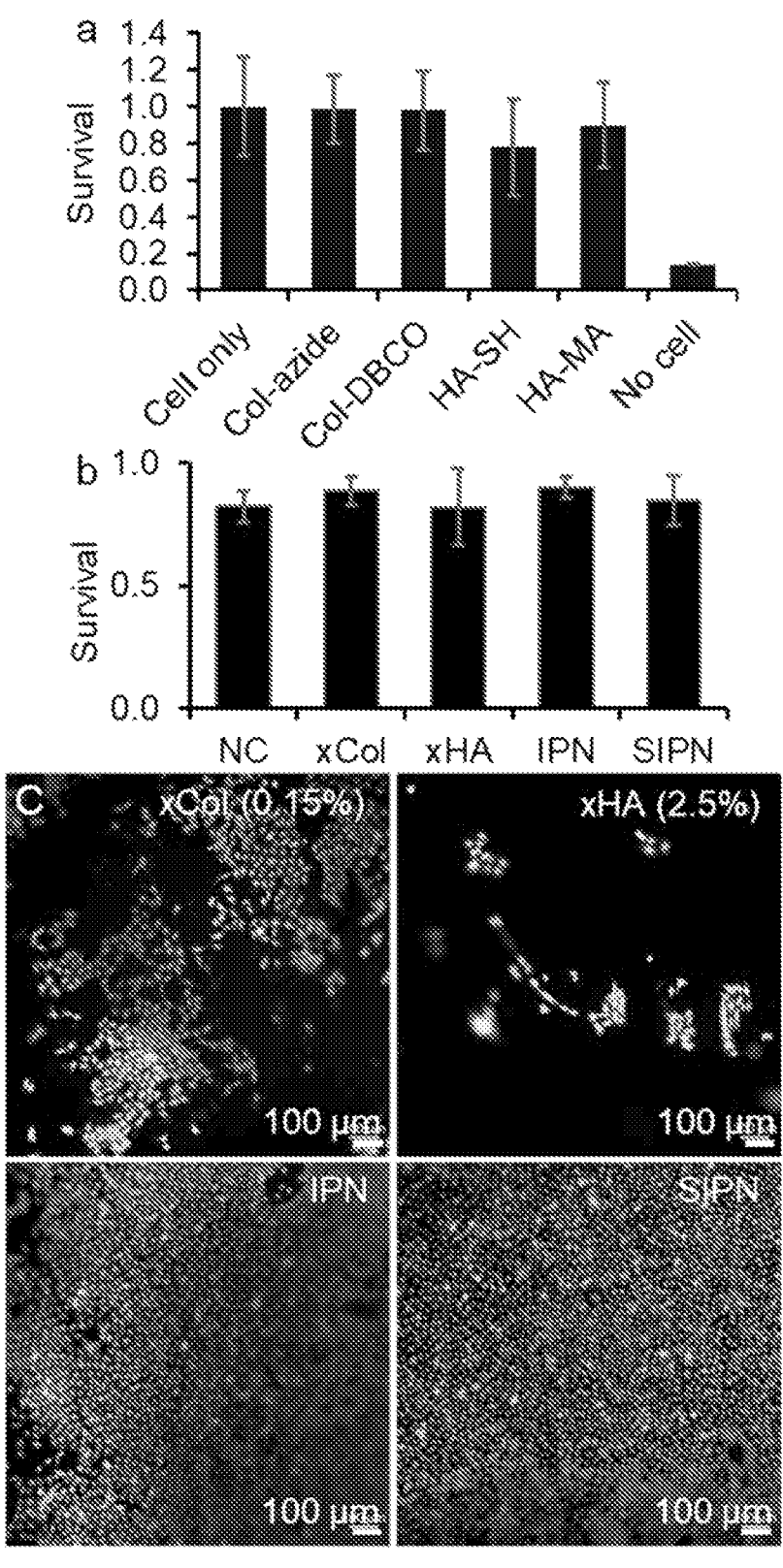
FIG. 5 Biocompatibility of the gel components and the gels. (a) Resazurin assay showed the corneal epithelial cell survival in the presence of gel components. (b) Calcein AM/Ethidium homodimer-I live/dead assay showed the corneal epithelial cell survival on top of gels. (c) Representative fluorescence images of cells on top of gels. IPN: 0.15% xCol and 2.5% xHA; semi-IPN: 0.15% collagen and 2.5% xHA; xCol: 0.15% collagen; xHA: 2.5% HA.

Biocompatibility. Both collagen and HA are inherent biocompatible natural macromolecules. However, the functionalization could decrease their biocompatibility depending on the reactivity of the functional groups. FIG. 5 the survival of corneal epithelial cells co-incubated with gel components after four hours. Cell survival normalized to cell only group was 99%, 98, 90%, and 78% when cells were incubated with Col-azide, Col-DBCO, HA-MA, and HA-SH respectively. The decrease in survival was not significant for all four gel components.

Next, we studied the biocompatibility of the gels with a live/dead assay and the results are shown in FIG. 5 *b*. The xCol (0.15%), xHA (2.5%), IPN, and semi-IPN all showed a cell survival over 80%, indicating the good biocompatibility of these gels. However, fluorescence microscopy revealed that the cell confluency on top of IPN and semi-IPN were much higher than that of the xCol and xHA (FIG. 5*c*). This result showed that the IPN combined the excellent cell adhesive property of collagen and strong mechanical property of HA, both of which improved the IPN gel's capacity for supporting the corneal epithelial cell growth.

Corneal Stromal Defect Healing. Ex vivo studies of gels filling anterior keratectomies in rabbit corneas demonstrated that the IPN could completely fill the corneal defect and restore the curvature of cornea (FIG. 6*a*). IPN could fill small irregularities in the corneal defects because it was added in a flowable liquid state before gelling. The curvature restoration was very likely due to the similar surface tension between the native corneal stromal tissue and the IPN, both of which had very high water content.

The IPN was clear in the first week after placement within the corneal stromal defects in vivo, while the untreated cornea became hazy on day 7. (FIG. 6*b*). OCT showed that the IPN was slightly dehydrated on day 4 and there were no significant differences in the corneal thickness of the keratectomy areas of the IPN-treated and non-treated corneas. (FIG. 6*c*). However, immunofluorescence studies showed substantial differences in the biological response to the treated and untreated areas. For the IPN-treated cornea, the IPN gel (red) was admixed with F-actin-expressing stromal cells and supported an overlying epithelium of 4-5 cell layers (FIG. 6*d*). The epithelium overlying the IPN was similar to that of normal epithelium and had a cuboidal basal cell layer underlying the anterior 3-4 layers of flattened superficial cells on day 7. However, the cuboidal basal cell layer on top of IPN was less dense than that of normal, untreated epithelium. Of note, the IPN treatment did not cause epithelial hyperplasia as was observed in the non-treated cornea with 15-20 layers of epithelial cells (FIG. 6*d*).

Figure 6:
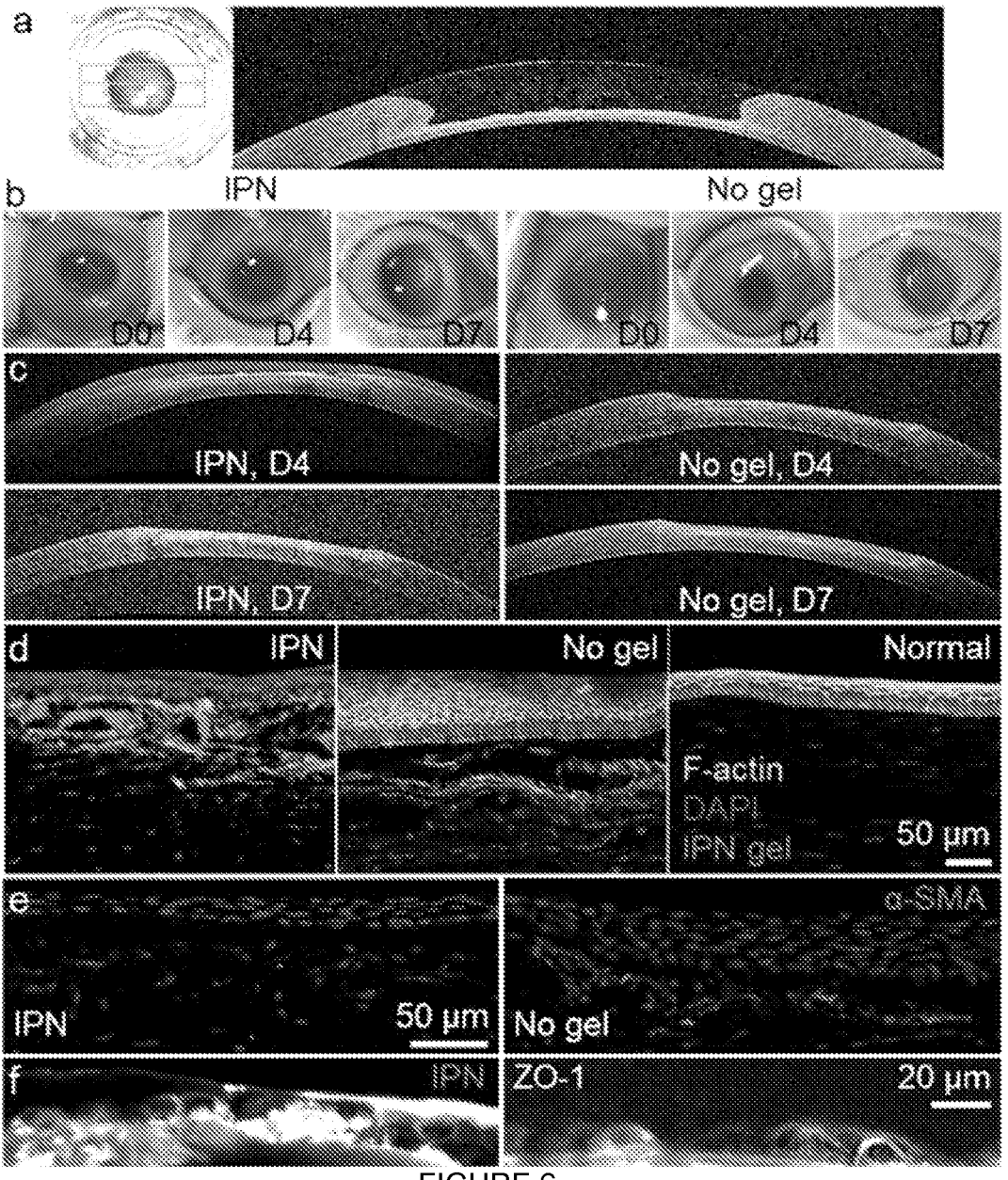
FIG. 6 Ex vivo and in vivo studies of the application of IPN as corneal defect filler. (a) OCT image show the curvature restoration of IPN on corneal defect ex vivo. The IPN was added to the corneal defect when it is still at liquid-like status. (b) Magnified photos of treated eyes on different days after treatment. (c) OCT images of the corneal defect recovery over one week. Immunofluorescence staining of regenerated anterior corneal tissues: (d) F-actin, (e) alpha smooth muscle actin, and (f) zonula occludens-1.

Injured corneas showed F-actin-expressing cells beneath the epithelium (FIG. 6*d*), while the normal cornea did not. These F-actin-expressing cells are likely activated myofibroblasts differentiated from stromal keratocytes. This activation of stromal cells is expected because it is one of the stages of wound healing. To confirm this, we stained the tissue slices with alpha smooth muscle actin ($\alpha$-SMA). Results showed that the non-treated cornea had more $\alpha$-SMA expression below the regenerated epithelium than the IPN-treated corneas did (FIG. 6 *e*). Therefore, the IPN appeared to reduce myofibroblastic activity which could lead to corneal haze and scarring. Both regenerated epithelia on IPN-treated and non-treated corneas expressed the tight junction protein zonula occludens-1 (ZO-1), the IPN-treated corneas showing higher ZO-1 expression than the non-treated corneas (FIG. 6*f*). The decreased $\alpha$-SMA expression and increased ZO-1 expression seen in the IPN-treated corneas suggests that the in situ-forming, simultaneous IPN of collagen and HA holds promise as a functional regenerative defect filler for the cornea.

In this study, we reported on a natural biomacromolecule-based, in situ forming simultaneous (one-pot) IPN hydrogel and evaluated its potential as a corneal defect filler to treat corneal stromal injuries. The IPN exhibited excellent biocompatibility due to the use of HA and collagen as well as the use of dual and non-competing crosslinking strategies, thiol-ene and bio-orthogonal SPAAC-based click chemistries. The IPN gels have high water content and maintained high and stable transmittance over several days. The IPN combines the advantages of HA and collagen overcomes many of their individual shortcomings. The collagen network conferred cell adhesivity while the HA conferred improved mechanical properties. The IPN could be applied to a corneal defect in a flowable liquid state and then form a smooth contour on its surface as it gels. Lastly, in vivo studies showed that the IPN-treatment promotes epithelial overgrowth, promotes tight junction formation in the epithelium, and decreases myofibroblast activity in the wounded stroma. Future studies will involve longer-term in vivo studies of the corneal wound healing response to this in situ-forming, simultaneous collagen-HA IPN.

ABBREVIATIONS. IPN, interpenetrating polymer network; HA, hyaluronic acid; xHA, thiol-ene click crosslinked hyaluronic acid; HA-SH, thiolated hyaluronic acid; HA-MA, methacrylated hyaluronic acid; SPAAC, strain-promoted azide-alkyne cycloaddition; Col, collagen; xCol, SPAAC click crosslinked collagen; DBCO, dibenzocyclooctyne; Col-azide, collagen modified with azido; Col-DBCO, collagen modified with DBCO; NC, neutralized collagen; PEG, poly(ethylene glycol); NHS, N-hydroxysuccinimidyl ester; SEM, scanning electron microscopy; OCT, optical coherence tomography; ZO-1, zonula occludens-1; $\alpha$-SMA, alpha smooth muscle actin; DAPI, 4',6-diamidino-2-phenylindole; PBS, phosphate buffered saline.

REFERENCES

1. Abdelkader, A.; Elewah, E.-S. M.; Kaufman, H. E., Confocal Microscopy of Corneal Wound Healing After Deep Lamellar Keratoplasty in Rabbits. *Archives of Ophthalmology* 2010, 128 (1), 75-80.

2. Gain, P.; Jullienne, R.; He, Z. G.; Aldossary, M.; Acquart, S.; Cognasse, F.; Thuret, G., Global Survey of Corneal Transplantation and Eye Banking. *Jama Ophthalmology* 2016, 134 (2), 167-173.

3. Lee, H. J.; Fernandes-Cunha, G. M.; Na, K.-S.; Hull, S. M.; Myung, D., Bio-Orthogonally Crosslinked, In Situ Forming Corneal Stromal Tissue Substitute. *Advanced Healthcare Materials* 2018, 7(19), 1800560.

4. Sani, E. S.; Kheirkhah, A.; Rana, D.; Sun, Z. M.; Foulsham, W.; Sheikhi, A.; Khademhosseini, A.; Dana, R.; Annabi, N., Sutureless repair of corneal injuries using naturally derived bioadhesive hydrogels. *Science Advances* 2019, 5 (3).

5. Islam, M. M.; Buznyk, O.; Reddy, J. C.; Pasyechnikova, N.; Alarcon, E. I.; Hayes, S.; Lewis, P.; Fagerholm, P.; He, C.; Iakymenko, S.; Liu, W.; Meek, K. M.; Sangwan, V. S.; Griffith, M., Biomaterials-enabled cornea regeneration in patients at high risk for rejection of donor tissue transplantation. *npj Regenerative Medicine* 2018, 3 (1), 2.

6. Li, L.; Lu, C.; Wang, L.; Chen, M.; White, J.; Hao, X.; McLean, K. M.; Chen, H.; Hughes, T. C., Gelatin-Based Photocurable Hydrogels for Corneal Wound Repair. *ACS Appl Mater Interfaces* 2018, 10(16), 13283-13292.

7. Xu, H. L.; Tong, M. Q.; Wang, L. F.; Chen, R.; Li, X. Z.; Sohawon, Y.; Yao, Q.; Xiao, J.; Zhao, Y. Z., Thiolated gamma-polyglutamic acid as a bioadhesive hydrogel-forming material: evaluation of gelation, bioadhesive properties and sustained release of KGF in the repair of injured corneas. *Biomaterials Science* 2019, 7 (6), 2582-2599.

8. Kenne, L.; Gohil, S.; Nilsson, E. M.; Karlsson, A.; Ericsson, D.; Helander Kenne, A.; Nord, L. I., Modification and cross-linking parameters in hyaluronic acid hydrogels—definitions and analytical methods. *Carbohydr. Polym.* 2013, 91 (1), 410-8.

9. Kim, S. J.; Lee, C. K.; Lee, Y. M.; Kim, I. Y.; Kim, S. I., Electrical/pH-sensitive swelling behavior of polyelectrolyte hydrogels prepared with hyaluronic acid-poly(vinyl alcohol) interpenetrating polymer networks. *React. Funct. Polym.* 2003, 55 (3), 291-298.

10. Burdick, J. A.; Prestwich, G. D., Hyaluronic Acid Hydrogels for Biomedical Applications. *Adv. Mater.* 2011, 23(12), H41-H56.

11. Neuman, M. G.; Nanau, R. M.; Oruña-Sanchez, L.; Coto, G., Hyaluronic acid and wound healing. *Journal of Pharmacy & Pharmaceutical Sciences* 2015, 18 (1), 53-60.

12. Zhong, J.; Deng, Y.; Tian, B.; Wang, B.; Sun, Y.; Huang, H.; Chen, L.; Ling, S.; Yuan, J., Hyaluronate acid-dependent protection and enhanced corneal wound healing against oxidative damage in corneal epithelial cells. *Journal of ophthalmology* 2016, 2016.

13. Fernandes-Cunha, G. M.; Na, K. S.; Putra, I.; Lee, H. J.; Hull, S.; Cheng, Y. C.; Blanco, I. J.; Eslani, M.; Djalilian, A. R.; Myung, D., Corneal Wound Healing Effects of Mesenchymal Stem Cell Secretome Delivered Within a Viscoelastic Gel Carrier. *Stem Cells Transl Med* 2019.

14. Lee, H. J.; Fernandes-Cunha, G. M.; Myung, D., In situ-forming hyaluronic acid hydrogel through visible light-induced thiol-ene reaction. *React. Funct. Polym.* 2018, 131, 29-35.

15. Rýglovd, Š.; Braun, M.; Suchý, T., Collagen and Its Modifications—Crucial Aspects with Concern to Its Processing and Analysis. *Macromolecular Materials and Engineering* 2017, 302 (6), 1600460.

16. Suri, S.; Schmidt, C. E., Photopatterned collagen-hyaluronic acid interpenetrating polymer network hydrogels. *Acta Biomater.* 2009, 5 (7), 2385-2397.

17. Naseri, N.; Deepa, B.; Mathew, A. P.; Oksman, K.; Girandon, L., Nanocellulose-Based Interpenetrating Polymer Network (IPN) Hydrogels for Cartilage Applications. *Biomacromolecules* 2016, 17 (11), 3714-3723.

18. Jeon, O.; Shin, J.-Y.; Marks, R.; Hopkins, M.; Kim, T.-H.; Park, H.-H.; Alsberg, E., Highly Elastic and Tough Interpenetrating Polymer Network-Structured Hybrid Hydrogels for Cyclic Mechanical Loading-Enhanced Tissue Engineering. *Chem. Mater.* 2017, 29 (19), 8425-8432.

19. Gong, J. P.; Katsuyama, Y.; Kurokawa, T.; Osada, Y., Double-Network Hydrogels with Extremely High Mechanical Strength. *Adv. Mater.* 2003, 15 (14), 1155-1158.

20. Myung, D.; Waters, D.; Wiseman, M.; Duhamel, P. E.; Noolandi, J.; Ta, C. N.; Frank, C. W., Progress in the development of interpenetrating polymer network hydrogels. *Polym. Adv. Technol.* 2008, 19 (6), 647-657.

21. Myung, D.; Koh, W.; Ko, J.; Hu, Y.; Carrasco, M.; Noolandi, J.; Ta, C. N.; Frank, C. W., Biomimetic strain hardening in interpenetrating polymer network hydrogels. *Polymer* 2007, 48 (18), 5376-5387.

22. Hodgson, S. M.; Bakaic, E.; Stewart, S. A.; Hoare, T.; Adronov, A., Properties of Poly(ethylene glycol) Hydrogels Cross-Linked via Strain-Promoted Alkyne-Azide Cycloaddition (SPAAC). *Biomacromolecules* 2016, 17 (3), 1093-1100.

23. Madl, C. M.; Katz, L. M.; Heilshorn, S. C., Bio-Orthogonally Crosslinked, Engineered Protein Hydrogels with Tunable Mechanics and Biochemistry for Cell Encapsulation. *Adv. Funct. Mater.* 2016, 26 (21), 3612-3620.

24. Leonard, B. C.; Cosert, K.; Winkler, M.; Marangakis, A.; Thomasy, S. M.; Murphy, C. J.; Jester, J. V.; Raghunathan, V. K., Stromal Collagen Arrangement Correlates with Stiffness of the Canine Cornea. *Bioengineering (Basel)* 2019, 7 (1).

25. Highley, C. B.; Prestwich, G. D.; Burdick, J. A., Recent advances in hyaluronic acid hydrogels for biomedical applications. *Curr. Opin. Biotechnol.* 2016, 40, 35-40.

26. Hoyle, C. E.; Bowman, C. N., Thiol-Ene Click Chemistry. *Angew. Chem. Int. Ed.* 2010, 49 (9), 1540-1573.

27. Griffith, G. L.; Wirostko, B.; Lee, H. K.; Cornell, L. E.; McDaniel, J. S.; Zamora, D. O.; Johnson, A. J., Treatment of corneal chemical alkali burns with a crosslinked thiolated hyaluronic acid film. *Burns* 2018, 44 (5), 1179-1186.

28. Gwon, K.; Kim, E.; Tae, G., Heparin-hyaluronic acid hydrogel in support of cellular activities of 3D encapsulated adipose derived stem cells. *Acta Biomater.* 2017, 49, 284-295.

29. Zhang, Y.; Liu, S.; Li, T.; Zhang, L.; Azhar, U.; Ma, J.; Zhai, C.; Zong, C.; Zhang, S., Cytocompatible and non-fouling zwitterionic hyaluronic acid-based hydrogels using thiol-ene "click" chemistry for cell encapsulation. *Carbohydr. Polym.* 2020, 236, 116021.

30. Kharkar, P. M.; Rehmann, M. S.; Skeens, K. M.; Maverakis, E.; Kloxin, A. M., Thiol-ene Click Hydrogels for Therapeutic Delivery. *ACS Biomaterials Science & Engineering* 2016, 2 (2), 165-179.

31. Zhou, J.; Wang, G.; Zou, L.; Tang, L.; Marquez, M.; Hu, Z., Viscoelastic behavior and in vivo release study of microgel dispersions with inverse thermoreversible gelation. *Biomacromolecules* 2008, 9 (1), 142-148.

32. Olsen, T., On the Calculation of Power from Curvature of the Cornea. *Br. J. Ophthalmol.* 1986, 70 (2), 152-154.

33. Wang, L.; Mahmoud, A. M.; Anderson, B. L.; Koch, D. D.; Roberts, C. J., Total Corneal Power Estimation: Ray Tracing Method versus Gaussian Optics Formula. *Investigative Ophthalmology & Visual Science* 2011, 52 (3), 1716-1722.

34. Chen, J.; Li, Z.; Zhang, L.; Ou, S.; Wang, Y.; He, X.; Zou, D.; Jia, C.; Hu, Q.; Yang, S.; Li, X.; Li, J.; Wang, J.; Sun, H.; Chen, Y.; Zhu, Y. T.; Tseng, S. C. G.; Liu, Z.; Li, W., Descemet's Membrane Supports Corneal Endothelial Cell Regeneration in Rabbits. *Sci Rep* 2017, 7 (1), 6983.

35. Sugrue, S. P.; Zieske, J. D., ZO1 in Corneal Epithelium: Association to the Zonula Occludens and Adherens Junctions. *Experimental Eye Research* 1997, 64 (1), 11-20.

Example 2

Bio-Orthogonally Crosslinked, In Situ-Forming Collagen-Hyaluronate Co-Polymer for Suture-Free Corneal Defect Repair Biomaterials that mimic corneal stroma can decrease the need for donor cornea tissue and can be more advanced than donor corneas in terms of decrease infection and rejection. We developed a bio-orthogonally crosslinked collagen-hyaluronate co-polymer which can fill corneal defects in situ and without the needs for any sutures, initiators, or catalysts. This copolymer is a hydrogel holding over 97% water. We studied the effects of modification strategy on the light transmittance of the copolymeric hydrogel. The transmittance of the optimized hydrogel in the visible light range was over 94%. We also investigated the mechanical properties, refractive index, SEM morphology, biocompatibility, and corneal re-epithelialization capacity of this hyaluronate-collagen copolymeric hydrogel. Our in vitro, in vivo, and ex vivo results demonstrated this bio-orthogonally crosslinked hyaluronate-collagen copolymeric hydrogel as an excellent biomaterial for cornea repair and regeneration.

Although photo-initiation crosslinking is efficient and highly controllable, its application for in situ gel forming on cornea poses certain limitations such as the need for an external light energy source, a photo-initiator, and reactive side products. Here, we used the bio-orthogonal strain-promoted azide-alkyne cycloaddition (SPAAC) to crosslink hyaluronate and collagen under ambient conditions without the need for light, heat, photo-initiators, or any other chemical initiators or catalysts. This copolymer hydrogel integrates the cell-adhesive nature of collagen and the regenerative capacity of hyaluronic acid. We systematically studied bioconjugations strategies for this co-polymer and obtained a highly transparent hydrogel with physical and optical properties and morphology comparable to those of corneal stroma. To study the copolymeric hydrogel's corneal stromal wound healing effect in vivo, we used a deep keratectomy model in rabbits using a custom vacuum trephine. Our results demonstrate that the in situ-forming, bio-orthogonally crosslinked collagen-HA copolymeric hydrogel is a promising corneal stromal substitute.

Materials and Methods

Materials. Dibenzocyclooctyne-sulfo-N-hydroxysuccinimidyl ester (DBCO-sulfo-NHS), dimethyl sulfoxide (DMSO), sodium hydroxide solution (1.0 N), agar, insulin, Triton-X, trypan blue solution, and resazurin based in vitro toxicology assay kit were purchased from Sigma-Aldrich (St. Louis, MO, USA). Phosphate-buffered saline (PBS) pH 7.4, 10×PBS, Slide-A-Lyzer dialysis kit (3.5k MWCO), collagen I bovine protein solution (5 mg mL$^{-1}$), epidermal growth factor (EGF) recombinant human protein, fetal bovine serum (FBS), keratinocyte-serum free media (KSFM), bovine pyruvate extract (BPE), ITS Premix Universal Culture Supplement, trypsin, live/dead viability/cytotoxicity staining kit, paraformaldehyde (PFA), 5% normal goat serum, Alexa Fluor Phalloidin 488, Alexa Fluor 647-N-hydroxysuccinimidyl ester, and Alexa Fluor 546 secondary antibody were purchased from Thermo Fisher Scientific (Waltham, MA, USA). Azido-poly(ethylene glycol)$_5$-N-hydroxysuccinimidyl ester (azido-PEG5-NHS) was purchased from BroadPharm (San Diego, CA, USA). Hyaluronate amine (40-50% degree of substitute) was purchased from Creative PEGWorks (Durham, NC, USA).

Hyaluronate-collagen copolymeric hydrogel synthesis. First, to make HA-azide, 20 mg/mL hyaluronate amine in distilled deionized water was pH neutralized using a neutralization solution at a 1:10 ratio. The neutralization solution was 10×PBS containing 50 mM sodium hydroxide. Next, we made 1000 mg/mL azido-PEG5-NHS with DMSO and added 20.52 μL into 1 mL neutralized HA-amine solution. The mixture was rotated for 2 hours at 4° C. To make fluorescent hydrogel for better visualization in vivo, Alexa Fluor 647 was conjugated to the azide-conjugated hyaluronate amine. Specifically, 16.67 μg Alexa Fluor 647-N-hydroxysuccinimidyl ester were added into 1 mL azide-conjugated hyaluronate amine and incubated for 2 hours at 4° C. Last, azide- or both azide- and 647-conjugated hyaluronate amine was dialyzed using Slide-A-Lyzer dialysis kit overnight at 4° C. in PBS and then lyophilized.

For Col-DBCO conjugation, type I bovine collagen was pH neutralized using a solution of 1.0 M sodium hydroxide solution, distilled deionized water, and 10×PBS in a 3:57:20 ratio. The 5 mg/ml collagen solution was mixed with the neutralization solution in 3:2 ratio so that the final concentration of collagen was 3 mg/ml. Then, 2 mg DBCO-sulfo-NHS was dissolved in 20 μL PBS, and quickly mixed 8.52 μL DBCO-sulfo-NHS solution with 1 mL neutralized collagen. The mixture was incubated for 2 hours at 4° C. DBCO-conjugated collagen was used freshly and without dialysis unless specified.

To make the different content hyaluronate-collagen copolymeric hydrogels via SPAAC click reaction, lyophilized HA-azide or HA-azide-647 were dissolved in PBS at 10, 30, or 50 mg/mL, and the Col-DBCO were diluted to 2 and 1 mg/mL with PBS. HA-azide were then mixed with Col-DBCO at a 1:1 ratio via pipetting and formed hydrogel at ambient temperature.

Hydrogel characterization. The conjugation ratios were evaluated by UV-vis absorbance spectra from 270 nm to 350 nm (Tecan Microplate Reader). DBCO-sulfo-NHS and azido-PEG5-NHS were dissolved in PBS at known concentrations and used as standards. Neutralized collagen and hyaluronate amine were used controls.

The transmittance of the hydrogel was calculated based on the measured absorbance. First, 100 μL of hydrogels was formed in a well of 96-well plate. Absorbance of the hydrogels was measured between 200 nm and 1000 nm (Tecan Microplate Reader) and blanked with PBS. The transmittance was calculated using the relationship T (%)=1/$10^4$×100, where A is the absorbance.

The refractive index of hydrogels was measured with a digital refractometer (HI96800, Hanna Instruments). The machine was calibrated with double distilled water. Surface focal power (Ds) of the hydrogels were calculated with the formula $D_s=(n-1)/r$, where n is the measured refractive index and r is the radius of curvature which is 8 mm for human.

The storage and loss moduli of the collagen gels were evaluated using an ARES-G2 rheometer (TA Instruments, New Castle, DE, USA). For in situ measurements, 50 μL HA-azide and 50 μL Col-DBCO were added and mixed on the stage and a 25 mm parallel plate was used. To measure storage and loss moduli of cornea buttons, rabbit cornea buttons were created with 8 mm biopsy punch and then the epithelium and endothelium layers were removed. A wound was created with 3.5 mm biopsy punch and spatula. The wound was either filled with PBS or 5 μL hydrogel. An 8 mm parallel plate was used for the cornea buttons. Time sweeps were performed at 25 degree Celsius for 1 hour at 1% strain and 1 Hz oscillatory frequency. Frequency sweeps were performed from 0.1 to 10 Hz with a fixed 1% strain.

SEM imaging were used to examine the morphology and biointegration of the hydrogels. The samples were flattened on silicon wafers, flash frozen with liquid nitrogen, and then lyophilized to remove the water. The lyophilized samples were fixed on top of the sample holder with silver paste and then coated with Au/Pd (60:40 ratio). The samples were imaged with an Apreo S LoVac SEM (Thermo Fisher Scientific) at 2-5 kV and 13-50 pA.

Biocompatibility. Biocompatibility of HA-azide and Col-DBCO was evaluated with corneal epithelial cells (ATCC© CRL-11135™) via a Resazurin based cytotoxicity assay. Corneal epithelial cells were seeded into 96 well plates at a density of 10,000 cells/well and incubated overnight. The old cell media was then replaced with hydrogel components (either HA-azide or Col-DBCO) contained cell media. After 4 hours incubation, the media were aspirated and resazurin solution was added to cell media at a ratio of 1:10. After 4 hours, the fluorescence was read at an excitation wavelength of 545 nm and emission wavelength of 590 nm.

Additionally, we tested the biocompatibility of the formed hydrogel with a Calcein AM/Ethidium homodimer-I live/dead assay. Hydrogel were formed on a glass slide and then placed inside a 12 well plate. Then, 150,000 corneal epithelial cells were added into the 12 well plate to cover the gel. Cells were imaged on days 0, 1, 2, and 4. For day 0, cells were allowed 3 hours to adhere to the surface of the gel. Calcein AM was added at a 1:1000 ratio and Ethidium homodimer-1 was added at a 1:500 ratio to cell media and added to the cells. Cells were incubated for 45 minutes after adding the dyes and imaging was done under the conditions of 37° C. and 5% $CO_2$. Live/dead counts were analyzed using the ImageJ counter feature.

Organ Culture. Fresh rabbit eyes were obtained from Vision Technologies (Glen Burnie, MD). Keratectomy was performed using a customized 3.5 mm vacuum trephine to make a circular cut. The stromal tissue in the wound area was then removed with a spatula. Next, the entire cornea with approximately 1 mm scleral rim on the edge was removed from the eyeball. The cornea was sterilized in beta-iodine and 1×PBS containing 1% penicillin/streptomycin. The cornea was immediately transferred onto preformed agar plugs to maintain normal culture and nutritional support. Agar plugs were made of a 1:1 mixture of serum-free medium containing double strength antibiotics and 2% agar in distilled water. The agar plugs were made in polydimethylsiloxane (PDMS) molds. The culture medium used was DMEM/F-12 containing 120 μg/mL penicillin G, 200 μg/mL streptomycin sulfate and ITS premix universal culture supplement. Samples were incubated at 37° C. in 5% $CO_2$ and the medium was changed every 2 days. At day 4, cornea was fixed in 4% PFA and cryosectioned for immunofluorescence staining or in 10% formalin and sectioned for histochemical staining.

In Vivo Lamellar Keratectomy Studies. Adult New Zealand white rabbits were used in this study. Animal experiments were designed to conform with the ARVO statement for the Use of Animals in Ophthalmic and Vision Research and were reviewed and approved by the Stanford University Institutional Animal Care and Use Committee. All anesthesia techniques were performed by the veterinary service center (VSC) at Stanford University. Prior to surgery, one drop of proparacaine hydrochloride ophthalmic solution was added to the eye receiving treatment. Partial keratectomy was performed on the right eye using a 3.5 mm customized vacuum trephine to create a deep circular cut and a spatula to remove the collagen fibril layers. 5 μL of premixed HA-azide and Col-DBCO was applied to the wounded site and allowed to gel in situ. A contact lens was applied to protect the hydrogel from scratching. A tarsorrhaphy was then performed to prevent agitation by the animal and to help keep the contact lens and gel in place. Ofloxacin ophthalmic solution was applied daily to prevent infection and to retain moisture of the eye. On days 4 and 7, the tarsorrhaphy was removed for eye examination: photograph with a Paxos smartphone-based ophthalmic camera adapter[12] and optical coherence tomography (OCT). On day 7, the rabbits' eyes were enucleated, fixed in 4% PFA, and cryosectioned for imaging.

Statistical analysis. All data are expressed as the mean±standard deviation. Each experiment was repeated at least 3 times. A two-tailed Student's t-test was used for significance and p values <0.05 were considered as significant. Data means, standard deviations, and p values were calculated in Microsoft Excel 2016.

Results and Discussion

Figure 7:
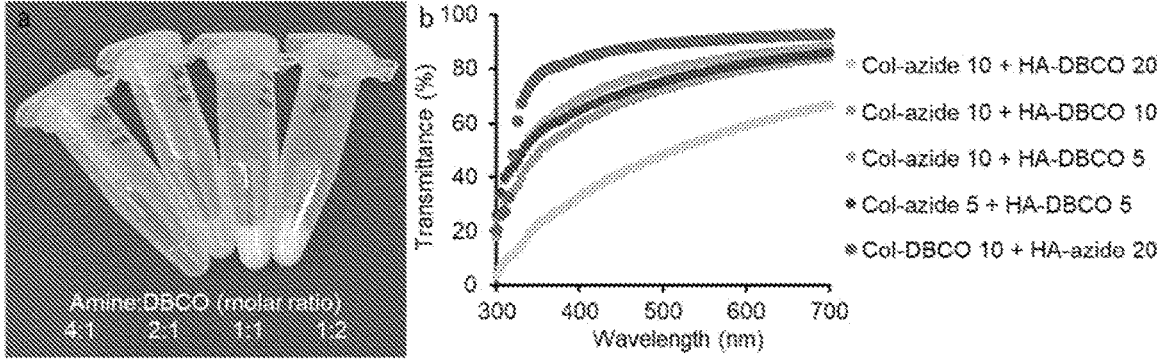
FIG. 7 Transmittance of hyaluronate-collagen copolymeric hydrogel formed with hyaluronate-DBCO and collagen-azide via SPAAC click gelation. (a) Hyaluronate became opaque after modified with DBCO and the opaqueness increased as the amine-to-DBCO molar ratio decreased. (b) The transmittance of hyaluronate-collagen copolymeric hydrogel decreased significantly when using hyaluronate-DBCO and collagen-azide to form the gel than using hyaluronate-azide and collagen-DBCO.

Synthetic strategy for highly transparent hyaluronate-collagen copolymeric hydrogel. To make the hyaluronate-collagen copolymer via SPAAC reaction, there are two possible modification strategies: modify hyaluronate with azido (abbreviated as HA-azide hereafter) and collagen with DBCO (abbreviated as Col-DBCO hereafter) or the opposite. We found that the first strategy was superior than the second one due to significant differences in transparency of their products. DBCO modified hyaluronate (HA-DBCO), one of the mid-products of the second strategy, was translucent when the molar ratio of amine-to DBCO was 4, and it became completely opaque when this ratio increased to 2 (FIG. 7a). Therefore, the transmittance of hydrogels formed with HA-DBCO and collagen-azide was greatly dependent on the amount of HA-DBCO added (FIG. 7b).

Figure 8:
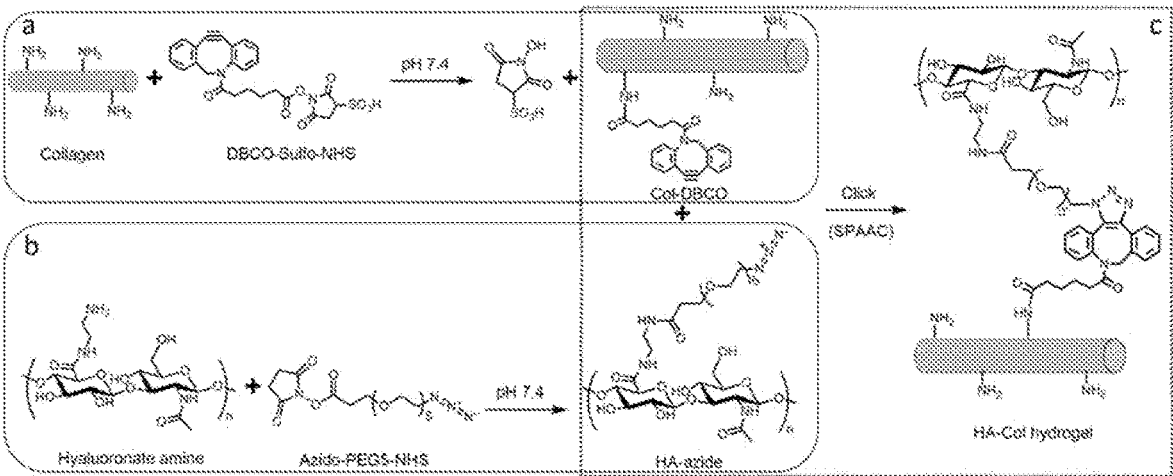
FIG. 8. Hyaluronate-collagen hydrogel crosslinked via strain-promoted azide-alkyne cycloaddition (SPAAC). (a-c) Scheme of the hydrogel formation. (a) Primary amine groups on collagen react with dibenzocyclooctyne-sulfo-N-hydroxysuccinimidyl ester to form collagen-DBCO (Col-DBCO). (b) Amidated hyaluronate react with azido-PEG5-NHS and formed hyaluronate-azide (HA-azide). (c) The SPAAC reaction between DBCO and azido groups formed hyaluronate-collagen copolymer without producing any byproducts.
Figure 9:
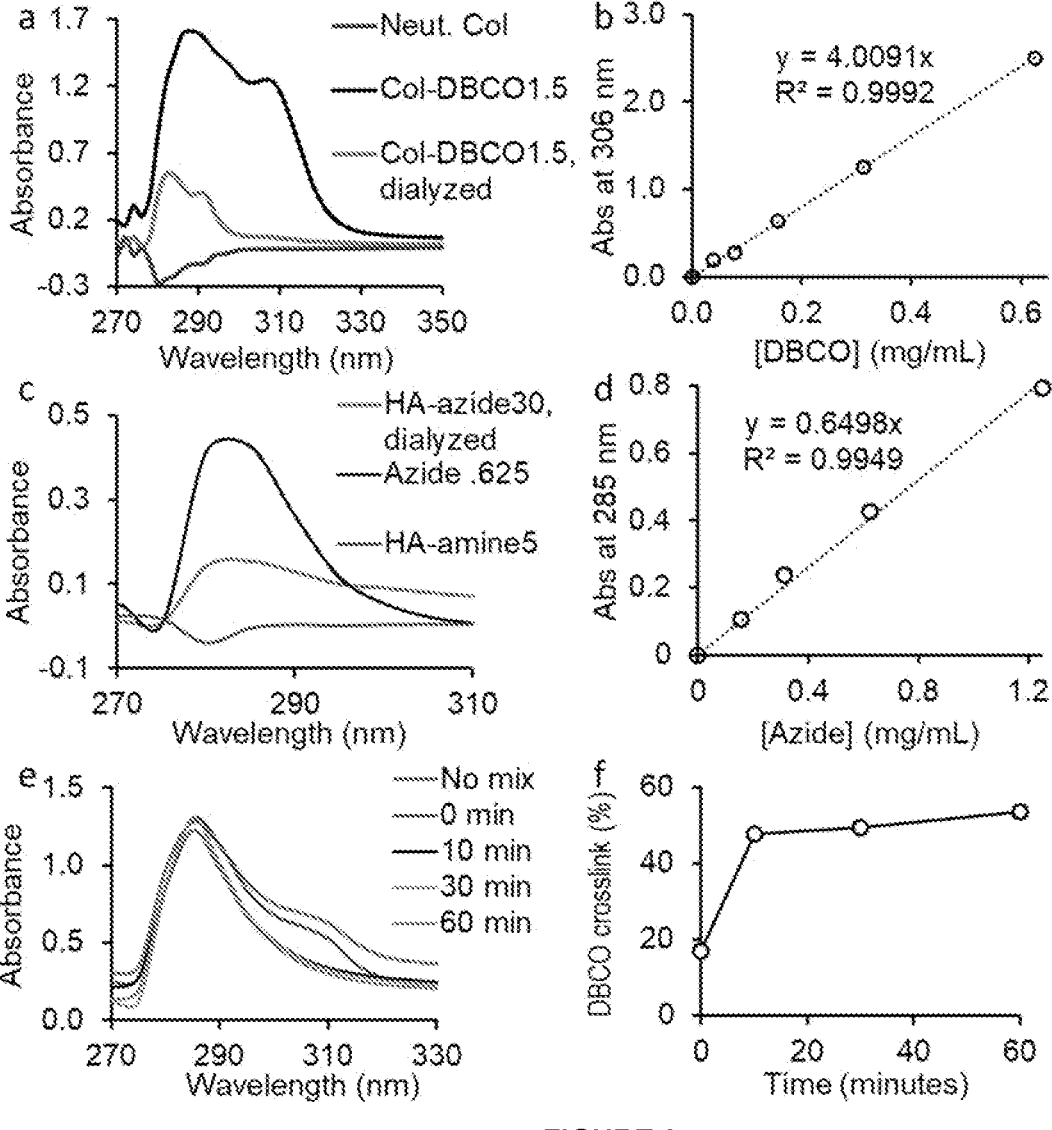
FIG. 9. Quantification of conjugated azido and DBCO. (a) Absorbance spectra of 3 mg/mL unconjugated collagen (Blue) and 1.5 mg/mL Col-DBCO before (Black) and after (Red) dialysis. Col-DBCO showed intense absorbance peaks at approximately 290 and 306 nm while collagen did not. (b) DBCO concentration was linearly dependent on the absorbance at 306 nm. (c) Absorbance spectra of 5 mg/mL unconjugated HA-amine, 30 mg/mL HA-azide after dialysis, and 0.625 mg/mL azide. (d) Azide concentration was linearly dependent on the absorbance at 285 nm. (e) DBCO featured absorbance at 310 nm decreased dramatically upon mixing Col-DBCO with HA-azide and continued to decrease for one hour, which indicated the crosslinking between DBCO and azide. (f) Quantification of crosslinked DBCO over time.

On the other side, both HA-azide and Col-DBCO were transparent, which is the reason why they formed much transparent hydrogel than HA-DBCO and Col-azide (FIG. 7b). Hence, we chose the first strategy to make hyaluronate-collagen copolymeric hydrogel (FIG. 8). Specifically, the amidated hyaluronate and collagen were modified with azido and DBCO respectively via N-hydroxysuccinimidyl ester assisted amide reaction (FIG. 8 a, b). Conjugation of DBCO and azido were quantified with UV-vis absorbance spectra. DBCO has intense absorbance peaks at approximately 290 and 310 nm while collagen does not (FIG. 9a). As shown in FIG. 9b, there was a linear relationship between the DBCO concentration and its absorbance at 306 nm. We calculated the conjugated DBCO on Col-DBCO and found that there were 12.5±7.1 nmol conjugated DBCO per mg of Col-DBCO. The primary amine groups per collagen was calculated to be approximately 269 nmol/mg collagen.[8] Therefore, the degree of substitution of DBCO was 4.63%. Similarly, the azide has a featured absorbance peak at around 285 nm, and it is linearly dependent on the azide concentrations (FIG. S2c, d). There were 19.6±2.5 nmol conjugated azido per mg of HA-azide and the degree of substitution of azido was 1.66%.

The dialyzed HA-azide was then mixed with Col-DBCO, crosslinked through SPAAC reaction, and produced the hyaluronate-collagen copolymer-based hydrogel (FIG. 8c). The absorbance at 310 nm dropped dramatically upon mixing of HA-azide and Col-DBCO (FIG. 9e), which was likely due to the crosslinking between DBCO and azide and therefore decreased free DBCO. This result indicated that the SPAAC reaction happened as soon as the gel components were mixed. Further analysis of the absorbance changes showed that 17%, 48%, 50%, and 54% of DBCO crosslinked within 0, 10, 30, and 60 minutes (FIG. 9f).

Figure 10:
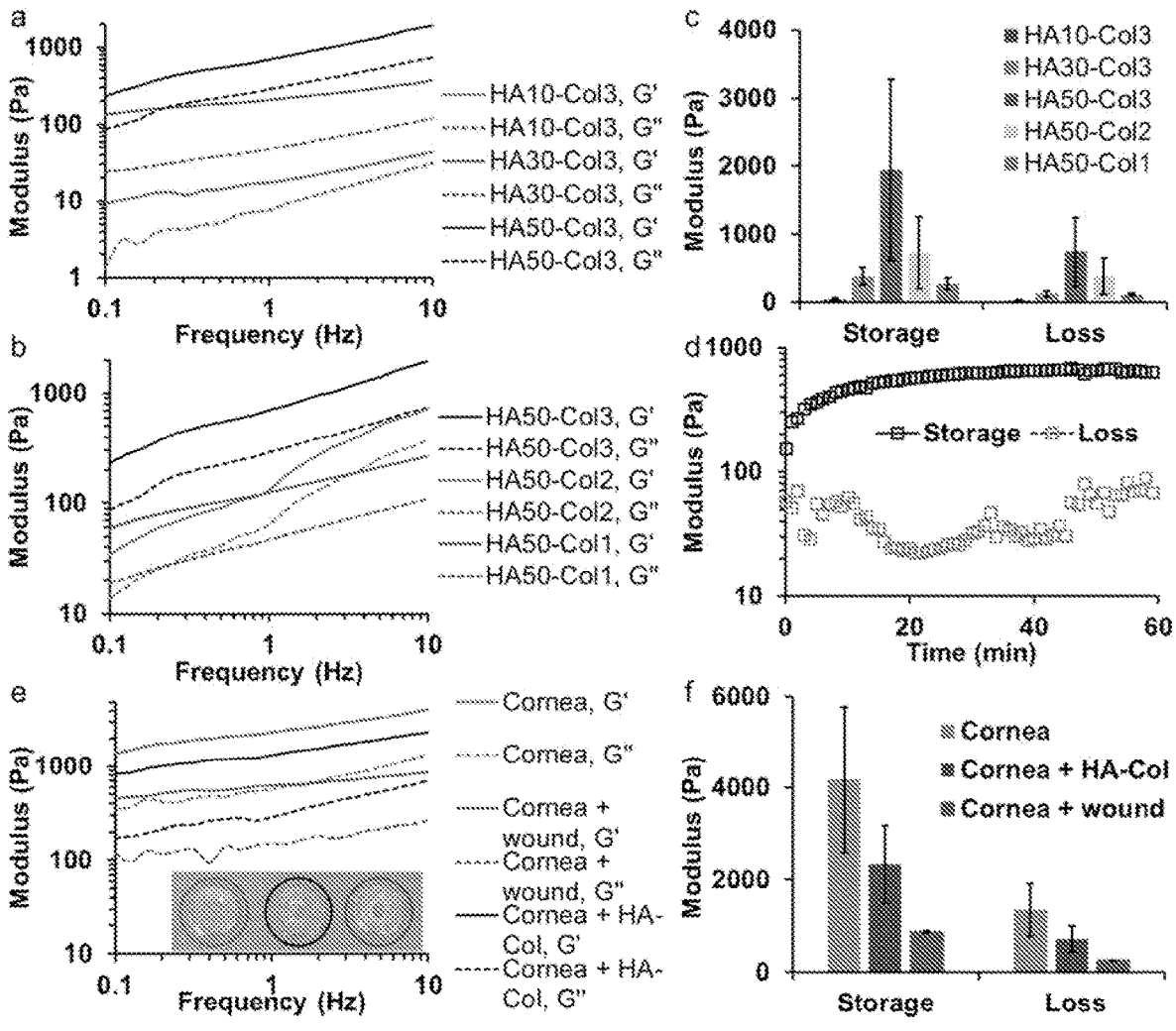
FIG. 10 Mechanical properties of hyaluronate-collagen copolymeric hydrogels. (a & b) Storage and loss moduli of copolymeric hydrogels increased as the sweeping frequency increased. The samples had different (a) hyaluronate and (b) collagen content. G' is storage modulus and G" is loss modulus. HA & Col present hyaluronate and collagen, and the numbers are the initial polymer concentration in mg/mL. The polymers were mixed at a 1:1 volume ratio. (c) Hydrogel with 25 mg/mL hyaluronate and 1.5 mg/mL collagen (HA50-Col3) showed the highest storage and loss moduli at sweeping frequency 10 Hz. (d) Dynamic moduli of copolymeric hydrogel HA50-Col3 as a function of time at the beginning of gelation. (e) Storage and loss moduli of intact and wounded cornea buttons as well as wounded cornea button with the strongest hydrogel from (c). (f) The copolymeric hydrogel HA50-Col3 increased the storage and loss moduli of wounded cornea greatly.

Physical and optical properties of copolymeric hydrogels. We studied the mechanical properties of the copolymeric hydrogel with different polymer contents by mixing 10, 30, or 50 mg/mL HA-azide with 1, 2, or 3 mg/mL Col-DBCO at 1:1 volume ratio. The highest initial Col-DBCO concentration was set at 3 mg/mL which led to a final collagen concentration of 1.5 mg/mL because according to our previous study, the collagen concentration at 1.5 mg/mL was superior for re-epithelialization on cornea than higher concentrations.[8] When the Col-DBCO was kept at 3 mg/mL, storage and loss moduli of hydrogels increased as the HA-azide increased from 10 to 50 mg/mL (FIG. 10a). Similarly, both moduli also increased when the Col-DBCO content increased from 1 to 3 mg/mL but HA-azide kept at 50 mg/mL (FIG. 10b). The hyaluronate content was kept below 50 mg/mL to achieve a high water content (>97%), which is good for matter exchange.

Noticeably, the hydrogel with 15 mg/mL HA-azide and 1.5 mg Col-DBCO (HA30-Col3) showed higher storage and loss moduli than hydrogel with 25 mg/mL HA-azide and 0.5 mL Col-DBCO (HA50-Col1), even though the first hydrogel had a lower polymer concentration (FIG. 10c). UV-vis absorbance spectra showed that HA30-Col3 had 295 nmol/mL azido and 385 nmol/mL DBCO; and HA50-Col1 had 491 nmol/mL azido and 128 nmol/mL DBCO. This indicated that HA30-Col3 had larger degree of crosslinking than HA50-Col1. Therefore, the hydrogel's moduli depended not solely on the polymer content but more significantly on the degree of crosslinking.

The strongest hydrogel (HA50-Col3), with an average storage and loss moduli were 1945 and 742 Pa respectively, contained 25 mg/mL hyaluronate and 1.5 mg/mL collagen, which equaled to 2.65% polymers and 97.35% water (FIG. 10c). Its azido-to-DBCO ratio was approximately 1.3. The excess azido related to DBCO could speed up the SPAAC reaction.[15] In situ rheology studies indicated that the copolymeric hydrogel started to form before the starting point of rheology measurement because the measured storage modulus was already higher than the loss modulus. The storage modulus reached half maximum in approximately 3 minutes and plateaued in approximately 40 minutes (FIG. 10d). This duration is suitable for an in-situ gel application procedure.

We also compared the mechanical properties of the strongest hydrogel HA50-Col3 with rabbit cornea. To exclude the negative effect of broken collagen fibrils,[16] we used intact cornea button (red circled) and wounded cornea button (blue circled) as positive and negative controls, as shown in FIG. 10e (inset). The storage and loss modulus of all samples increased as sweeping frequency increased (FIG. 10e). Both the storage and loss modulus of wounded cornea button were around 20% of the intact cornea button, while they increased to around 55% when the wound was filled with the strongest hydrogel (HA50-Col3), as shown in FIG. 10f.

Figure 11:
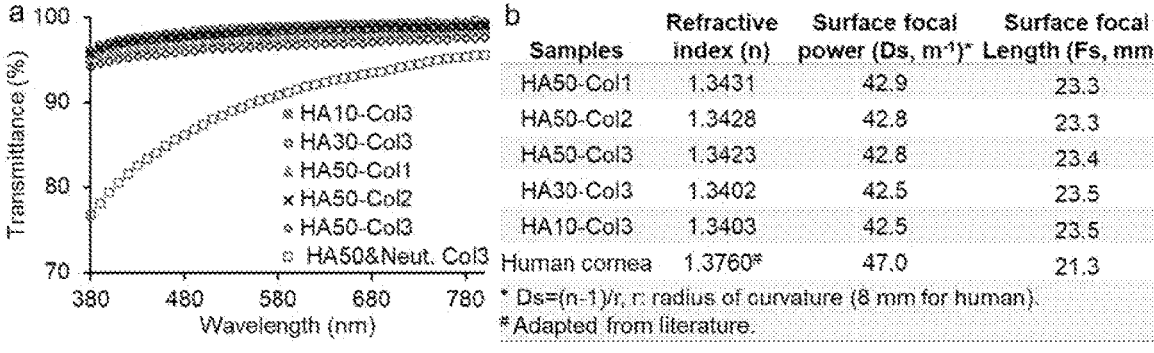
FIG. 11 Optical properties of hyaluronate-collagen copolymeric hydrogels. (a) Transmittance of SPAAC crosslinked hyaluronate-collagen copolymeric hydrogels were much higher than non-crosslinked hydrogel (HA50&Neut. Col3). (b) Refractive index, surface focal power, and surface focal length of the hydrogels.

The hyaluronate-collagen copolymeric hydrogels also showed excellent optical properties for cornea stromal substitute. First, higher transparency is desired to let more light penetrate the cornea substitute and enter the patient's eye. According to literature, the human cornea has a transmittance over 95% in the spectral range from 380 and 800 nm, which is due to the highly ordered assembly of collagen fibrils. The hydrogels we developed in this work had high transparency that was comparable to the cornea: all the hyaluronate-collagen copolymeric hydrogels with different polymer contents showed a transmittance over 94% from 380 nm to 410 nm and over 95% between 410 nm and 800 nm (FIG. 11a). As a control, the mixture of 25 mg/mL hyaluronate-azide and 1.5 mg/mL collagen without DBCO had a much lower transmittance-lower than 80% between 380 nm and 410 nm (FIG. 11a). Hence, the high transparency of hyaluronate-collagen copolymeric hydrogel was due to the SPAAC crosslinking between hyaluronate and collagen.

Another crucial optical property of the cornea substitute is its focal power, which is defined as the reciprocal of focal length and indicates the degree to which the cornea substitutes converges light. The average total corneal power of human normal eyes is around 43 m$^{-1}$. The cornea surface power was determined by the corneal curvature radius and refractive index. The average refractive index of human cornea is reported to be 1.376. The refractive index of the hyaluronate-collagen copolymeric hydrogel ranges from 1.340 to 1.343, as listed in the FIG. 11b. The surface focal power of the hydrogels was calculated using 8 mm as radius of curvature. Results showed that the focal power of hydrogels were slightly lower than the human cornea and the focal length differences between the hydrogels and human cornea was around 2 mm. (FIG. 11b).

Figure 12:
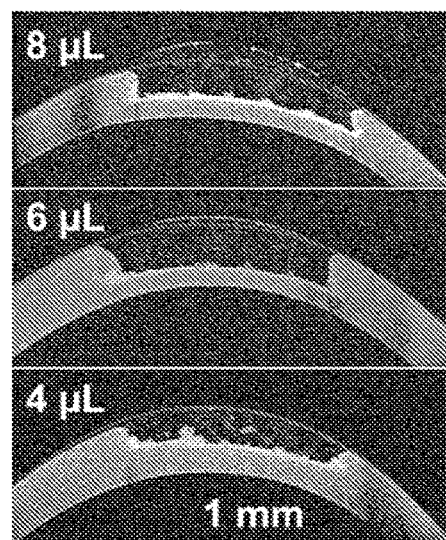
FIG. 12 OCT images of copolymeric hydrogel HA50-Col3 filled keratectomy area. The red curves were added for eye guidance. The curvature of central cornea decreased as more hydrogel was added, and it could be restored with approximately 5 µL hydrogel.

The lower refractive index of the gel will lead to underpower of corneal surface if the gel assumes the same contour as the host's normal cornea. The focal power or focal length can be matched to naïve cornea by changing the radius curvature. Ex vivo optical coherence tomography (OCT) showed that the curvature of central cornea could be adjusted by changing the volume of applied hydrogel (FIG. 12). The decreased radius curvature could compensate the slightly lower refractive index of the hydrogel to get the same focal length. Moreover, given that the gel can be used in conjunction with a contact lens, this underpowering can be overcome with either a higher power contact lens (e.g. 1.0-5.0 diopters), or by a modified base curve of the contact lens to form a steeper or flatter curvature to the gel as it is formed. Furthermore, additives can be included in the gel to increase its refractive index; if that additive is a stromal cells (e.g. keratocytes), then the refractive index of the gel may increase over time as certain biomolecules are produced by those cells, such as the corneal crystallin aldehyde dehydrogenase 3A1 (ALDH3A).

Figure 13:
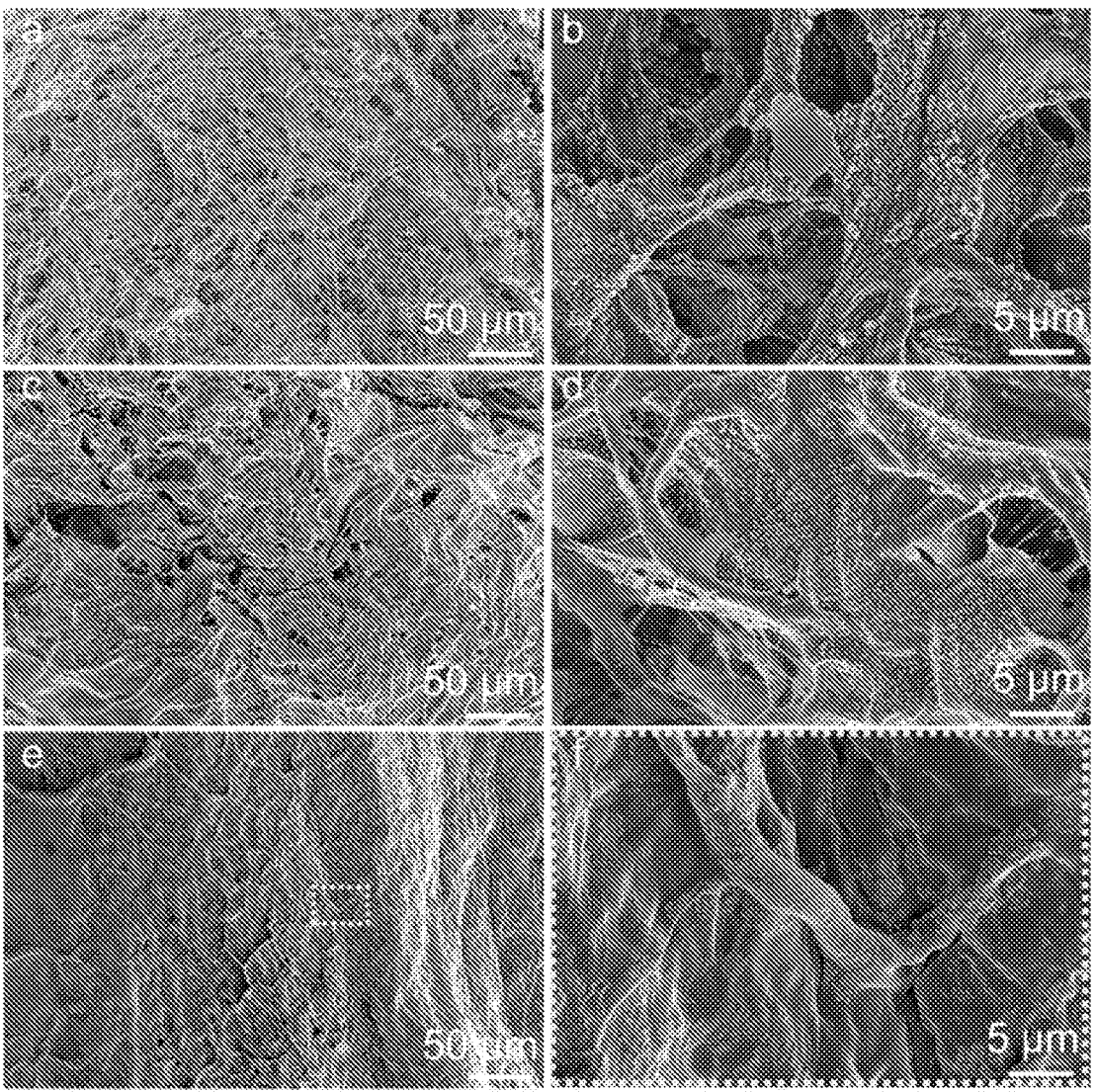
FIG. 13. Morphology and integration of the HA50-Col3 hydrogel. SEM images of (a, b) HA50-Col3 hydrogel, (c, d) corneal stroma, and (e, f) HA50-Col3 hydrogel filled corneal stroma. The red line in (e) roughly showed the interface between hydrogel and the corneal stroma. (f) showed the higher magnification image of the dotted area in (e) and there is no detectable gap or separation between the hydrogel and the adjacent cornea, which indicates physical apposition between the gel and the corneal stroma.

Morphology and biointegration of copolymeric hydrogel HA50-Col3. The mechanical and optical properties of the copolymeric hydrogels indicated the best hydrogel had 1.5 mg/mL collagen, which was also the most ideal for re-epithelialization on cornea. Therefore, we focused on this HA50-Col3 hydrogel for all the other tests. First, we studied the morphology of this hydrogel and its integration with corneal stromal tissues. SEM images showed that the hydrogel had a porous structure constituted by polymeric filaments (FIG. 13a, b), which was similar to the morphology of rabbit corneal stroma (FIG. 13c, d). Moreover, the hydrogel filled the corneal wound without any detectable fissures after magnified 5,000 times (FIG. 13*e, f*), which bodes well for the hydrogel's potential for biointegration with corneal stroma.

Biocompatibility and Re-Epithelialization Capacity of Copolymeric Hydrogel HA50-Col3

Figure 14:
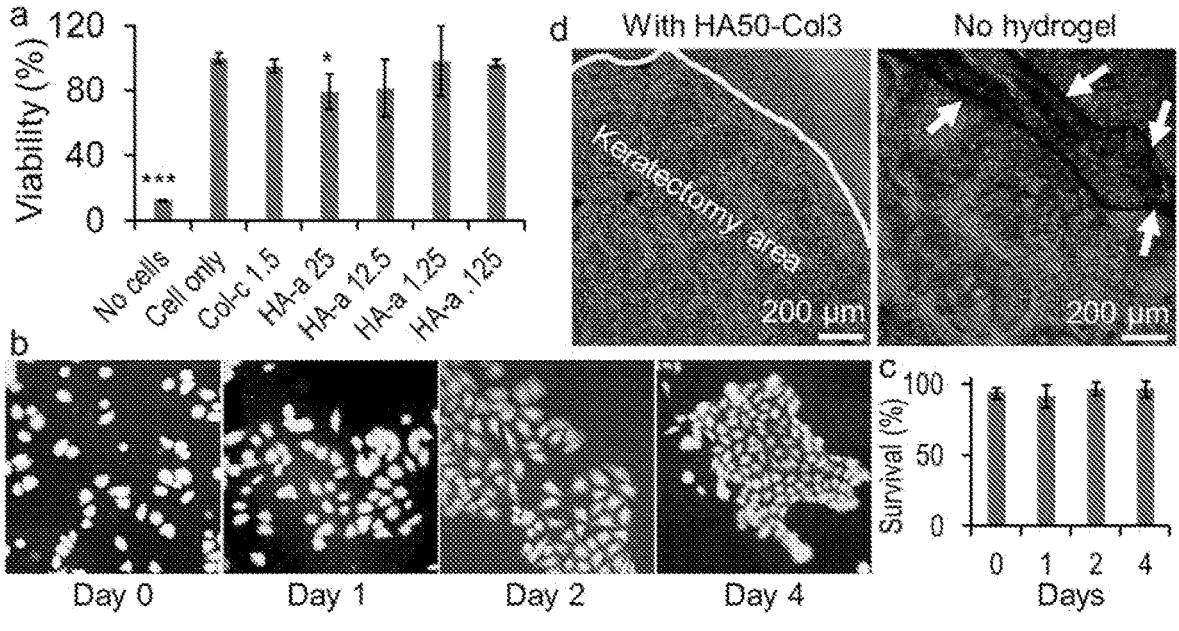
FIG. 14. Biocompatibility and re-epithelialization capacity of HA50-Col3 hydrogel to corneal epithelial cells. (a) Cell viability assay showed that collagen-DBCO 1.5 mg/mL (Col-c 1.5) were biocompatible. The HA-azide at low concentrations were biocompatible but HA-azide at 25 mg/mL (HA-a 25) decreased the cell viability to 80%. The decrease is significant when compared to the cell only group. (* p<0.05, *** p<0.005, 2-tail homoscedastic t-test). The error bars represent standard deviation of four replicates. (b) In vitro live/dead assay showed that corneal epithelial cells could grow on top of the HA50-Col3 with a high survival. The hydrogel was modified with Alexa Fluor 647 (blue). Green and red showed living and dead cells. (c) Quantification of cell survival on top of HA50-Col3 hydrogel on different days based on the live/dead assay. Error bars represents standard deviations of at least five fields of views from different replicates. (d) Top view of wounded cornea treated with and without HA50-Col3 hydrogel application in an ex vivo organ culture model of sutureless anterior lamellar keratoplasty. HA50-Col promoted the re-epithelialization. The hydrogel was modified with Alexa Fluor 647 and shown in red. Green and blue showed the F-actin and nuclei respectively. The white arrows pointed at the gap on the wounded cornea, which indicated no epithelial cells.

Next, we studied the biocompatibility of hydrogel on corneal epithelial cells. Although hyaluronate and collagen are non-toxic to human, the functional groups might be less well tolerated. A resazurin based viability assay showed that collagen-DBCO at 1.5 mg/mL was biocompatible to cells, while the hyaluronate-azide at 25 mg/mL decreased the cell viability to 80%, the hyaluronate-azide at lower concentrations however did not show any significant toxicity (FIG. 14*a*). The decreased biocompatibility of 25 mg/mL HA-azide is likely due to the extremely high dose of the dangling azido (490 $\mu$mol/L). The biocompatibility of 25 mg/mL HA-azide should be increased dramatically once they have crosslinked with DBCO.

To verify our hypothesis, we tested the biocompatibility of HA50-Col3 with Calcein AM/Ethidium homodimer-I live/dead assay on different days. Very few dead cells were seen after the corneal epithelial cells were incubated on the hydrogel for 4 days, and the living cells were spreading on the top of gel (FIG. 14*b*). The survival of corneal epithelial cells on the hydrogel was 93.3%±3.7%, 91.3%±8.1%, 96.4%±4.6%, and 96.3%±5.5% on day 0, 1, 2, and 4 (FIG. 14*c*). There was no significant decrease of survival over this time period, indicating excellent biocompatibility of HA50-Col3.

The HA50-Col3 hydrogel was found to be able to support the re-epithelialization of cornea in an ex vivo organ culture study. We performed an anterior lamellar keratoplasty on nucleated rabbit eyes and filled the defects with the gels, forming them in situ on the wound bed. The epithelium on the keratectomy area was completely removed and a superficial layer of stroma was removed. Then, the wound was filled with the hydrogel HA50-Col3 immediately after mixed the HA-azide 50 mg/mL and Col-DBCO 3 mg/mL at a 1:1 volume ratio. To better visualize the hydrogel, we modified the HA-azide with a fluorophore (Alexa Fluor 647). FIG. 14*d* shows top view fluorescence images of the wounded corneas treated with and without hydrogel. The hydrogel (red) was almost completely covered by cells (green) after four days incubation while multiple gaps were seen on the wounded cornea without hydrogel (FIG. 14*d*). The sections showed that the HA50-Col3 hydrogel promoted re-epithelialization on the wounded cornea.

Figure 15:
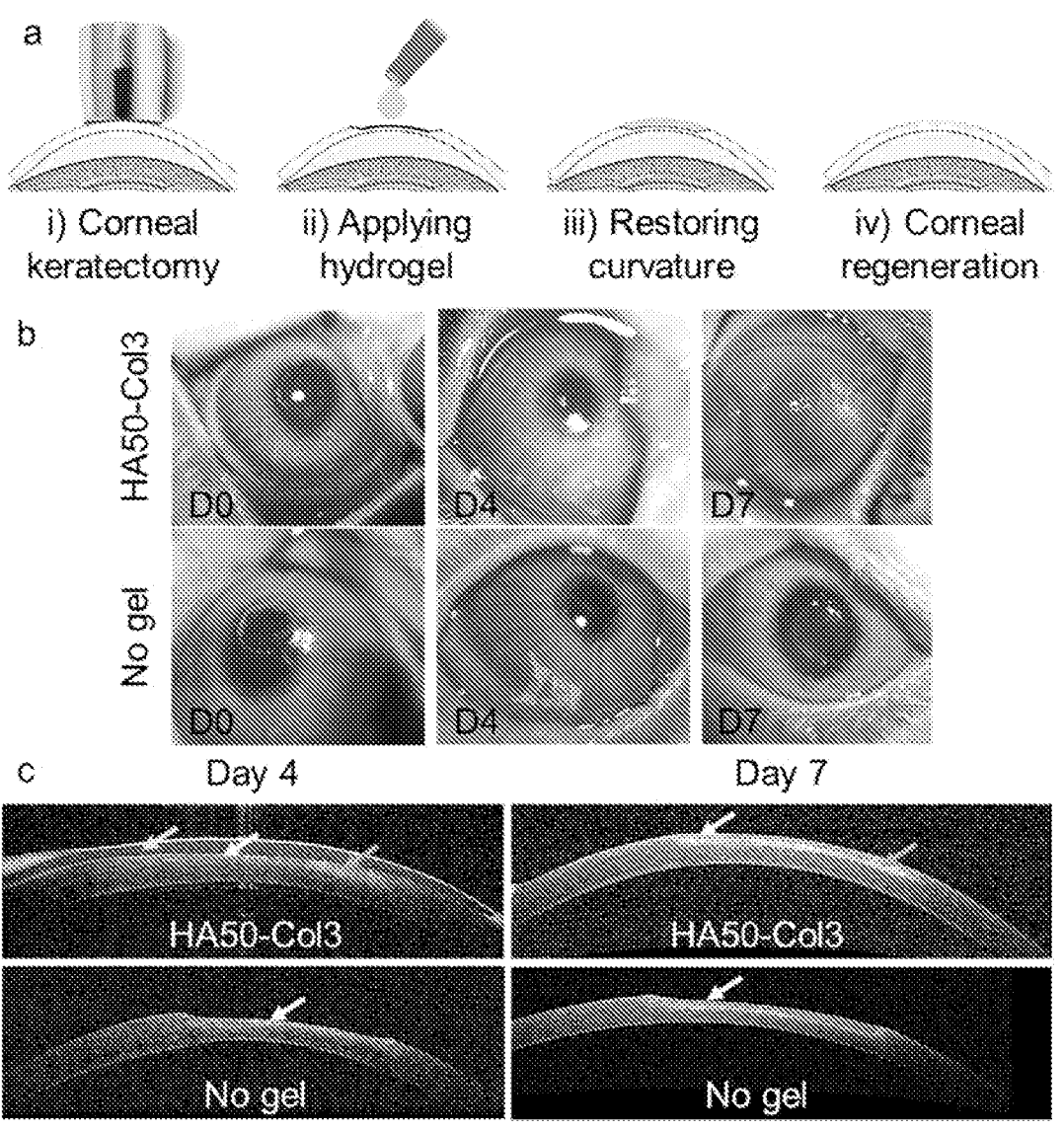
FIG. 15 Application of hydrogel for sutureless repair of corneal wound. (a) Scheme of the disease model and treatment. The corneal wound was created by anterior partial stromal keratectomy via a customized 3.5 mm vacuum trephine. (b) Follow up photos of the rabbit eyes after in vivo keratectomy and gel application. (c) Follow-up examination of rabbits' eyes with in vivo OCT. A contact lens was used to protect the hydrogel from scratching by the animal. The hydrogel HA50-Col3 restored the central corneal curvature.

In vivo assessment of HA50-Col3 copolymeric hydrogel in a rabbit anterior lamellar keratoplasty model. To further understand the effect of copolymeric hydrogel on corneal wound healing, in vivo studies were performed with a corneal wound model of anterior lamellar keratectomy in rabbits (FIG. 15*a*). First, the cornea was wounded with a customized 3.5 mm vacuum trephine on the central cornea (FIG. 15*b*). The wound depth was controlled to be approximately 60%±9% (n=11) of the corneal central thickness. Then, the copolymeric hydrogel HA50-Col3 were added into the wound immediately after mixing the HA-azide and Col-DBCO. We added 5 $\mu$L of the mixture to the wound because ex vivo optical coherence tomography (OCT) showed that the curvature of cornea could be restored with approximately 5 $\mu$L hydrogel. The gel was still clear on the wounded cornea 7 days after gel application (FIG. 15*b*).

In vivo OCT showed that the wounded cornea applied with HA50-Col3 had a smooth connection between the keratectomy area and adjacent normal cornea and the corneal curvature was completely restored after one week (FIG.

15*c*). On the contrary, without gel application, the keratectomy area was thinner than the adjacent cornea and showed a dip in the central cornea (FIG. 15*c*). Noticeably, there were two layers (approximately 30 and 90 $\mu$m) on the central corneal stroma on day 7 for the cornea applied with HA50-Col3. However, for the wounded cornea without hydrogel application, a thin layer (approximately 50 $\mu$m) was seen on top of the central cornea on day 4 and it became thickened (approximately 100 $\mu$m) on day 7 (FIG. 15*c*).

Figure 16:
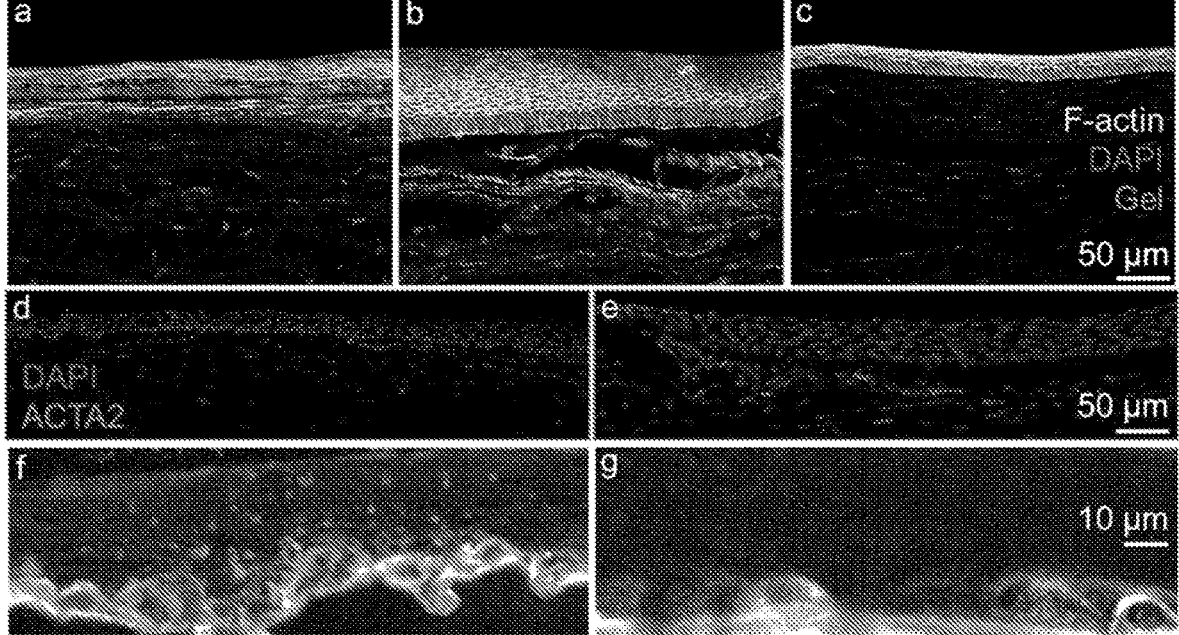
FIG. 16 Immunofluorescence staining of wounded cornea treated with and without hydrogel HA50-Col3. F-actin staining of wounded cornea treated with HA50-Col3 (a), wounded cornea (b), and normal cornea (c). The results showed that the HA50-Col3 effectively promoted the regeneration of epithelium without abnormal activation of keratocytes. α-SMA staining of wounded cornea treated with (d) and without (e) HA50-Col. The α-SMA staining indicated that HA50-Col3 prohibited the massive expression of α-SMA and could prevent the fibroblast formation and corneal scarring. ZO-1 staining of wounded cornea treated with (f) and without (g) HA50-Col, which showed that the HA50-Col3 promoted the tight junction formation on the regenerated epithelium.

Immunofluorescence staining of the cornea section showed that the two layers on cornea applied with HA50-Col3 were regenerated epithelium and hydrogel respectively (FIG. 16*a*) and that the layer on the cornea without hydrogel application was hyperplastic epithelium alone (FIG. 16*b*). On day 7, the hydrogel (modified with fluorophore) was observed underneath of epithelial cell layers. There were 5-8 layers of epithelial cells, among which the lower layer showed cuboidal basal cells and the upper layer showed flattened superficial cells (FIG. 16*a*), which is the structure of normal epithelium (FIG. 16*c*). Without the hydrogel, epithelial hyperplasia was observed, where the epithelium was much thicker than normal and showed 15-20 layers of epithelial cells (FIG. 16*b*). This is the expected physiological wound healing response to a keratectomy wound or ulcer in vivo. Meanwhile, the keratocytes in the keratectomy area were more activated than normal cornea and wounded cornea treated with the hydrogel.

Immunofluorescence staining of alpha smooth muscle actin ($\alpha$-SMA) showed that the wounded cornea without hydrogel treatment had much more $\alpha$-SMA expressed at the wound edge than the HA50-Col3 treated one (FIG. 16*d&e*). It is likely that keratocytes close to the wound surface were activated and differentiated into $\alpha$-SMA-positive myofibroblasts in the wounded cornea. However, HA50-Col3 significantly decreased the expression of $\alpha$-SMA, which was ideal for avoiding myofibroblast formation and corneal scarring. Immunofluorescence staining of zonula occludens-1 (ZO-1) showed a higher expression of ZO-1 in HA50-Col3 treated cornea than the no gel control (FIG. 16*f&g*). We could conclude that the HA50-Col3 did not cause a significant myofibroblast activation and promoted tight junction on the regenerated epithelial cells, which are promising attributes for a corneal stroma substitute candidate material.

Here, we report on the development of a bio-orthogonally crosslinked collagen-hyaluronate copolymeric hydrogel and its in vitro and in vivo performance as an in situ-forming substitute for corneal stroma. The hydrogel consisted of 97% water and was highly transparent. The material exhibited significantly improved mechanical properties compared to our previously reported SPAAC-crosslinked collagen-only hydrogel. The hyaluronate-collagen copolymeric hydrogel showed similar morphology to corneal stroma, and although its refractive index is lower than that of native cornea, it has potential to improve vision due to the clear, smooth anterior curvature that it forms on corneal wound beds as well as the ability to modulate that curvature during gelation. Its gelation time on the order of minutes is suitable for therapeutic uses for both point-of-care situations as well as in the operating room. The material crosslinks under ambient, aqueous conditions, requires no light irradiation or any other type of trigger or initiator, and fills stromal defects without the need for sutures. This hydrogel also demonstrated excellent biocompatibility and support for epithelialization in vivo. Future studies are merited to understand the material's capacity to provide functional vision in the treatment of vision-threatening corneal defects.

REFERENCES

1. Islam, M. M.; Buznyk, O.; Reddy, J. C.; Pasyechnikova, N.; Alarcon, E. I.; Hayes, S.; Lewis, P.; Fagerholm, P.; He, C.; lakymenko, S.; Liu, W.; Meek, K. M.; Sangwan, V. S.; Griffith, M., Biomaterials-enabled cornea regeneration in patients at high risk for rejection of donor tissue transplantation. npj Regenerative Medicine 2018, 3 (1), 2.
2. Gain, P.; Jullienne, R.; He, Z. G.; Aldossary, M.; Acquart, S.; Cognasse, F.; Thuret, G., Global Survey of Corneal Transplantation and Eye Banking. Jama Ophthalmology 2016, 134 (2), 167-173.
3. Dana, M. R.; Qian, Y.; Hamrah, P., Twenty-five-Year Panorama of Corneal Immunology: Emerging Concepts in the Immunopathogenesis of Microbial Keratitis, Peripheral Ulcerative Keratitis, and Corneal Transplant Rejection. Cornea 2000, 19 (5), 625-643.
4. Palanker, D., Optical Properties of the Eye. AAO One Network 2013.
5. Sani, E. S.; Kheirkhah, A.; Rana, D.; Sun, Z. M.; Foulsham, W.; Sheikhi, A.; Khademhosseini, A.; Dana, R.; Annabi, N., Sutureless repair of corneal injuries using naturally derived bioadhesive hydrogels. Science Advances 2019, 5 (3).
6. Mobaraki, M.; Abbasi, R.; Omidian Vandchali, S.; Ghaffari, M.; Moztarzadeh, F.; Mozafari, M., Corneal Repair and Regeneration: Current Concepts and Future Directions. Frontiers in Bioengineering and Biotechnology 2019, 7 (135).
7. Li, L.; Lu, C.; Wang, L.; Chen, M.; White, J.; Hao, X.; McLean, K. M.; Chen, H.; Hughes, T. C., Gelatin-Based Photocurable Hydrogels for Corneal Wound Repair. ACS Appl Mater Interfaces 2018, 10 (16), 13283-13292.
8. Lee, H. J.; Fernandes-Cunha, G. M.; Na, K.-S.; Hull, S. M.; Myung, D., Bio-Orthogonally Crosslinked, In Situ Forming Corneal Stromal Tissue Substitute. Advanced Healthcare Materials 2018, 7(19), 1800560.
9. Neuman, M. G.; Nanau, R. M.; Oruha-Sanchez, L.; Coto, G., Hyaluronic acid and wound healing. Journal of Pharmacy & Pharmaceutical Sciences 2015, 18 (1), 53-60.
10. Zhong, J.; Deng, Y.; Tian, B.; Wang, B.; Sun, Y.; Huang, H.; Chen, L.; Ling, S.; Yuan, J., Hyaluronate acid-dependent protection and enhanced corneal wound healing against oxidative damage in corneal epithelial cells. Journal of ophthalmology 2016, 2016.
11. Lee, H. J.; Fernandes-Cunha, G. M.; Myung, D., In situ-forming hyaluronic acid hydrogel through visible light-induced thiol-ene reaction. React. Funct. Polym. 2018, 131, 29-35.
12. Mercado, C.; Welling, J.; Olivaq, M.; Li, J.; Gurung, R.; Ruit, S.; Tabin, G.; Chang, D.; Myung, D., Clinical Application of a Smartphone-Based Ophthalmic Camera Adapter in Under-Resourced Settings in Nepal. Journal of Mobile Technology in Medicine 2017, 6 (3), 34-42.
13. Hodgson, S. M.; Bakaic, E.; Stewart, S. A.; Hoare, T.; Adronov, A., Properties of Poly(ethylene glycol) Hydrogels Cross-Linked via Strain-Promoted Alkyne-Azide Cycloaddition (SPAAC). Biomacromolecules 2016, 17(3), 1093-1100.
14. Jang, J.; Kim, T. G.; Kim, B. S.; Kim, S.-W.; Kwon, S.-M.; Cho, D.-W., Tailoring mechanical properties of decellularized extracellular matrix bioink by vitamin B2-induced photo-crosslinking. Acta Biomater. 2016, 33, 88-95.

15. Madl, C. M.; Katz, L. M.; Heilshorn, S. C., Bio-Orthogonally Crosslinked, Engineered Protein Hydrogels with Tunable Mechanics and Biochemistry for Cell Encapsulation. Adv. Funct. Mater. 2016, 26 (21), 3612-3620.
16. Depalle, B.; Qin, Z.; Shefelbine, S. J.; Buehler, M. J., Influence of cross-link structure, density and mechanical properties in the mesoscale deformation mechanisms of collagen fibrils. Journal of the mechanical behavior of biomedical materials 2015, 52, 1-13.
17. Wang, L.; Mahmoud, A. M.; Anderson, B. L.; Koch, D. D.; Roberts, C. J., Total Corneal Power Estimation: Ray Tracing Method versus Gaussian Optics Formula. Investigative Ophthalmology & Visual Science 2011, 52 (3), 1716-1722.
18. Olsen, T., On the Calculation of Power from Curvature of the Cornea. Br. J. Ophthalmol. 1986, 70 (2), 152-154.
19. Yazdani, M.; Shahdadfar, A.; Jackson, C. J.; Utheim, T. P., Hyaluronan-Based Hydrogel Scaffolds for Limbal Stem Cell Transplantation: A Review. Cells 2019, 8 (3).
20. Lee, H. J.; Fernandes-Cunha, G. M.; Putra, I.; Koh, W.-G.; Myung, D., Tethering Growth Factors to Collagen Surfaces Using Copper-Free Click Chemistry: Surface Characterization and in Vitro Biological Response. ACS Applied Materials & Interfaces 2017, 9 (28), 23389-23399.
21. Barile, M.; Valenti, D.; Hobbs, G. A.; Abruzzese, M. F.; Keilbaugh, S. A.; Passarella, S.; Quagliariello, E.; Simpson, M. V., Mechanisms of toxicity of 3'-azido-3'-deoxythymidine: its interaction with adenylate kinase. Biochem. Pharmacol. 1994, 48 (7), 1405-1412.
22. Nishimura, T.; Toda, S.; Mitsumoto, T.; Oono, S.; Sugihara, H., Effects of Hepatocyte Growth Factor, Transforming Growth Factor-$\beta$1 and Epidermal Growth Factor on Bovine Corneal Epithelial Cells under Epithelial-Keratocyte Interaction in Reconstruction Culture. Experimental Eye Research 1998, 66 (1), 105-116.
23. Chen, J.; Li, Z.; Zhang, L.; Ou, S.; Wang, Y.; He, X.; Zou, D.; Jia, C.; Hu, Q.; Yang, S.; Li, X.; Li, J.; Wang, J.; Sun, H.; Chen, Y.; Zhu, Y. T.; Tseng, S. C. G.; Liu, Z.; Li, W., Descemet's Membrane Supports Corneal Endothelial Cell Regeneration in Rabbits. Sci Rep 2017, 7 (1), 6983.
24. Sugrue, S. P.; Zieske, J. D., ZO1 in Corneal Epithelium: Association to the Zonula Occludens and Adherens Junctions. Experimental Eye Research 1997, 64 (1), 11-20.

Example 3

In Situ-Forming Collagen Hydrogel Crosslinked Via Multi-Functional PEG as a Matrix Therapy for Corneal Defects Corneal injuries collectively represent a major global human health challenge, affecting hundreds of millions of people each year. Unfortunately, less than 2% of patients who could benefit from a sight-restoring corneal transplant have access to cadaveric donor corneal tissue. Thus, there is a critical need for new ways to repair corneal defects that drive proper epithelialization and stromal remodeling of the wounded area without the need for cadeveric donor corneas. Emerging therapies for corneal adhesives are being explored and they focus on addressing the current problems: transparency, biocompatibility, patient comfort, and biointegration. Herein, we report on the development of an in situ-forming hydrogel of collagen type I crosslinked via multi-functional polyethylene glycol (PEG)-N-hydroxysuccinimide (NHS) and characterize its biophysical properties and regenerative capacity both in vitro and in vivo. The hydrogels form under ambient conditions within minutes upon mixing without the need for an external catalyst or trigger such as light or heat, and their degradability and stiffness were tuned by changing the functionality and concentration of PEG. PEG functionality did not affect transparency, but high PEG concentration decreased hydrogel transparency before and after swelling. In addition, in situ-forming collagen-PEG hydrogels allowed corneal cells to migrate and proliferate on their surface. In vivo studies in which the hydrogels were applied to stromal keratectomy wounds without sutures showed that they supported the overgrowth of epithelial cells, while the ingrowth of stromal cells was achieved depending on the hydrogel PEG functionality. Overall, the in situ forming collagen-PEG hydrogels had desirable physical and biological properties to be used as a corneal stromal defect wound repair matrix that could be applied without the need for sutures or an external trigger such as a catalyst or light energy.

Collagen based hydrogels are particularly attractive as ocular adhesives because is the most abundant protein in mammals, is naturally present in corneal stroma and is the main structural protein in the extracellular environment. However, the mechanical properties of collagen must be adjusted by crosslinking with synthetic or natural polymers using chemical crosslinking strategies for it to be applied to the cornea. The major drawback of changing collagen mechanical properties is the cytotoxicity of either the crosslinker applied or the small molecules released after scaffold formation and degradation.

Crosslinking collagen with multi-arm PEG using N-hydroxysuccinimide (NHS) chemistry aiming corneal adhesives can be advantageous because the reaction and the released substances are biocompatible. For instance, the FDA has approved ReSure®—an (NHS)-terminated 4-arm PEG prepolymer that reacts with the primary amines of trilysine-leading to in situ gelation. In other work, a collagen has been crosslinked via multifunctional PEG and has been shown to support cell growth. Given its track record as a crosslinking chemistry for an ophthalmic sealant for corneal incisions, succinimide active ester reaction with primary amines was given consideration here to facilitate adhesion to a stromal wound bed. We have chosen to develop collagen gels using multi-functional PEG succinimide esters as an in situ-forming, suture-free, and catalyst-free scaffold to promote epithelial overgrowth and stromal remodeling in the treatment of corneal defects.

Methods

Fabrication of collagen-PEG and non-crosslinked collagen hydrogels. Type I bovine collagen (Thermo Fisher Scientific; A1064401) was first pH neutralized using a solution of 1.0 M sodium hydroxide solution, deionized (DI) water, and 10×PBS in a 3:57:20 ratio. The 5 mg/mL collagen solution was mixed with the neutralization solution in 3:2 ratio so that the final concentration of collagen was 3 mg/mL. Neutralized collagen was conjugated to 4 or 8 arm PEG Succinimidyl NHS ester 10K (Creative PEGworks; PSB-4413 and PSB-846) via NHS chemistry to react with collagen's primary amines. First, PEG was solubilized in PBS to give a concentration of 100 mg/mL, then 4, 8 and 16 μL of this solution was added to 100 μL of neutralized collagen. Next, the mixed solution of PEG and collagen were put at 37° C. for 30 minutes to form the hydrogels. For non-crosslinked collagen hydrogels, the collagen was neutralized as we mentioned above and incubated for 30 minutes at 37° C. according to the collagen gelation procedure of Thermo Fisher Scientific protocol, which is physically entangled collagen hydrogel commonly used for cell culture.

Mechanical characterization of collagen-PEG hydrogel. The mechanical properties of the collagen hydrogels were evaluated using an ARES-G2 rheometer (TA Instruments, New Castle, DE, USA) at Stanford Soft & Hybrid Materials Facility (SMF, Stanford, CA, USA). For the non-crosslinked collagen hydrogel, neutralized collagen was mounted on the plate and measured. For the collagen-PEG hydrogels 4 or 8 arm PEG NHS solution was added to the neutralized collagen solution. Then the mixed solution was mounted on the plate immediately after mixing with a pipette. To determine gelation time, time sweeps were performed at room temperature for 15 minutes at 1% strain and 1 Hz oscillatory frequency. Then, frequency sweeps from 0.1 to 10 Hz with a fixed 1% strain were performed to determine the completion of gelation. To evaluate how the mechanical properties of the hydrogels could be modulated, collagen-PEG hydrogels were formed at different concentrations 4, 8 and 16% of PEG to collagen. To ensure complete gelation, the resultant solutions were incubated at room temperature for 2 hours, and then frequency sweeps from 0.1 to 10 Hz with a fixed 1% strain were performed.

Optical Property Characterization of collagen-PEG hydrogels. The hydrogels' absorbance from 350 to 800 nm was measured using a SpectraMax M Series Multi-Mode Microplate Reader. The collagen-PEG and non-crosslinked collagen hydrogels were fabricated in a 96 well plate, and the volume was 100 μL. The absorbance was converted to transmittance using the relation $A = 2 - \log 10(\% \, T)$. For each condition, n=3 was used.

Multi-arm collagen-PEG hydrogel degradation. The following methods were consistent for analyzing the degradation of 0.4%, 0.8%, and 1.6% w/v 4 and 8 arm PEG and non-crosslinked collagen hydrogels. Eppendorf tubes were weighed and 200 μL of each hydrogel was fabricated inside of the tubes. Next, 400 μL of 0.1% Collagenase from *Clostridium histolyticum* (Sigma Life Sciences; C0130) in warm supplemented Keratinocyte Serum Free Medium—KSFM (Thermo Fisher Scientific; 17005042) containing Bovine Pituitary Extract (BPE), human recombinant EGF, hydrocortisone 100 ng/mL (Sigma Aldrich; H0008) and insulin 5 μg/mL (Sigma Aldrich; 0516) was added to the tubes containing hydrogel. Untreated hydrogels received 400 μL of warm KSFM with no collagenase. The tubes were placed on a platform rocker, allowing the collagenase to react with the hydrogel. After 1, 2, and 4 hours, the supernatant was removed, leaving the remaining hydrogel behind. The tubes were then flash frozen in liquid nitrogen and lyophilized. After lyophilization, the tubes were weighed and subtracted from the original weight of the empty tube to obtain the weight of the lyophilized hydrogel. For each condition n=3 was used.

Epidermal growth factor release. The collagen-PEG hydrogel including epidermal growth factor (EGF) was fabricated in 48-well plates. The initial volume of solution was 100 μl. After mixing neutralized collagen with 4 or 8 arm PEG-NHS solution in each well, the hydrogel was incubated at 37° C. for 30 minutes. At each well, 500 μl of PBS solution was applied, and the solution was collected and refreshed at each time point. The amount of released EGF was measured by EGF ELISA kit ((30× wash buffer, biotinylated antibody reagent, streptavidin-HRP concentrate, TMB substrate, and stop solution containing 0.16 M sulfuric acid) (Thermo Fisher Scientific, Waltham, MA, USA), and we followed the EGF ELISA kit protocol. Briefly, the collected solutions were added to the capture antibody-coated well plate and incubated at 37° C. for 2 hours. The biotinylated antibody reagent and diluted streptavidin-HRP in PBS were added to the well and incubated for 2 and 1 hour in turn, respectively. After each step, all wells were washed three times using the washing buffer in the kit. For the color development, TMB solution was added and incubated in the dark for 30 min at room temperature, and stop solution was added to stop the reaction without washing. The absorbance of each resultant well was measured at 550 nm using SpectraMax M Series Multi-Mode Microplate Reader (Sunnyvale, CA, USA). For quantification of immobilized EGF, a standard curve of EGF ELISA was obtained following the established protocol of instruction, and the amount of EGF was calculated.

Corneal epithelial cell culture. Immortalized corneal epithelial cells (ICEC) were kindly donated by Djalilian's laboratory from University of Chicago, Illinois. ICEC were culture in supplemented KSFM. After the cells reached 80% confluency, they were passaged. The medium was changed every other day.

Corneal stromal stem cell culture. Corneal stromal stem cells (CSSC) were harvested from human donor corneas provided by Lions Eye Institute. First, the endothelial layer was removed, as well as the central corneal using a trephine (8 mm). The remaining limbal region was dissected into small fragments and placed epithelial side down on 6 well plates. CSSCs were given time to transplant onto a flask bottom over a period of 7 days in Minimum Essential Medium Eagle (Sigma Aldrich; M4526) containing 10% Fetal Bovine Serum (FBS), 1% antibiotic antimycotic solution (Sigma Aldrich; A5955), 1% Non-essential Amino Acid Solution (Sigma Aldrich; M7145) and 1% Glutamax (Thermo scientific; 35050061). After reaching 80% confluence, the CSSC culture was subcultured into colonies and used until passage 4.

Corneal cell biocompatibility, morphology and proliferation on multi-arm collagen-PEG hydrogels. Cornea cell viability was evaluated using Live/Dead assay according to Thermo Fisher Scientific protocol. Briefly, collagen-PEG hydrogels were formed in a 48 well plate as previously mentioned and incubated with supplemented KSFM overnight. Next, $2 \times 10^5$ cells were seeded on the hydrogels for two days. Live/dead solution was added, and the cells were evaluated under inverted microscopic. Cellular morphological behavior of ICEC and CSSC were evaluated by staining the cells with Alexa Fluor™ 488 Phalloidin (Thermo Fisher Scientific; A12379) and Rhodamine Phalloidin (Thermo Fisher Scientific; R415). First, the hydrogels were formed in an 8 well chamber slide and $5 \times 10^4$ cells were seeded on the hydrogel. After 2 days, the cells were fixed with 4% paraformaldehyde (PFA) for 15 minutes, permeabilized and blocked with 0.5% triton-X and 5% goat serum (GS) in PBS for 30 minutes. Then Alexa Fluor™ 488 Phalloidin or Rhodamine Phalloidin were added to the cells in PBS (1:40) for 30 minutes. Next, 4',6-diamidino-2-phenylindole (DAPI) was added in PBS for 5 minutes. The cells were then analyzed using confocal microscopy. Cell proliferation was evaluated using Thiazolyl Blue Tetrazolium Bromide (MTT, Sigma Aldrich; M5655). Briefly, the cells $5 \times 10^4$ were seeded on PEG-collagen hydrogels formed in 96 well plates. After 2 days, the MTT solution was added for 2 hours. The crystals were solubilized using Dimethyl Sulfoxide (DMSO). The absorbance was read at 570 nm. Corneal cells plated on the wells without hydrogels, were considered to have 100% of proliferation.

In vivo Lamellar Keratectomy in Rabbit eyes. Adult New Zealand white rabbits were used to perform a lamellar keratectomy. All anesthesia techniques were performed by the veterinary service center (VSC) at Stanford University.

Prior to surgery, one drop of proparacaine hydrochloride ophthalmic solution was added to the eye receiving treatment. A lamellar keratectomy was performed on the right eye using a 3.5 mm customized vacuum trephine to create a deep circular cut and a spatula was used to remove the stromal layers. Around 5 µL of 4 and 8 arm collagen-PEG hydrogel at 8% v/v PEG-collagen were applied to the keratectomy area and allowed to gel in situ. For 4 arm collagen-PEG hydrogel a n=3 was used while for 8 arm collagen-PEG hydrogel a n=1 was used. A contact lens was applied to keep the hydrogel on the wounded area. A tarsorrhaphy was then performed to prevent agitation by the animal. Ofloxacin ophthalmic solution was applied daily to prevent infection and to retain moisture of the eye. On day 7, the tarsorrhaphy was removed for eye examination: photograph with a Paxos smartphone-based ophthalmic camera adapter. On day 7, the rabbits' eyes were enucleated for imaging.

Immunohistochemistry. The tissues were sectioned, and cross-sections of corneal tissues were fixed with PFA 4%, permeabilized and blocked. Primary antibody ASMA and ZO-1 was incubated in 0.5% triton-x and 5% NGS overnight. Next the secondary antibody anti-mouse Alexa 546 was added. Finally, F-actin and DAPI were added for 30 and 5 minutes respectively. The corneas cross-sections were analyzed under confocal microscopy.

Statistical analysis. All data are expressed as the mean±standard deviation (SD). Each experiment was repeated at least 3 times unless otherwise indicated. Statistical evaluation was performed using a one-way ANOVA. A value of $p < 0.05$ was considered statistically significant. The statistical analysis was performed by using GraphPad Prism 7 statistical software.

Results

Figure 17:
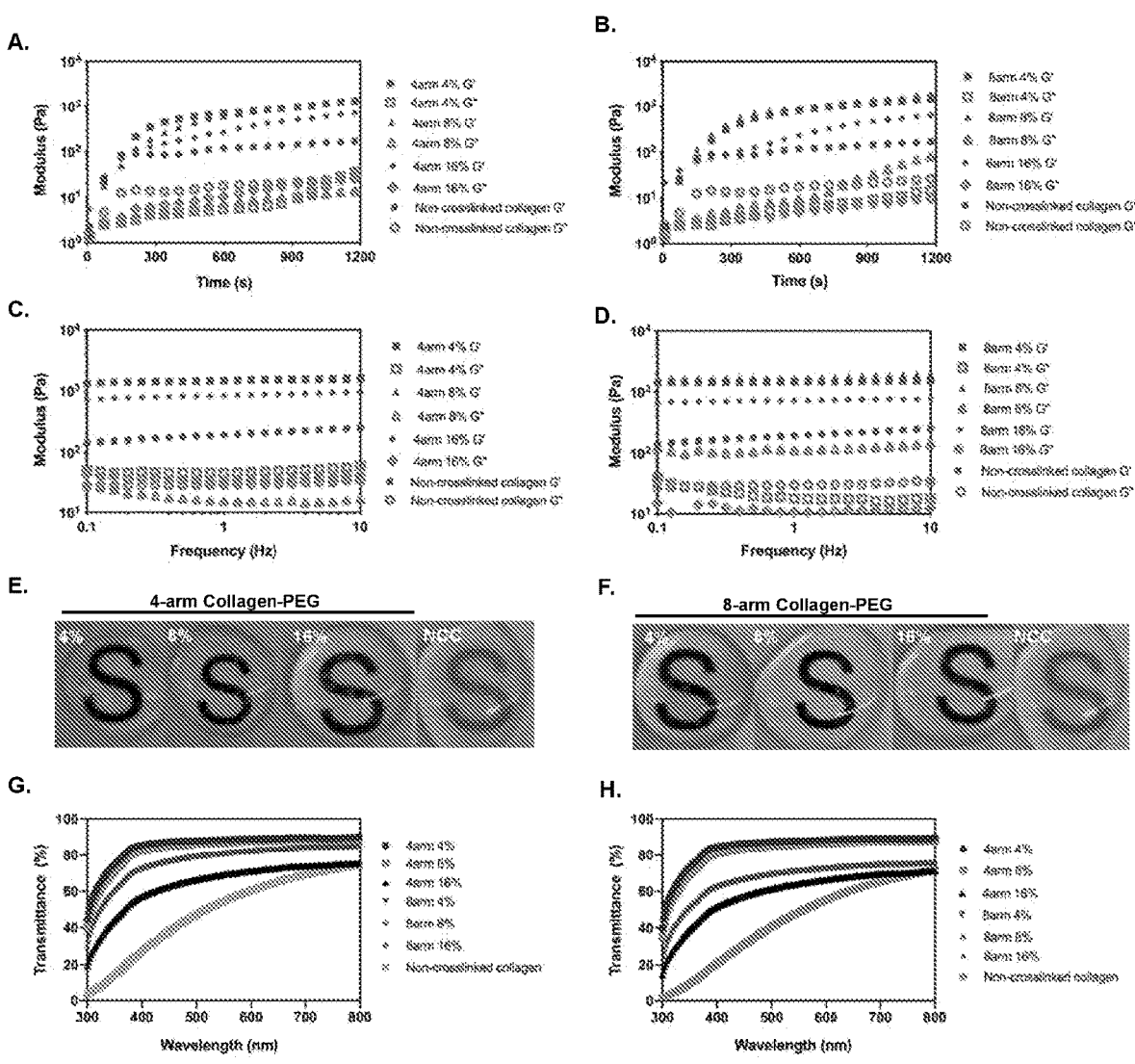
FIG. 17. Physical properties of chemically crosslinked collagen-PEG hydrogels by NHS chemistry and non-crosslinked collagen hydrogels. A) Dynamic moduli of 4-arm collagen-PEG and B) 8-arm PEG-collagen hydrogels using different concentrations of PEG polymer as function of time during gelation. The hydrogels were mounted immediately after mixing. C) Dynamic moduli of 4-arm collagen-PEG and D) 8-arm collagen-PEG hydrogels using different concentrations of PEG polymer as function of frequency. G' and G" represent storage and loss modulus, respectively. E) Photographs of 4 and F) 8-arm collagen-PEG and noncrosslinked collagen hydrogels. G) Transmittance spectra of collagen hydrogels from 350 to 800 nm before swelling and H) after swelling.

Mechanical properties of collagen-PEG hydrogels. Here we applied the NHS ester chemistry to crosslink low concentration of collagen using multi-arm PEG aiming hydrogels with both good adhesion and regeneration properties. The collagen hydrogels were crosslinked with various concentrations (0.4, 0.8 and 1.6% w/v PEG to collagen) of 4-arm and 8-arm PEG-NHS resulting in distinct hydrogels with different mechanical properties depending on the PEG concentration. The mechanical properties of collagen-PEG hydrogels were measured using rheological methods (FIGS. 17A and B). The non-crosslinked collagen hydrogel reached=85 Pa in 300 s and this value increased to =141 Pa until 900 s. For the collagen-PEG hydrogel, the storage modulus was modulated by the crosslink density, but not by the PEG functionality. The storage modulus of 0.4% 4-arm collagen-PEG hydrogel, steadily increased to =1000 Pa through 900 s. The storage modulus of 0.8% 4-arm collagen-PEG hydrogel was similar to 0.4% 4-arm collagen-PEG hydrogel, and for 1.6% 4-arm collagen-PEG hydrogel, the storage modulus remained lower than the other concentration=500 Pa. The storage modulus for the 8-arm collagen-PEG hydrogels were very similar to 4-arm collagen-PEG hydrogels, at the same concentration. To confirm that the gelation was completed, the hydrogels were measured as a function of frequency from 0.1 to 10 Hz (FIGS. 17C and D). The modulus did not vary as a function of the frequency.

The optical properties of the 4 and 8-arm collagen-PEG and non-crosslinked collagen hydrogels were analyzed to determine if the crosslinked hydrogels were suitable for use in the cornea. 4 and 8-arm collagen-PEG hydrogels at 0.4, 0.8 and 1.6% were observed to be relatively transparent while the non-crosslinked collagen hydrogel was relatively opaque (FIGS. 17C and D). To quantify this change in optical transparency, hydrogel transmittance was evaluated at wavelengths between 300 and 800 nm, before and after hydrogel swelling. The transmittance of 4-arm and 8-arm collagen-PEG hydrogels (0.4 and 0.8%) remained constant at =80% in the visible light range. The transmittance of 4-arm collagen-PEG hydrogel at 1.6% increased with wavelength from =30% to 70%, while for the 8-arm collagen-PEG at 1.6% increased from =70% to 80%. The non-crosslinked collagen hydrogel increased from =20% to 80% (FIG. 1D). The transmittance after swelling remained similar as before swelling, however, the 8-arm PEG 16% decreased even more the transparency (FIG. 17E). While for some collagen hydrogels the swelling resulted in increase in transparency, this was not observed for collagen-PEG hydrogels.

Figure 18:
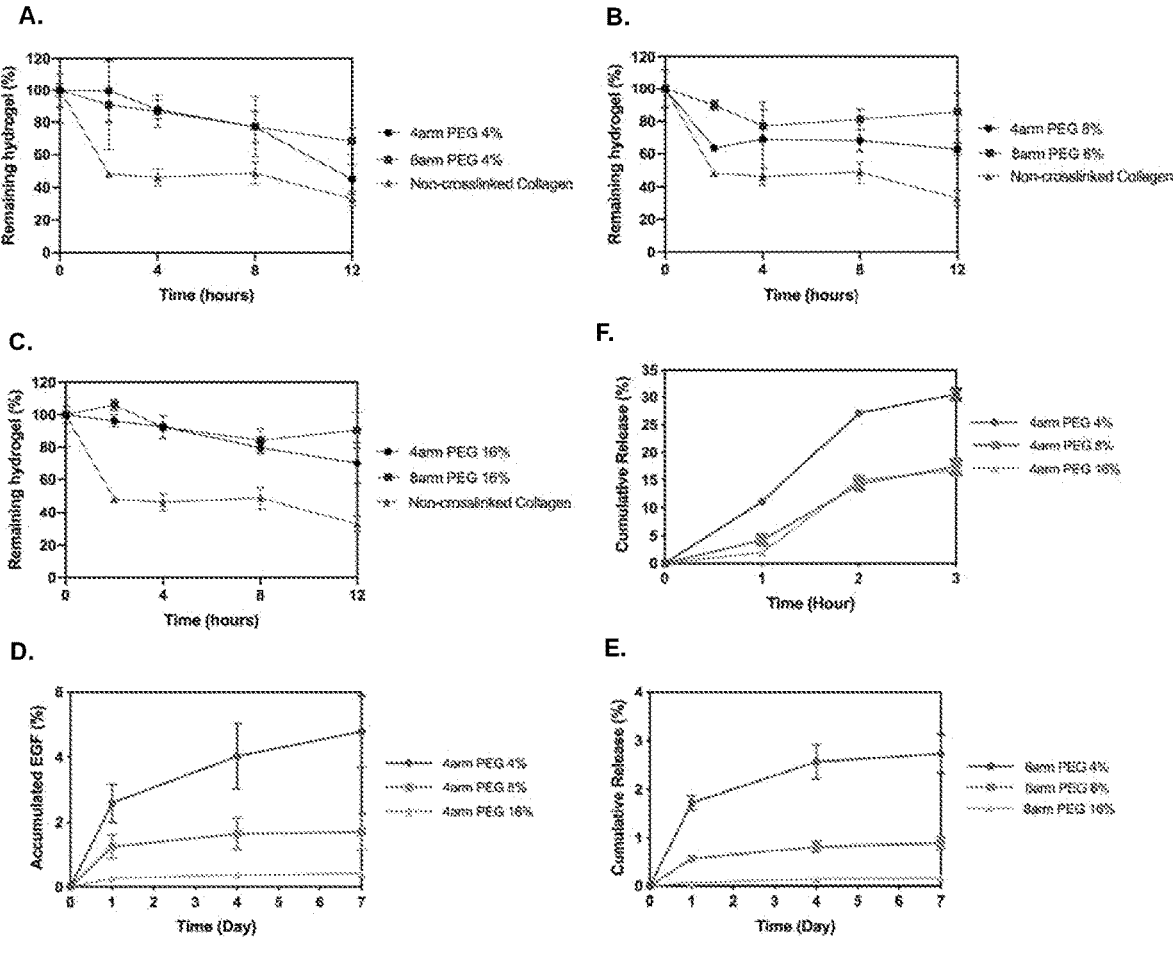
FIG. 18. Degradation of 4 and 8-arm collagen-PEG hydrogels at different concentrations A) 0.4%, B) 0.8% and C) 1.6% was evaluated in the presence of 0.1% of collagenase for 4 hours. EGF release from D) 4-arm PEG and E) 8-arm collagen-PEG hydrogel was evaluated without the addition of collagenase and F) with 0.1% collagenase. For each condition n=3 was used.

Degradability of collagen-PEG hydrogels. Hydrogel degradability is important parameter for corneal repair and regeneration. Ideally, the hydrogel should not degrade too slowly in order to provide for tissue ingrowth. Here, the degradability of collagen-PEG hydrogels was evaluated in the presence of collagenase 0.1% and was monitored as a function of incubation time in PBS at 37° C. (FIG. 18). In the presence of collagenase, non-crosslinked collagen hydrogel degraded about 50% of its initial mass after 2 hours. After 12 hours, about 40% of the hydrogel mass remained. Overall, collagen-PEG hydrogel degradation was dependent on the PEG functionality and concentration. 4-arm collagen-PEG hydrogels were more susceptible to collagenase degradation than 8-arm collagen-PEG hydrogels. After 2 hours in collagenase, the remaining mass for the 0.4% 4-arm PEG and 8-arm collagen-PEG hydrogels was around 100% and after 12 hours the remaining mass was around 50% for 4 arm PEG compared to 80% for 8 arm PEG (FIG. 18A). As expected, less degradation was observed for higher PEG concentrations. After 12 hours the remaining mass for 0.8% 4-arm and 8-arm collagen-PEG hydrogels were 70% and 90%, respectively, and for 1.6% 4-arm and 8-arm collagen-PEG hydrogels were 90% and 100%, respectively (FIGS. 18B and C). The mass of the hydrogels decreased with the time in collagenase.

To evaluate protein release from these hydrogels, EGF was entrapped in the collagen-PEG hydrogels and EGF release was evaluated over one week (without collagenase) and 3 hours (with collagenase). The release of EGF from the hydrogels without collagenase incubation was slow and did not significantly vary with the type and PEG concentration (FIGS. 18D and E). 4-arm collagen-PEG hydrogel at 16% incubated with collagenase released about 35% of EGF in 3 hours, and around 15% of EGF for 0.4 and 0.8% PEG concentration to collagen (FIG. 18F).

Figure 19:
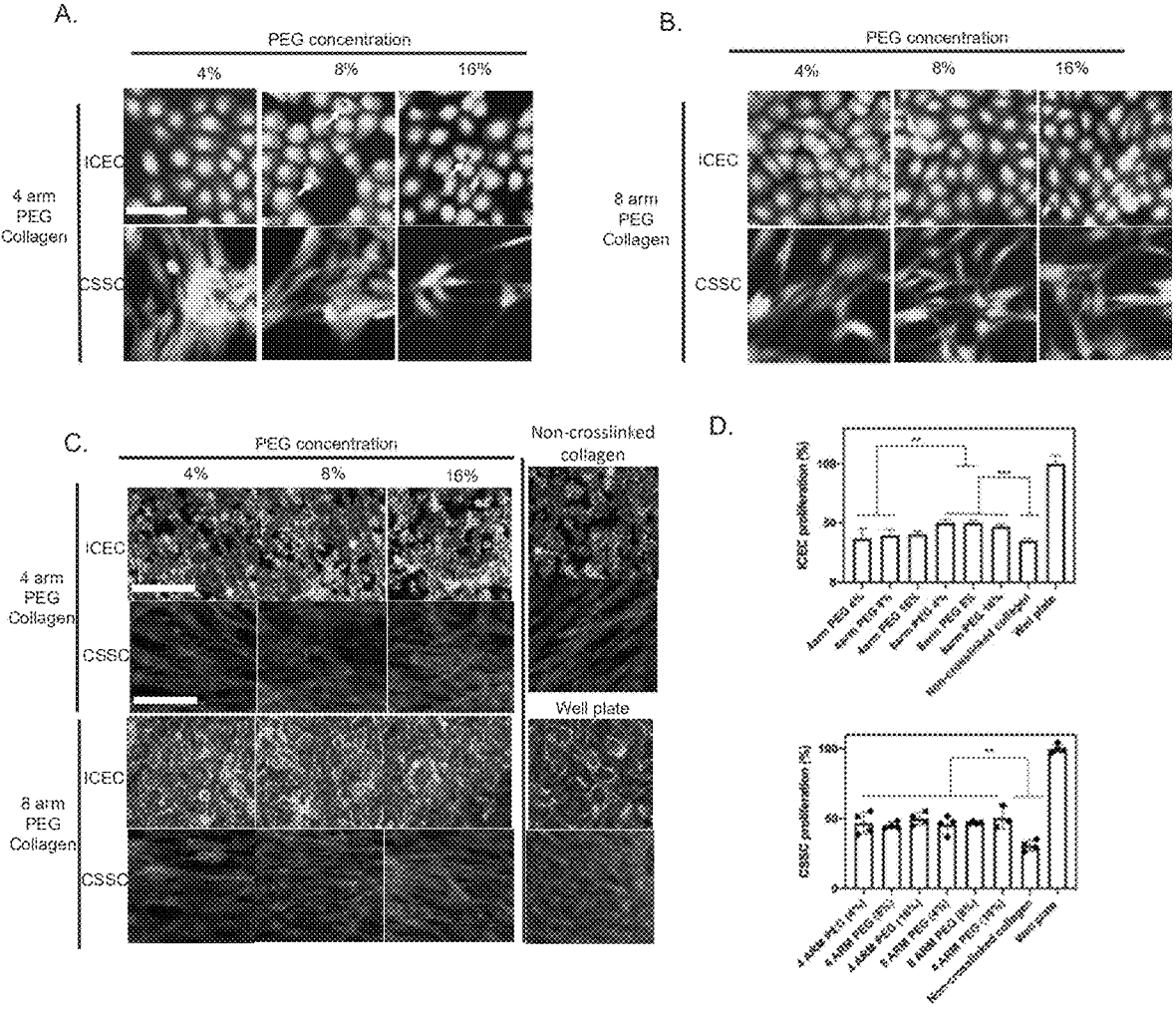
FIG. 19. A) Viability of ICEC and CSSC seeded on 4-arm collagen-PEG and B) 8-arm collagen-PEG hydrogels using different concentrations of PEG polymer after 2 days in culture. Scale bar: 100 µm C) F-actin staining ICEC (green) and CSSC (red) showing cells morphology seeded on 4-arm collagen-PEG and 8-arm collagen-PEG hydrogels using different concentrations of PEG polymer after 2 days in culture. The nucleus (blue) was stained for both cells. Scale bar: 100 µm. D) ICEC and CSSC proliferation on 4-arm collagen-PEG and 8-arm collagen-PEG hydrogels using different concentrations of PEG polymer after 2 days in culture (**p<0.01, n=3).

ICEC growth on collagen-PEG hydrogels. We next evaluated our hydrogels biocompatibility and the ability to provide adhesion and proliferation cues for ICECs. ICECs were seeded on the collagen-PEG hydrogels and incubated for 2 days under optimal conditions. Material biocompatibility was evaluated using Live/Dead assay. 4 arm and 8 arm PEG-collagen hydrogel at varying concentrations, showed low or no cytotoxicity as observed by the green staining (Live cells) and very few dead cells (red staining, arrows) (FIGS. 19A and B). Next, cell morphology was evaluated by staining with F-actin (FIG. 19C). ICEC on non-crosslinked collagen hydrogel was characterized by the presence of lamellipodia and few confluent areas. ICEC behavior did not vary with PEG concentration but was observed to be different with the PEG functionality. ICEC on 4 arm PEG-collagen hydrogels showed concentrated f-actin in the cortical cytoplasm and therefore delimitating cell border. This behavior was also observed for the 8-arm collagen-PEG hydrogels. ICEC on 8-arm collagen-PEG hydrogels formed a tight monolayer similar to what was observed for the well plate. ICEC was not confluent on 4-arm collagen-PEG hydrogels and some round small cells were observed. ICEC proliferation on collagen-PEG hydrogels was evaluated using MTT (FIG. 19C). ICEC grown on the well plate was considered to be 100% proliferated. ICEC seeded on 4-arm collagen-PEG hydrogels at 0.4 and 0.8% showed to proliferate significantly less comparing to the cells seed on 8-arm collagen-PEG for both 0.4 and 0.8% of PEG to collagen. Interestingly, this behavior was not observed for 1.6% w/v of PEG to collagen. Overall, these cells proliferated better on collagen-PEG hydrogels than non-crosslinked collagen hydrogel.

CSSC growth on collagen-PEG hydrogels. CSSC behavior on collagen-PEG hydrogels was also evaluated (FIG. 19A-B). CSSC seeded on collagen-PEG hydrogels, showed stress actin filaments and they were mainly oriented towards the collagen fibers. This behavior was similar for both 4-arm and 8-arm collagen-PEG hydrogel at 0.4, 0.8 and 1.6% w/v PEG to collagen. Comparing to the CSSC seeded on non-crosslinked collagen, the cells seeded on collagen-PEG hydrogel showed to be more confluent. CSSC proliferation on collagen-PEG hydrogels was evaluated using MTT (FIG. 19C). CSSC grown on the well plate was considered to be 100% proliferated. CSSC seeded on collagen-PEG hydrogels proliferated similarly at all concentrations and PEG functionality. CSSC seeded on non-crosslinked collagen hydrogels showed remarkable less proliferation comparing to collagen-PEG hydrogels.

Figure 20:
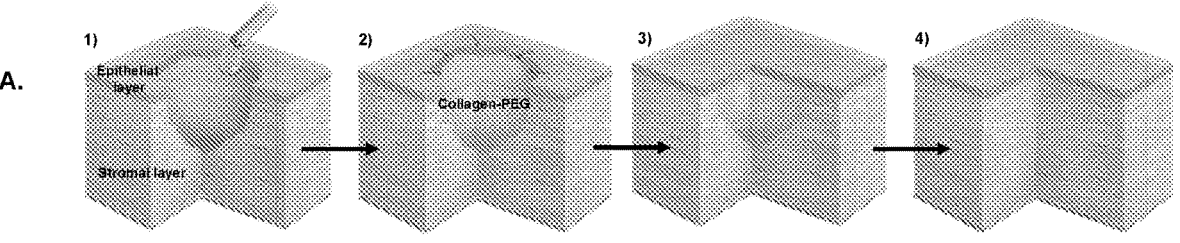
FIG. 20. A) Schematic of lamellar keratectomy and hydrogel treatment as an in situ corneal adhesive for stromal defects. B) Photographic images of rabbit corneas right after lamellar keratectomy showing a rough surface and then a smooth surface followed by the application of the collagen-PEG hydrogels and contact lens. C) 7 days after lamellar keratectomy, collagen-PEG hydrogels in the magenta color below the normal migrated epithelial layer can be observed. For no treatment rabbit, epithelial cells proliferated abnormally, filling the removed stromal layer. ASMA (arrows) was observed for the rabbits that received 4-arm collagen-PEG and saline but not for 8-arm collagen-PEG. Normal epithelial cell phenotype was observed by the presence of ZO-1 in the wing and superficial cells. No ZO-1 expression in the wing cells was observed for the no treated rabbit.
Figure 20:
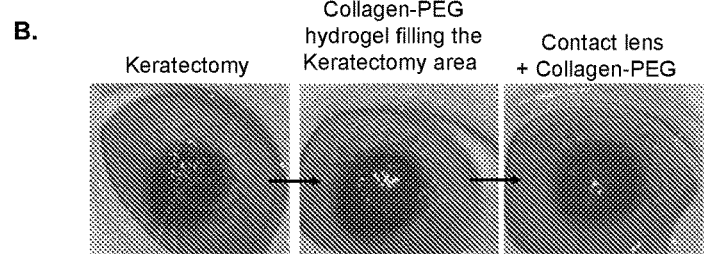
Figure 20:
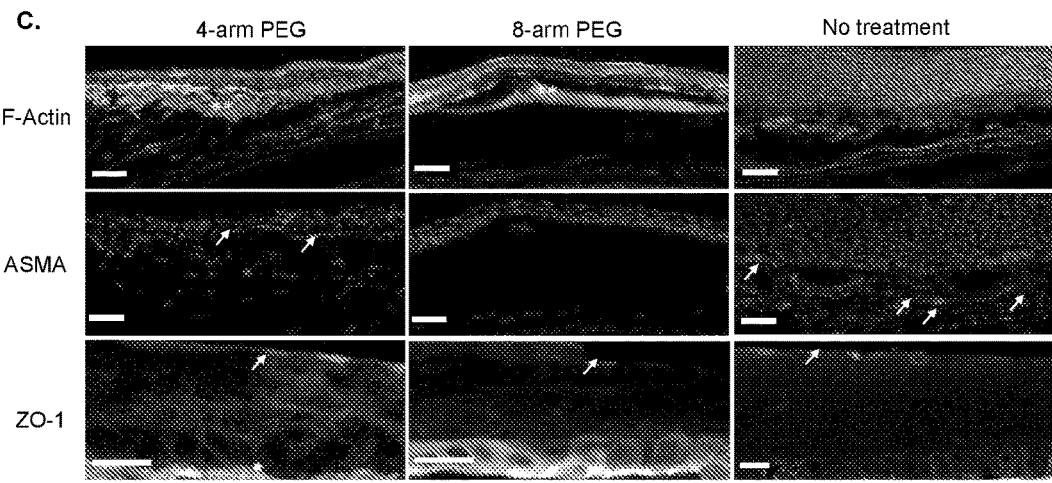

In vivo evaluation of collagen-PEG hydrogels as fillers of corneal defects. Scaffold biointegration to the host tissue is a requirement for proper tissue regeneration. Here we evaluated biointegration by the ability of the hydrogel to adhere to the stromal layer, during the period of seven days, and by cell phenotype. Keratectomy was performed on New Zealand white rabbit's eyes to simulate a stromal defect (FIG. 20A-1). After the keratectomy, the 4 and 8-arm collagen-PEG hydrogels at 0.8% were applied to the defect site (FIG. 20A-2) and then contact lens were placed on the eyes to keep the hydrogel on the cornea. FIG. 20B shows that after the application of the hydrogel the stromal defect becomes smooth comparing to the rough surface right after keratectomy. One week after the keratectomy, the animals were euthanized and the corneas were analyzed for the migration and proliferation of epithelial cells to the hydrogels, presence of ASMA and ZO-1 (FIG. 20C). Collagen-PEG hydrogels were able to support the growth and migration of epithelial cells (FIG. 20A-3) and showed strong adhesion to the remaining stromal tissue after application (FIG. 20C). Several epithelial layers strongly marked by F-actin staining were observed in the no treatment group characterizing an epithelial hyperplasia (FIG. 20C). This was not observed in the groups that received the hydrogels. Myofibroblasts were found to be presented in the treated and control corneas 7 days after the keratectomy. ZO-1 staining was observed for the epithelial superficial layer and wing cells for the treatment groups after keratectomy (FIG. 20C). Control group showed no ZO-1 staining in the wing cells but ZO-1 was present in the superficial cells. Collagen-PEG hydrogels were able to fill the defect area and remained transparent over one week. Epithelial layer was able to cover the hydrogels and stromal layer in growth (FIG. 20A-4) was observed for the 4-arm collagen-PEG but not for the 8-arm collagen-PEG hydrogel. Control group showed epithelial hyperplasia strongly marked by the several layers of epithelial cells. Of note, FIG. 20A1-4 illustrates how various gel formulations in the present invention can be used to fill corneal stromal defects and support surface re-epithelialization and wound closure.

PEG-based ocular adhesives have been approved by the FDA to seal clear corneal incisions commonly used in cataract surgery. In addition to PEG-based materials, currently available corneal adhesives are based on biological fibrin or synthetic cyanoacrylate glues, although both of these are used off-label. The main goal of these treatments is to prevent corneal perforation while promoting re-epithelization. Despite their nontoxicity and low immunogenicity, these material have some limitations regarding its stability and gelation time. Alternative treatments for stromal defects are being explored that improve patient outcomes-since there are no technologies specifically approved for the filling and regeneration of stromal defects. Collagen, hyaluronic acid and gelatin based fillers are being investigated as alternatives to the commercially available treatments to provide a better biointegration with the host tissue. These corneal adhesive must be degradable and support corneal cell migration and proliferation.

Collagen-PEG hydrogels have been previously evaluated for cytocompatibility, and fibroblast proliferation and migration. In situ-forming collagen hydrogels have been cross-linked by strain-promoted azide-alkyne cycloaddition (SPAAC) using bovine collagen type 1 at lower concentration (3 mg/mL). These hydrogels were able to sustain the growth of both human keratinocytes and keratocytes. Here we developed in situ forming collagen hydrogels crosslinked by multi-functional PEG-succinimide that exhibited suitable mechanical and biological properties to fill and repair corneal stromal defects. In our system, bovine collagen type 1 (3 mg/mL) was crosslinked with multi-functional PEG-NHS-SC via primary amine ester reaction. These hydrogels were formed in situ, showed good adhesion, and were transparent and biocompatible. Our results showed that these hydrogels mechanical properties can be tuned by varying PEG concentration, but interestingly not by changing the number of PEG arms. Additionally, the use of concentrations of 0.4%, 0.8% and 1.6% w/v of PEG to collagen resulted in hydrogels that had variable transparency, storage modulus and degradation profile. Higher concentration of PEG negatively impacted collagen-PEG hydrogel properties for corneal regeneration. For instance, the transparency and the storage modulus decreased at 1.6% w/v of PEG to collagen.

Both PEG and collagen have been explored in tissue engineering due to their biocompatibility and ability to be easily modified to create in situ scaffolds with different mechanical properties. These properties are particularly attractive for corneal regeneration applications that require safe and transparent scaffolds. We showed that corneal epithelial and stromal cells were able to proliferate, adhere and had distinct morphology when grown on the collagen-PEG scaffolds. Compared to non-crosslinked collagen hydrogels, ICECs on collagen-PEG hydrogels proliferate better and were able to form a monolayer. CSSC morphology did not vary between the collagen-PEG hydrogels but were able to proliferate more on crosslinked collagen hydrogels than on non-crosslinked collagen. The length of PEG spacer arms but not the storage modulus impacted corneal cell behavior.

The different behaviors observed for corneal cells on crosslinked and non-crosslinked collagen was previously investigated to be related to the alignment of the collagen fibers provided by PEG crosslinking. Here we chose to work with concentrations of 0.8% for the in vivo study due to their superior transparency and mechanical properties compared to 4 and 1.6% PEG to collagen. In vivo experiments showed that our collagen-PEG hydrogels were effective in filling stromal defects and exhibited good adhesion. These hydrogels likely bound to the stromal wound bed due to reactivity of NHS moieties with primary amines in stromal collagen. In addition, collagen-PEG hydrogels promoted normal corneal re-epithelization instead of epithelial hyperplasia which was observed in the no treated group. The degree of epithelial hyperplasia has been correlated with the depth of stromal defects. The presence of collagen-PEG hydrogels provided an artificial stromal matrix on the wound bed that supported epithelial migration and proliferation. These newly formed epithelial layers expressed ZO-1 in the wing cell layer suggesting a normal phenotype.

In normal corneal wound healing, corneal fibroblast infiltration followed by conversion to myofibroblast is observed. In our study, myofibroblastic responses were present in the cornea of animals that received 4 arm collagen-PEG and no treatment, but was not evident in corneas treated with collagen crosslinked with 8-arm PEG linkers. This behavior could be related to the differing enzymatic degradation behaviors related to PEG functionality of collagen-PEG hydrogels observed in vitro. Due to its slower degradability comparing to 4-arm collagen-PEG, the 8-arm collagen-PEG hydrogel may have delayed the infiltration of surrounding stromal cells to the wound area and subsequent fibrous tissue formation. Given that the degradability of the hydrogels could determine stromal ingrowth, the impact of the concentration of collagen-PEG hydrogels on wounds of various sizes and volumes merits further investigation.

Here we showed that collagen hydrogels crosslinked via multifunctional PEG succinimidyl esters can be formed rapidly in situ and used to support epithelial overgrowth and stromal tissue ingrowth when applied to corneal stromal defects. The gels form rapidly under ambient conditions without the need for a chemical or photochemical trigger. The collagen hydrogels crosslinked by 4-arm PEG could be detected in the cornea for 7 days and allowed stromal ingrowth. The collagen hydrogel crosslinked by 8-arm PEG exhibited slower in vivo degradation, and stromal ingrowth was delayed. However, for both types of hydrogels, the epithelial layer migrated over the hydrogel and formed a multilayer. In vitro studies showed that the hydrogels were cytocompatible and morphological and proliferation of corneal cells were superior to that seen on non-crosslinked collagen hydrogels. The hydrogels' physical properties could be modulated by changing the PEG concentration. These collagen-PEG hydrogels represent a promising alternative to cyanoacrylate glue as an in situ stabilizer of corneal defects given their transparency and ability to support surface epithelialization. Future studies evaluating this hydrogel system's capacity to support epithelial overgrowth and stromal biointegration over longer periods are merited.

REFERENCES

1. Channa, R.; Zafar, S. N.; Canner, J. K.; Haring, R. S.; Schneider, E. B.; Friedman, D. S., Epidemiology of Eye-Related Emergency Department Visits. *JAMA Ophthalmology* 2016, 134 (3), 312-319.
2. Lagali, N., Corneal Stromal Regeneration: Current Status and Future Therapeutic Potential. *Current Eye Research* 2019, 1-13.
3. Samarawickrama, C.; Samanta, A.; Liszka, A.; Fagerholm, P.; Buznyk, O.; Griffith, M.; Allan, B., Collagen- Based Fillers as Alternatives to Cyanoacrylate Glue for the Sealing of Large Corneal Perforations. *Cornea* 2018, 37 (5), 609-616.

4. Trujillo-de Santiago, G.; Sharifi, R.; Yue, K.; Sani, E. S.; Kashaf, S. S.; Alvarez, M. M.; Leijten, J.; Khademhosseini, A.; Dana, R.; Annabi, N., Ocular adhesives: Design, chemistry, crosslinking mechanisms, and applications. *Biomaterials* 2019, 197, 345-367.

5. Gain, P.; Jullienne, R.; He, Z.; Aldossary, M.; Acquart, S.; Cognasse, F.; Thuret, G., Global Survey of Corneal Transplantation and Eye Banking. *JAMA Ophthalmology* 2016, 134 (2), 167-173.

6. Koivusalo, L.; Kauppila, M.; Samanta, S.; Parihar, V. S.; Ilmarinen, T.; Miettinen, S.; Oommen, O. P.; Skottman, H., Tissue adhesive hyaluronic acid hydrogels for sutureless stem cell delivery and regeneration of corneal epithelium and stroma. *Biomaterials* 2019, 225, 119516.

7. Palchesko, R. N.; Carrasquilla, S. D.; Feinberg, A. W., Natural Biomaterials for Corneal Tissue Engineering, Repair, and Regeneration. *Advanced Healthcare Materials* 2018, 7 (16), 1701434.

8. Assmann, A.; Vegh, A.; Ghasemi-Rad, M.; Bagherifard, S.; Cheng, G.; Sani, E. S.; Ruiz-Esparza, G. U.; Noshadi, I.; Lassaletta, A. D.; Gangadharan, S.; Tamayol, A.; Khademhosseini, A.; Annabi, N., A highly adhesive and naturally derived sealant. *Biomaterials* 2017, 140, 115-127.

9. Yue, B., Biology of the extracellular matrix: an overview. *J Glaucoma* 2014, 23 (8 Suppl 1), S20-S23.

10. Kong, B.; Sun, W.; Chen, G.; Tang, S.; Li, M.; Shao, Z.; Mi, S., Tissue-engineered cornea constructed with compressed collagen and laser-perforated electrospun mat. *Scientific Reports* 2017, 7(1), 970.

11. Latifi, N.; Asgari, M.; Vali, H.; Mongeau, L., A tissue-mimetic nano-fibrillar hybrid injectable hydrogel for potential soft tissue engineering applications. *Scientific Reports* 2018, 8 (1), 1047.

12. Lee, H. J.; Fernandes-Cunha, G. M.; Na, K.-S.; Hull, S. M.; Myung, D., Bio-Orthogonally Crosslinked, In Situ Forming Corneal Stromal Tissue Substitute. *Advanced Healthcare Materials* 2018, 7 (19), 1800560.

13. Sargeant, T. D.; Desai, A. P.; Banerjee, S.; Agawu, A.; Stopek, J. B., An in situ forming collagen-PEG hydrogel for tissue regeneration. *Acta Biomaterialia* 2012, 8 (1), 124-132.

14. Nallasamy, N.; Grove, K. E.; Legault, G. L.; Daluvoy, M. B.; Kim, T., Hydrogel ocular sealant for clear corneal incisions in cataract surgery. *Journal of Cataract & Refractive Surgery* 2017, 43 (8), 1010-1014.

15. Masket, S.; Hovanesian, J. A.; Levenson, J.; Tyson, F.; Flynn, W.; Endl, M.; Majmudar, P. A.; Modi, S.; Chu, R.; Raizman, M. B.; Lane, S. S.; Kim, T., Hydrogel sealant versus sutures to prevent fluid egress after cataract surgery. *Journal of Cataract & Refractive Surgery* 2014, 40 (12), 2057-2066.

16. Yin, J.; Singh, R. B.; Al Karmi, R.; Yung, A.; Yu, M.; Dana, R., Outcomes of Cyanoacrylate Tissue Adhesive Application in Corneal Thinning and Perforation. *Cornea* 2019, 38 (6), 668-673.

17. Shirzaei Sani, E.; Kheirkhah, A.; Rana, D.; Sun, Z.; Foulsham, W.; Sheikhi, A.; Khademhosseini, A.; Dana, R.; Annabi, N., Sutureless repair of corneal injuries using naturally derived bioadhesive hydrogels. *Sci Adv* 2019, 5 (3), eaav1281-eaav1281.

18. Rafat, M.; Li, F.; Fagerholm, P.; Lagali, N. S.; Watsky, M. A.; Munger, R.; Matsuura, T.; Griffith, M., PEG-stabilized carbodiimide crosslinked collagen-chitosan hydrogels for corneal tissue engineering. *Biomaterials* 2008, 29 (29), 3960-3972.

19. Garagorri, N.; Fermanian, S.; Thibault, R.; Ambrose, W. M.; Schein, 0. D.; Chakravarti, S.; Elisseeff, J., Keratocyte behavior in three-dimensional photopolymerizable poly (ethylene glycol) hydrogels. *Acta biomaterialia* 2008, 4 (5), 1139-1147.

20. Lin, S.; Gu, L., Influence of Crosslink Density and Stiffness on Mechanical Properties of Type I Collagen Gel. *Materials (Basel)* 2015, 8 (2), 551-560.

21. Eagle, R. C., Jr.; Dillon, E. C.; Laibson, P. R., Compensatory epithelial hyperplasia in human corneal disease. *Trans Am Ophthalmol Soc* 1992, 90, 265-276.

22. Suzuki, K.; Tanaka, T.; Enoki, M.; Nishida, T., Coordinated Reassembly of the Basement Membrane and Junctional Proteins during Corneal Epithelial Wound Healing. *Investigative Ophthalmology & Visual Science* 2000, 41 (9), 2495-2500.

23. Wilson, S. E., Corneal myofibroblast biology and pathobiology: generation, persistence, and transparency. *Exp Eye Res* 2012, 99 (1), 78-88.

Example 4

PEG Peptide Gels

Materials. 4-arm poly(ethylene glycol)-succinimidyl carboxyl methyl ester (4-arm PEG-SCM), KKKRGDKKK peptide, KKKRGD peptide, KKK peptide, 1× phosphate-buffered saline (PBS), 1 M sodium hydroxide (NaOH), double distilled water (dd-H$_2$O).

Methods. For the following RGD gel fabrication methods, the RGD neutralization solution was made by mixing 1N NaOH, dd-water, 10×PBS, and 1×PBS at a volume ratio of 15:285:100:1600.

RGD 1 is made with a 7 to 1 ratio of 4-arm PEG-SCM to the KKKRGDKKK peptide. To make the RGD 1 gel, quickly mix 5 mg of 4-arm PEG-SCM, 37.5 µl 1×PBS and 12.5 µl of 16 mg/ml KKKRGDKKK in the order it is written. Briefly sonicate the peptide mixture until it is homogenous. Transfer the entirety of the peptide mixture onto the desired surface where the gel is to be formed. Add 50 µl of the RGD neutralization solution to the peptide mixture and quickly mix to form the gel. The gel will form within seconds of adding the RGD neutralization solution.

RGD 2 is made with a 21 to 4 ratio of 4-arm PEG-SCM to the KKKRGDKKK peptide. To make the RGD 2 gel, quickly mix 5 mg of 4-arm PEG-SCM, 8.33 µl of 32 mg/ml KKKRGDKKK, and 41.67 µl 1×PBS in the order it is written. Briefly sonicate the peptide mixture until it is homogenous. Transfer the entirety of the peptide mixture onto the desired surface where the gel is to be formed. Add 50 µl of the RGD neutralization solution to the peptide mixture and quickly mix to form the gel.

RGD 3 is made with a 7 to 1 ratio of 4-arm PEG-SCM to the KKKRGD peptide. To make the RGD 3 gel, quickly mix 5 mg of 4-arm PEG-SCM, 7.15 µl of 18.24 mg/ml KKKRGD, and 42.85 µl 1×PBS in the order it is written. Briefly sonicate the peptide mixture until it is homogenous. Transfer the entirety of the peptide mixture onto the desired surface where the gel is to be formed. Add 50 µl of the RGD neutralization solution to the peptide mixture and quickly mix to form the gel.

The trilysine (KKK sequence) gel is made with a 7 to 1 ratio of 4-arm PEG-SCM to the KKK peptide. To make the trilysine gel, quickly mix 5 mg of 4-arm PEG-SCM, 12.5 µl dd-water, and 12.5 µl 5.76 mg/mL KKK/dd-water in the order it is written. Briefly sonicate the peptide mixture until it is homogenous. Transfer the entirety of the peptide mixture onto the desired surface where the gel is to be formed. Add 75 μl of the RGD neutralization solution to the peptide mixture and quickly mix to form the gel.

Figure 21:
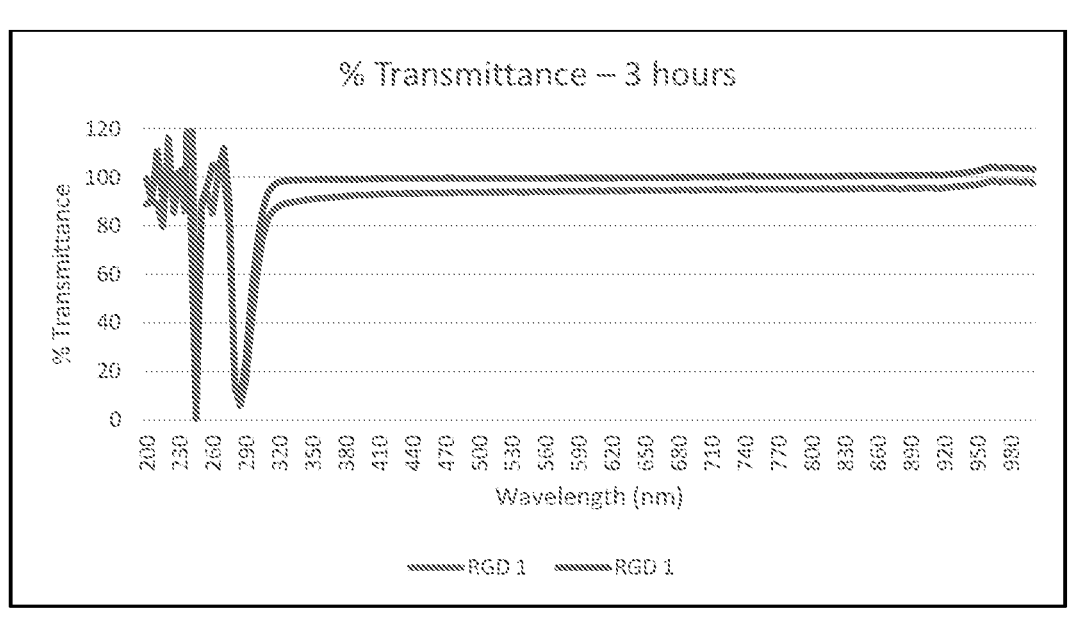
FIG. 21. Transparency of RGD gels.
Figure 23:
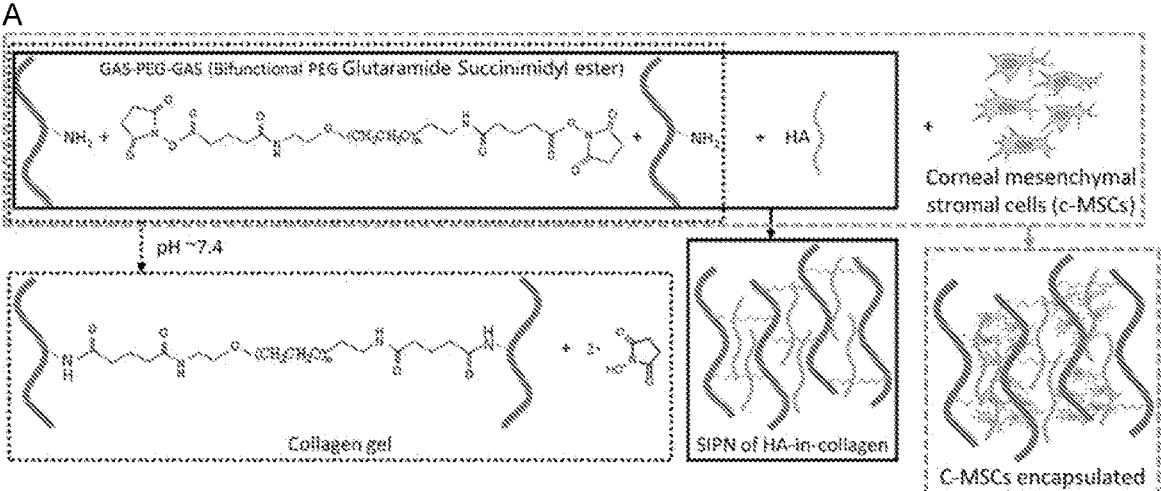
FIGS. 23A-E. Synthesis, cell encapsulation, and characterizations of exemplary semi-IPNs. (A) Scheme of the synthesis of hyaluronic acid (HA) in collagen gel crosslinked with a bifunctional succinimidyl ester crosslinker (GAS-PEG-GAS) and the process for cell encapsulation. (B)
Figure 23:
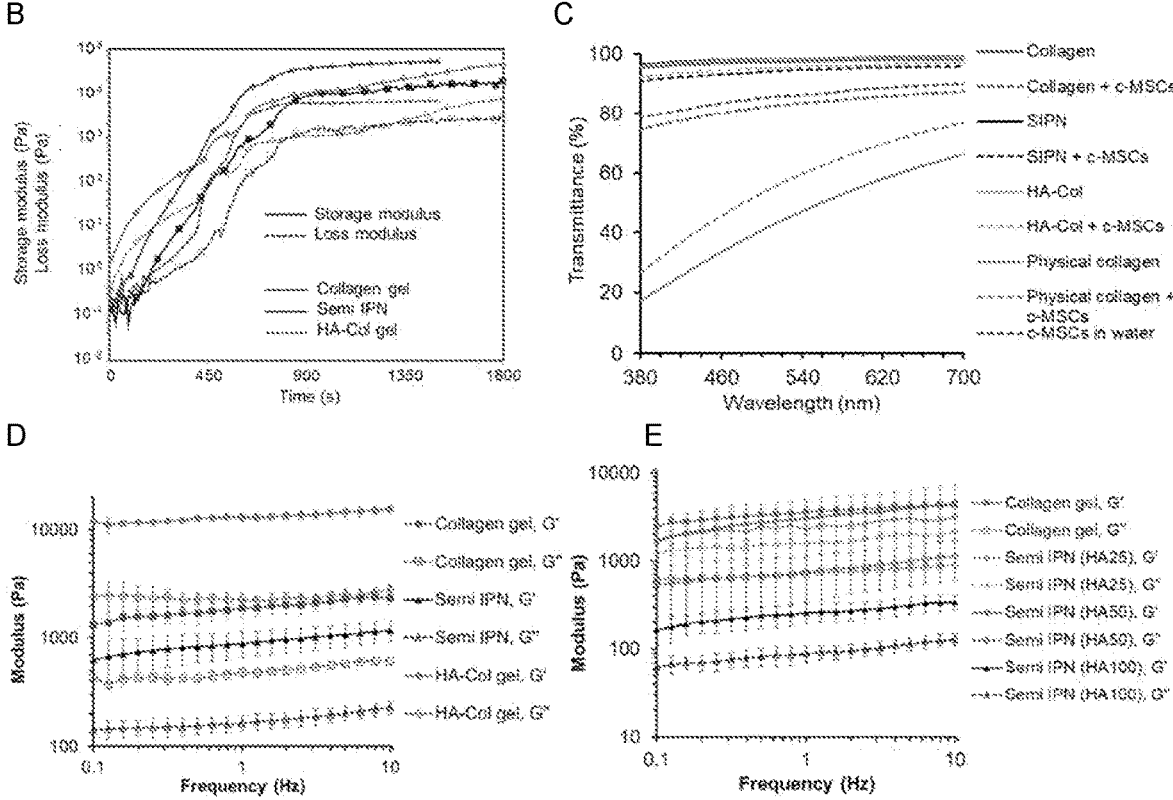

The RGD sequence in the peptides can be replaced with YIGSR, which is also a cell-adhesive peptide sequence, other cell-adhesive peptide sequences, or various combinations of cell-adhesive sequences, including repeated RGD and/or YIGSR sequences, or ones where they are combined in various ways (e.g. RGD-YIGSR-RGD-YIGSR or other combinations). The lysine-containing sequence can be longer or shorter than three peptides, and and go on the ends or in the middle of cell-adhesive sequences. For instance, KKK-RGD, or KKK-RGD-KKK or RGD-KKK, with longer or shorter repeats of the lysine residue. Other amino acids may be substituted into the sequence conferring various other properties. At a minimum it would have the cell-adhesive sequence (e.g. RGD and/or YIGSR) and at least 2 lysines (KK), but in a preferred embodiment have three lysines (trilysine), or in other embodiments, more lysines and/or more cell-adhesive sequences. ve sequences.
Results The RGD-PEG formulations formed gels rapidly upon mixing, and were highly transparent. For example, the transmittance of RGD 1 was over 95% in the visible spectral when the gel thickness was 3.3 mm. All RGD gels were adhesive. (FIG. 21).

Figure 22:
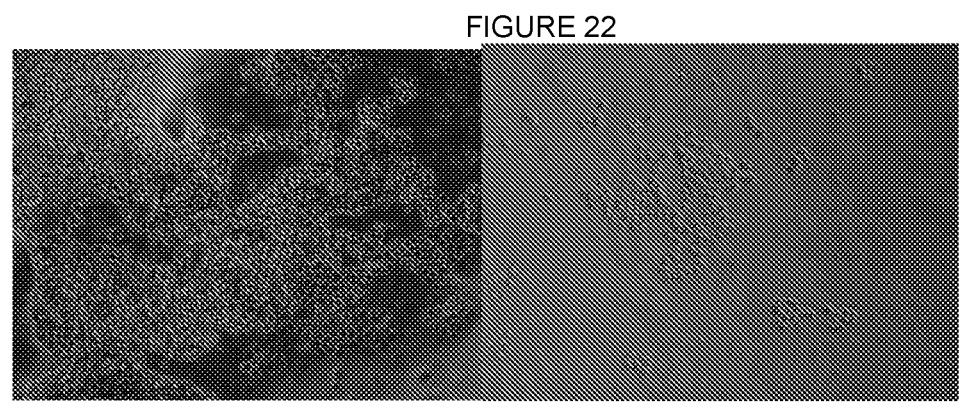

Shown in FIG. 22, The cell studies showed how compositions affect the cell adhesion and growth on top of RGD gels. The trilysine gel, without an RGD sequence in it, had a much lower cell adhesion than gel 1-3. Dangling RGD in gel 3 showed a weaker cell adhesion than gel 1 & 2. There was no obvious difference in cell adhesion between RGD gels 1&2. Live/dead assay showed excellent cell compatibility of all gels. The RGD gel can be applied on corneal in situ or ex situ. Gels applied to ex vivo corneal tissue showed a good retention on corneal defects even rinsed with a great amount of water.

Example 5

Figure 26:
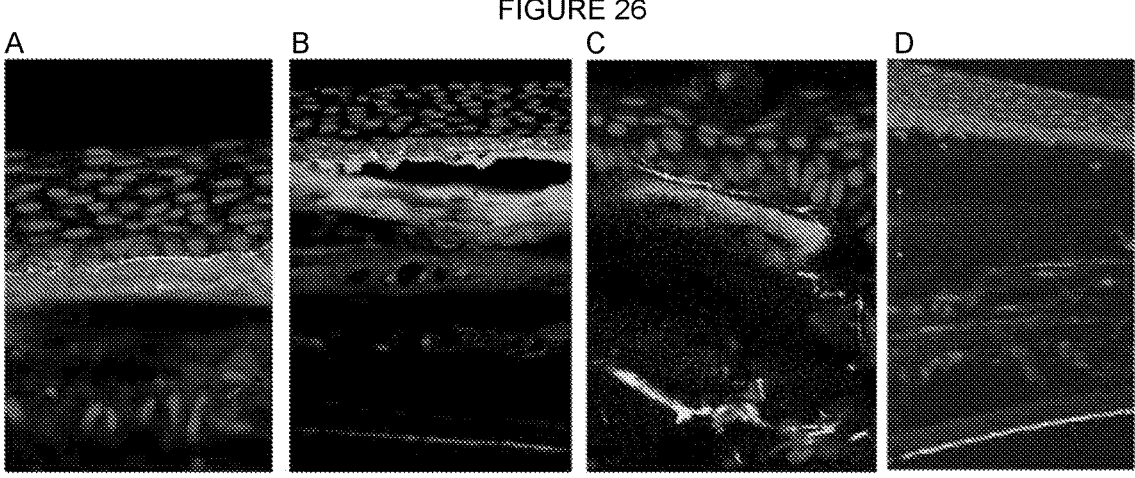

Shown in FIG. 26, deposition of basement membrane proteins collagen IV and laminin was observed at the interface between the cells and the gel (FIGS. 26*a-b*), and corneal nerves were present in the vicinity of the gel (FIG. 26*c*). The corneal endothelium also appeared healthy and intact after treatment (FIG. 26*d*). Thus, the Col-HA gel formed by SPAAC crosslinking chemistry facilitates rapid and functional, multi-layered epithelialization with basement membrane deposition, evidence of corneal nerve regeneration, and intact endothelium.

Figure 27:
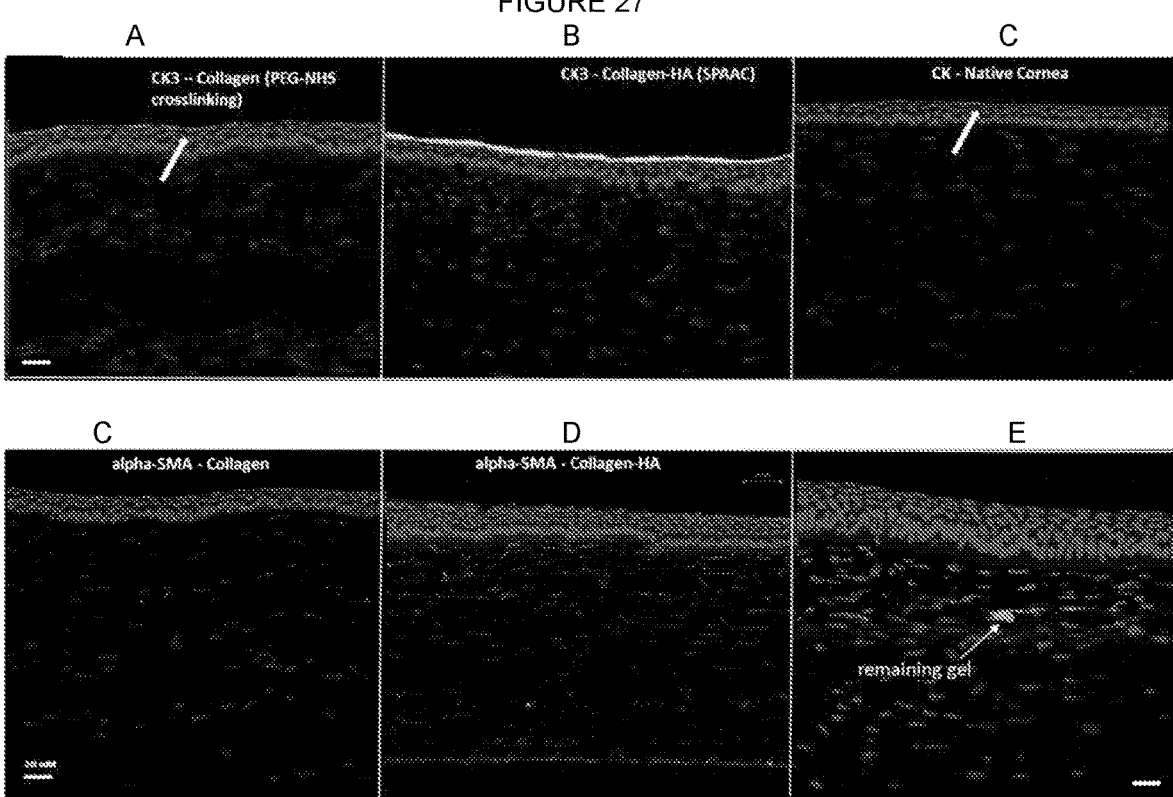
Figure 28:
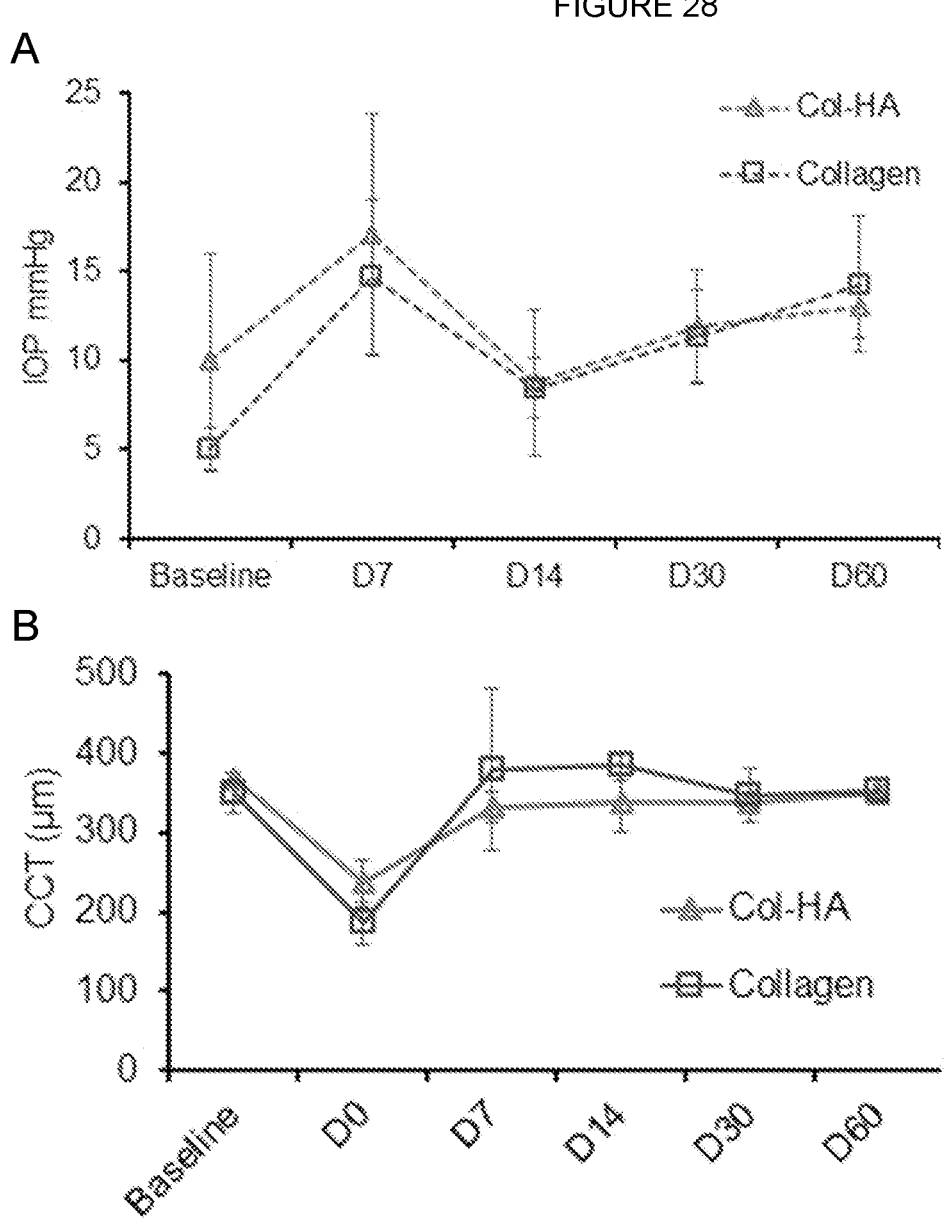
Figures 29, 30:
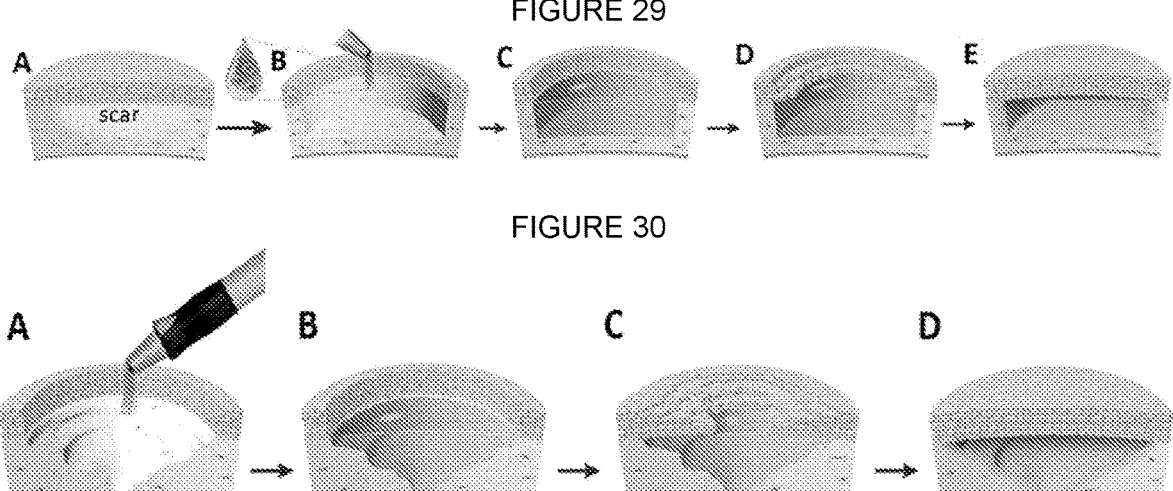
Figure 31:
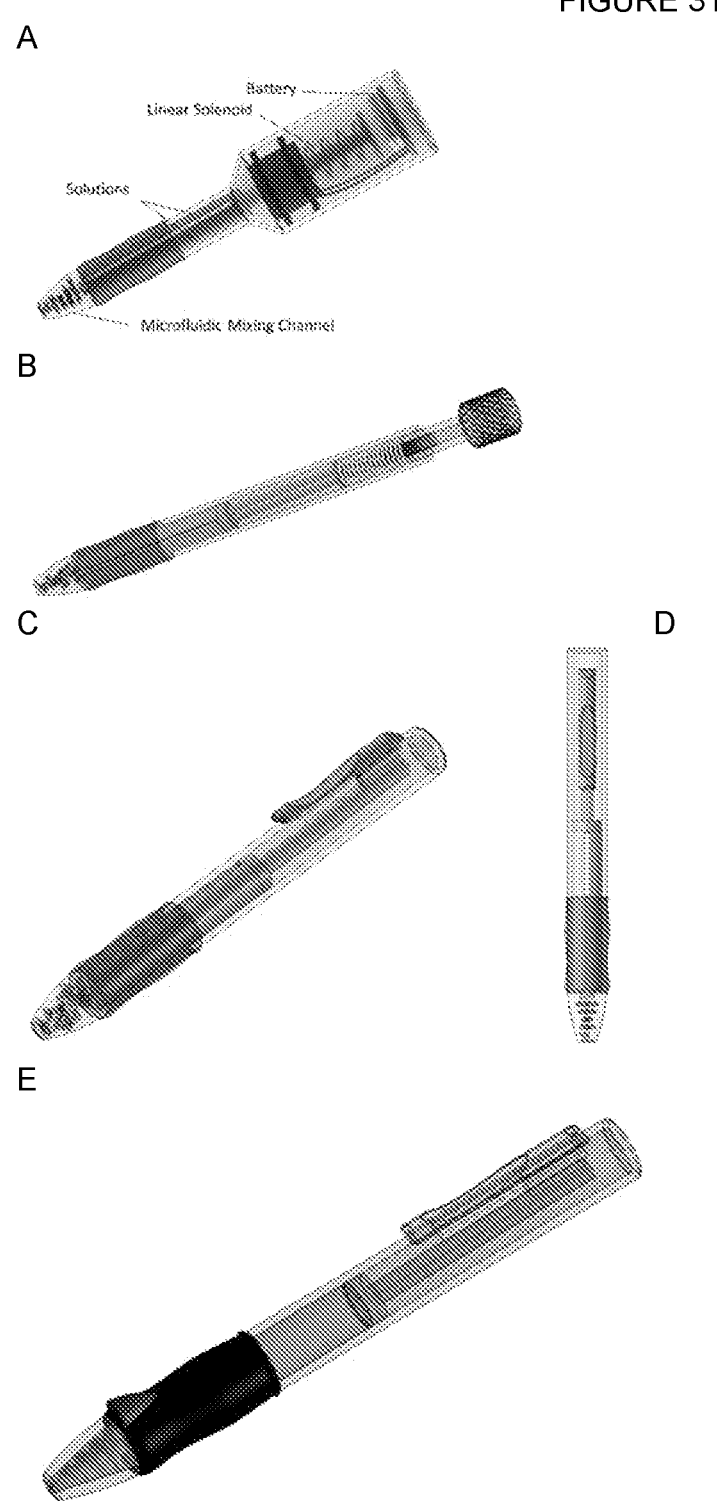

Non-photochemically crosslinked collagen and Col-HA gels perform well in vivo at 2 months. Rabbit corneas treated with collagen gels crosslinked via succinimide chemistry and Col-HA gels crosslinked via SPAAC after keratectomy were examined after 2 months (FIG. 27). Both the Collagen (FIG. 27*a*) and Col-HA gels (FIG. 27*b*) stained positively for CK3 similar to that of the untreated cornea (FIG. 27*c*). Meanwhile, both collagen and Col-HA gels also showed minimal staining for alpha-SMA (FIGS. 27*d-e*). The gels, which were labeled with AlexaFluor-647, could be tracked as well; none of the Col-HA gels (not shown) and only a small amount of the collagen-only gels remained (FIG. 27*f*). Corneal nerves were visible in the area of the gel (FIG. 27*a*). Intraocular pressure (IOP) and pachymetry measurements of the treated corneas out to 2 months is shown in FIGS. 27*b-c*.

Corneas treated with both types of gels maintained, on average, normal IOP and returned to and remained at normal thickness over the two month time interval.

For embodiments where two conjugated macromolecules are reacted via SPAAC, one conjugate can be held in one chamber and a second conjugate can be held in another chamber, where the contents of the two chambers are admixed at a microfluidic mixing channel at the tip of a handheld dispenser. The two conjugates begin reacting upon mixing and are dispensed at the distal end of the microfluidic mixing channel. The dispenser is designed to dispense a microliter-scale volume of the mixture to the site of interest, e.g. a corneal wound or a skin wound. In most embodiments, the range of volumes dispensed at a corneal wound is between about 1 microliter and 50 microliters depending on the size of the wound being filled. In some embodiments, the dispenser is electrically driven, e.g. by a solenoid or a step motor. In other embodiments, it is driven by combination of a spring and mechanical means. In still other embodiments, it is purely mechanical e.g. by pushing or sliding of an element that moves a piston in the axial direction. In some embodiments, both chambers are solutions of conjugated polymers or biopolymers. In other embodiments, the polymer backbones of the two solutions are different, e.g. one contains conjugated collagen and the other contains conjugated PEG, or one contains conjugated collagen and the other contains conjugated hyaluronic acid (HA). In other embodiments, one of the two solutions contains cells (e.g. corneal stromal stem cells). In some embodiments, both solutions contains cells. In still other embodiments, there is a single chamber that contains a solution of a polymer or biopolymer that flows into a mixing tip that contains a polymer in the solid state (e.g. packed powder or pellet), where flow of the first solution across the solid state polymer leads to dissolution of that polymer into the aqueous phase of the first solution, leading to reaction between the first polymer and second polymer. For instance, the first polymer solution can be collagen, while the second polymer in the solid state can be a multi-functional PEG-NHS crosslinker. When the two mix, a polymer gel network is formed rapidly as it is dispensed from the tip. In some embodiments, the mixing tip contains a microfluidic channel with a serpentine, zig zag, or other pattern that enables mixing and reaction between two or more solutions. In other embodiments, the mixing tip is a spiral or screw-like in configuration. In other embodiments, a polymer is positioned in the solid state (e.g. as a packed powder or pellet) somewhere along the path within a mixing tip.

TEXT FOR FIG. 32: Bio-orthogonally crosslinked, in situ-forming collagen gels with encapsulated stromal cells promote rapid corneal epithelial wound healing in vivo. Using an established ex vivo rabbit organ culture model, we previously demonstrated that SPAAC-crosslinked collagen hydrogels were able to support the growth of a multi-layered epithelium (which is observed in normal corneas) when used to fill a deep corneal defect and showed that it supported multi-layered epithelialization. We have validated this result through in vivo studies as well, delivering c-MSCs within SPAAC-crosslinked collagen gels to wounded rabbit corneas. Briefly, a deep anterior lamellar keratectomy was performed on rabbit eyes and the wound area was treated with c-MSC-laden SPAAC-crosslinked collagen gels and compared to untreated controls. The epithelial defect (FIG. 32A) was filled with SPAAC-crosslinked collagen gels containing c-MSCs and covered with a bandage contact lens and a partial tarsorraphy. After one week, the corneas were found to be not only clear (FIG. 32B) but also without fluorescein staining (FIG. 32C). An OCT image of the in situ-formed gel with encapsulated c-MSCs (speckles) within the keratectomy wound is shown in FIG. 32D. Immunohistochemical analysis of the excised corneal tissue on day 7 showed that the c-MSC-laden in situ forming matrix procedure facilitated migration of epithelial cells across the entire gel and supported the growth of a multilayered epithelium with CK3-positive, stratified morphology (FIG. 32E). These results indicate that SPAAC-crosslinked collagen gels with encapsulated c-MSCs remain transparent over one week and promote rapid, multi-layered corneal epithelial wound healing in vivo.

The sealing capacity of collagen-PEG hydrogels crosslinked with 8-arm PEG-NHS, physically crosslinked collagen, and the commercially available sealant (ReSure, Ocular Therapeutix) was determined using a burst pressure test, as described elsewhere with modifications. After creating a corneal perforation with a 19 gauge needle (outer diameter 1.067 mm), the hydrogels and Resure were applied to the perforation site (FIGS. 33A, B and C). The pressure inside the eye was gradually increased by injecting saline into the anterior chamber at a constant rate using a syringe pump. The burst pressure for ReSure, a commercially available ocular sealant, was found to be around 28 kPa (~210 mm Hg) and for physically crosslinked collagen, approximately 4 kPa (~30 mm Hg), while the average burst pressure for collagen-PEG was 41 kPa (307 mm Hg). This was significantly higher than that of the physically crosslinked collagen hydrogel (p=0.0009). The burst pressure of the collagen-PEG was also higher than that of the ReSure sealant, but this difference was not statistically significant for the number of samples tested (n=3). These results (FIG. 33D) suggest that collagen-PEG gels crosslinked by 8-arm PEG-NHS—which support epithelialization in vivo—can also strongly adhere to the cornea and seal corneal wounds much in the way that commercially available sealants can.

What is claimed is:

1. A composition for use as an in-situ-forming hydrogel in treating or reconstructing a surgically incised or wounded area in a mammalian subject in need thereof, comprising an interpenetrating polymer network (IPN) or semi-IPN of independently associated, wherein the hydrogel is an IPN comprising a first polymer that is functionalized with first reactive groups, and a second polymer that is functionalized with second reactive groups, wherein each of the polymer components is cross-linked with a different modality so that independent networks are formed; wherein upon mixing of the first and second polymers the first polymer and the second polymer form an interpenetrating polymer network on the wounded area in situ without the need for an external energy source.

2. The composition of claim 1 wherein the first polymer is collagen.

3. The composition of claim 1, wherein the second polymer is hyaluronic acid.

4. The composition of claim 1, wherein the first or the second reactive groups are moieties that result in a SPAAC click reaction.

5. The composition of claim 1, wherein the second reactive groups are moieties that result in a thiol-ene click reaction.

6. The composition of claim 1, wherein the first or the second reactive groups are moieties that result in N-hydroxysuccinimide-based crosslinking.

7. The composition according to claim 1, wherein the hydrogel is applied to a corneal defect in a flowable liquid state and allowed to form a smooth contour on its surface as it gels.

8. The composition of claim 7, furthermore comprising cells encapsulated within said formed gel to promote the treating or reconstructing of the wounded corneal area.

9. The composition of claim 1, wherein the IPN or semi-IPN is simultaneously formed.

10. The composition of claim 1, wherein the IPN or semi-IPN is sequentially formed.

11. A method of treating or reconstructing a surgically incised or wounded corneal area in a mammalian subject in need thereof, comprising administering the composition of claim 1.

12. A composition for use as an in-situ-forming hydrogel in treating or reconstructing a surgically incised or wounded area in a mammalian subject in need thereof, comprising an interpenetrating polymer network (IPN) or semi-IPN of independently associated, wherein the hydrogel is a semi IPN comprising a first polymer that is functionalized with first reactive groups, and a second polymer that is not chemically cross-linked; wherein upon mixing of the first and second polymers the first polymer and the second polymer form an interpenetrating polymer network on the wounded area in situ without the need for an external energy source.

13. A composition for use as an in-situ-forming hydrogel in treating or reconstructing a surgically incised or wounded area in a mammalian subject in need thereof, comprised of a network of polymer crosslinked with multi-arm PEG;

comprising: a peptide sequence comprising primary amine groups, and a multi-arm PEG crosslinker that is functionalized with reactive groups; wherein upon mixing the peptide sequence forms a hydrogel without the need for an external energy source.

14. The composition of claim 13, wherein the multi-arm PEG comprises from about 2 to about 8 arms.

15. The composition of claim 13, wherein the peptide sequence comprises a cell-adhesive RGD or YIGSR.

16. The composition of claim 15, wherein the peptide sequence is KKKRGDKKK, KKKYIGSRKKK, KKKYIGSR, RGDKKK, YIGSRKKK or KKKRGD or a combination or a multimer thereof.

17. The composition of claim 13, wherein the peptide sequence is formed as part of an interpenetrating polymer network with a second polymer.

18. The composition of claim 13, wherein the peptide sequence is formed as part of a co-polymer network with a second polymer.

19. The composition of claim 13, wherein the peptide comprises a sequence [KxRGD]Ky]n or [KxYIGSRKy]n where x and y are 0, 1, 2, 3, 4, 5, 6, 7, 8, or more and n is a positive integer, usually from 1 to 10.

* * * * *